(12) United States Patent
Takemoto et al.

(10) Patent No.: US 8,013,140 B2
(45) Date of Patent: Sep. 6, 2011

(54) PROMOTER FOR INTRODUCING A GENE INTO A LYMPHOCYTE OR BLOOD CELL AND APPLICATION THEREOF

(75) Inventors: Masaya Takemoto, Osaka (JP); Yasuko Mori, Osaka (JP); Koichi Yamanishi, Osaka (JP); Isao Fuke, Kagawa (JP); Yasuyuki Gomi, Kagawa (JP); Michiaki Takahashi, Osaka (JP)

(73) Assignee: The Resarch Foundation for Microbial Diseases of Osaka Universtiy, Osaka (JP)

( * ) Notice: Subject to any disclaimer, the term of this patent is extended or adjusted under 35 U.S.C. 154(b) by 0 days.

(21) Appl. No.: 12/195,665

(22) Filed: Aug. 21, 2008

(65) Prior Publication Data
US 2009/0214579 A1 Aug. 27, 2009

Related U.S. Application Data

(62) Division of application No. 11/991,637, filed as application No. PCT/JP2006/317574 on Sep. 5, 2006.

(30) Foreign Application Priority Data

Sep. 8, 2005 (JP) ................................. 2005-261366

(51) Int. Cl.
C07H 21/04 (2006.01)
C12N 15/63 (2006.01)
C12N 15/85 (2006.01)
C12P 21/00 (2006.01)

(52) U.S. Cl. ..................... 536/24.1; 435/320.1; 435/325; 435/70.1

(58) Field of Classification Search ........................ None
See application file for complete search history.

(56) References Cited

U.S. PATENT DOCUMENTS
5,879,936 A 3/1999 Bebbington et al.

FOREIGN PATENT DOCUMENTS
WO  WO 2005/021746 A1  3/2005
WO  WO 2005/068638 A2  7/2005

OTHER PUBLICATIONS

Zhao et al. 2000. AZ027916. RPCI-23-360N16. TJ Mus musculus genomic clone.*
Urushihara. AU074979, 1999. Dictyostelim discodeum SSM934.*
ADY51162, first entry, May 19, 2005. Human herpervirus 7. WO2005021746.*
Supplementary Partial European Search Report for EP 06 79 7474, search report dated Sep. 14, 2009, 14 pages.
Accession No. U92288, "Human herpesvirus 6 Serotype B putative major immediate-early genes", XP002545723, Jan. 14, 1998.
Accession No, AB021506, "Human herpesvirus 6B DNA, complete genome, strain: HST", XP002545724, Jun. 4, 1999.
Accession No. CC930625, "Sequencing of the Maize genome at PGIR", 2003.
Supplemental Partial European Search Report for EP 06 79 7474, search report dated Sep. 14, 2009, 14 pages (2009).
Frenkel N. et al., "Isolation of a new Herpesvirus from human CD4+ T cells", Proc. Natl. Acad. Sci., 87:748-752 (1990).
Kojima et al., "Vaccine Sosei no Shin Technology to Shinki Vaccine no Kaihatsu". Heisei 13-15 Nendo Soyakuto Human Science Kenkyu Sogo Kenkyu Hokokusho, Dai 5 Bunya Kenko Jumyo Enshin Yobo Shindan Chiryoho no Kaihatsu ni Kansuru Kenkyu, p. 51-54 (English Abstract Only for E) (2004).
Kojima et al., Vaccine Sosei no Shin Technology to Shinki Vaccine no Kaihatsu, Heisei 14 Nendo Soyakuto Human Science Kenkyu Sogo Hokokusho, Dai 5 Bunya Kenko Jumyo Enshin Yobo Shindan Chiryoho no Kaihatsu ni Kansuru Kenkyu, p. 48-53 (English Abstract Only for 5) (2003).
Kondo K. et al., "Identification of human herpesvirus 6 latency-associated transcripts", Journal of Virology, 76(8):4145-4151 (2002).
Kosuge H. et al., "Nucleotide sequence analysis of a 30-kilobase-pair region of human herpesvirus-6B (HHV-6B) genome and strain-specific variations in major immediate-early genes", Virus Research, 52:1-14 (1997).
Nicholas, John, "Determination and Analysis of the Complete Nucleotide Sequence of Human Herpesvirus 7", Journal of Virology, 70(9):5975-5989 (1996).
Takemoto M. et al., "The R3 region, one of the three major repetitive regions of human herpesvirus 6, is a strong enhancer of immediate-early gene U95", Journal of Virology, 75(21):10149-10160 (2001).
Tanaka K. et al., "Human herpesvirus 7: Another casual agent for roseola (exanthem subitum)", The Journal of Pediatrics, 125(1):1-5 (1994).
Tanaka-Taya K. et al., "Seroepidemiological study of human herpesvirus-6 and -7 in children of different ages and detection of these two viruses in throat swabs by polymerase chain reaction", Journal of Medical Virology, 48:88-94 (1996).
Yamada et al., "HIV Jizokukansen SupT1 Saibo heno HHV-6 oyobi -7 Choufukukannsen no Kokoromi (Attempt for HHV -6 and -7 Superinfection to HIV Persistent Infection Sup-T1 Cell)", Title No. 122, Titles and Abstracts of the 7th Annual Meeting of the Japanese Society for AIDS Research, Tokyo, pp. 1-72 (English Abstracts) (1993).
Yamanishi K. et al., "Identification of human herpesvirus-6 as a casual agent for exanthem subitum", Lancet, 1065-1067 (Saturday May 14, 1988).

(Continued)

Primary Examiner — Celine Qian
(74) Attorney, Agent, or Firm — King & Spalding LLP; Susan J. Myers Fitch; Peter J. Dehlinger

(57) ABSTRACT

It is intended to provide a promoter for inducing expression selectively and strongly in an immunocompetent cell and/or a blood cell such as a lymphocyte. In the invention, the object was achieved by finding that HHV6 MIE promoter, HHV7 MIE promoter and HHV7 U95 promoter unexpectedly induce a specific expression in an immunocompetent cell and/or a blood cell such as a T lymphocyte. By utilizing the promoters, a selective delivery of a DNA vaccine or the like can be realized.

18 Claims, 11 Drawing Sheets

OTHER PUBLICATIONS

Roest Crollius, et al., GeneBank Accession No. AL229845, "DNA from tetraodon nigroviridis genome survey sequence PUC-Ori end of clone 215L21 of library G from Tetraodon nigroviridus, genomic survey sequence", Accessed Online, http://www.ncbi.nlm.nih.gov/nucgss/aI229845.

Kosuge, et al., "Nucleotide sequence analysis of a 30-kilobase-pair region of human herpesvirus-6B (HHV-6B) genome and strain-specific variations in major immediate-early genes", Virus-Research, vol. 52, pp. 1-14 (1997).

* cited by examiner

SEQUENCE LISTING

```
<160> NUMBER OF SEQ ID NOS: 35

<210> SEQ ID NO 1
<211> LENGTH: 1242
<212> TYPE: DNA
<213> ORGANISM: Artificial
<220> FEATURE:
<223> OTHER INFORMATION: HHV6B MIE promoter sequence

<400> SEQUENCE: 1
agtgggtacc gcggttgggg tctttcctac ctaggctaac gagaacccta aaatctgcta      60
acggagcaac cgcagttcca gtttttctca taaaattaaa ggttagtggg taccgcggtt     120
gaaatctttc ctgctaataa ggatgagaac ttcaaaatct cgtaacgcgg caaccgcagt     180
tcctgttttt ctcataaagt taaagatcag cgggtaccgc ggttgaagta tttcctgccc     240
aggcgaatga gaactctaaa agctcgtaac gcggcaaccg agttcctgtt tttcccataa     300
agttaaagat cagcgggtac cgcggttgaa gtatttcctg tccaggcgaa tgagaactct     360
aaaagctcgt aacgcggcaa tcgcagttcc tgtttttctc ataaatttaa agatcagcgg     420
gtaccgcggt tgaagtattt cctgcccagg cgaatgagaa ctctaaaagc tcgtaacgcg     480
gcaaccgcag ttcctgtttt tcttataaag ttaaaaatta gcagatattg cggttgaagt     540
ctttcctgtt catgcgaatt aaaactctaa aaactgctaa cgaagcaacc gagttcctgt     600
ttttctcatt aagttaaagg ttagtgggta ctgtggttgg ggtctttcct acccaggcta     660
acgagaaccc taaaatctgc taacagagca accgcagttc ctgtttttct cataaagtta     720
aaggtcagtg tgtaccgcgg ttacaacatt ttcccctgac taagtcattt atttcgtgag     780
aagcgctaac accaaaacca cattcctgtt tcatgatgtg tagcagatgt ttttaaaaaa     840
aaaacatgac aatttatcag taaagtgttc tttattatcc cgccttcaac cgcaaactcc     900
gtctttctca taaaaaata caagtcagcc ataagaagaa aacctcaaaa aatccagacc     960
acaaattcct gttttgagt aagatatgac aaaaccctaa attttgtaa gcatcagcta    1020 atttccattc catatttgtc taaaaggggt gtatttctac acttgcggtt taacattata    1080
cagcgattgg ctccttcatc ctcgtcattt tcctgtacat cacaccgct atagaattgt     1140 atataagcag aagttacagc cagttcagtg ccactttct caagaagtgg ctccggagaa    1200
cattctcatc acagagattc tttcttatat cgctgcagtc tg                       1242

<210> SEQ ID NO 2
<211> LENGTH: 515
<212> TYPE: DNA
<213> ORGANISM: Artificial
<220> FEATURE:
```

<223> OTHER INFORMATION: HHV7 MIE promoter sequence

<400> SEQUENCE: 2

```
cgcagttcct gttgttttca catattaaaa tgttagtggg ttatgtggtt ggggtctttc      60
ctgcctaaac gggtgagaac ccgtaaaacc tgctgagaag caaccgcag ttcctgttgt     120
tttcacgggt ttaaatgtca gtgggttatg tggttggggt cttttcctgcc taaagcgagt   180
gggaatgtgt agaacttgct gagaagacaa ccgcaattcc tgttgtttca agatttaaa    240
taccaattcg aaataaaata accgcaaaaa tcatgtttac gtaaaatata aatccattgt    300
ggttttatt ggaaaaataa tattttaaaa aaatacatgt acaaataagg ttaaacccta    360
atttttttag tattataatt ttttggcttt ttttaattgg ttgatatatt aacgtcattt    420
tcctgtgcat cacatccgct tcaaaatgta tataataaga agacagatca actattttgc   480
cactttttct tcaagagctt gaagatacag ttctg                               515
```

<210> SEQ ID NO 3
<211> LENGTH: 1243
<212> TYPE: DNA
<213> ORGANISM: Artificial
<220> FEATURE:
<223> OTHER INFORMATION: HHV6A MIE promoter sequence

<400> SEQUENCE: 3

```
tgggtatcgc ggtttggggg tctttcctgc acaggcgaac gagaactcta aaagctgcta     60
acgcggcaac cgcagtttct gttttttctcg gaaaattaaa agtcagtggg taccgcggtt   120
tggggggtctt tcctgcacag gcgaacgaga actctaaaag ctgctaacgc ggcaaccgca   180
gtttctgttt ttctcggaaa attaaaagtc agtgggtacc gcggtttggg gtctttcctg    240
cacaggcgaa cgaaaactct aaaagctgct aacgcggcaa ccgcagtttc tgttttctc    300
ggaaaactaa aagtcagtgg gtaccgcggt ttgggtctt tcctgcacag gcgaacgaga    360
actctaaaag ctgctaacgc ggcaaccgca gttcctgttt tcttcataa agataaagat   420
cagtgggtac cgcggttggg gtctttcctg cacaggcgaa cgagaactct aaaagctgct   480
aacgcggcaa ccgcagtttc tgttttctc ggaaaattaa aggtcagtgg gtaccgcggt    540
tgaggtgttt cctacccagg cgaacgagaa ctctaacatc tgctaacgcg gcaaccgcag   600
ttcctgttct tctcagaaaa ataaaggtca gtgggtaccg cggttgaggt gtttcctgcc   660
caggcgaacg agaactctaa catctcgtaa cgcggcaacc gcagttcctg ttttttctcgg   720
aaaatatttc ctgcccaggc aaacgagaac tctaaaatct cgtaacgcgg caaccgcagt   780
tcctgttttt ctcggaaaat taaaggtcag tgggtatcgc ggttggggtc tttcctgccc   840
aagctaacaa gaaccctaaa atttgctaac ggggcaaccg cagttcctgt ttttctcata    900
aaattaaagg ttagtgggga ccgcgattgc aacatttcc tctgactgag tcatttattt    960
attgagaaac gctaacacca aaccacatg tcttatgatg tgtaacagat gttcttagaa    1020
aaaacatgac aatttatcag taaatgttg tttattataa aaaacctcaa aaaatccaga   1080
ccacaaattc ctgttttttgt aaaatataac aaaaccctaa attttgcaa gcattaacta   1140
atttcaattc catatttgtc taaaggggt gtatttctgc acttgcggtt taacgttatg    1200
cagcgattgg ttccttcatc ttcgtcattt tcctgtacat cac                      1243
```

<210> SEQ ID NO 4
<211> LENGTH: 2503
<212> TYPE: DNA
<213> ORGANISM: Artificial
<220> FEATURE:

<223> OTHER INFORMATION: sequence of HHV6B R3 region

<400> SEQUENCE: 4

```
atgtggtttt ggtgttagcg cttctcacga aataaatgac ttagtcaggg gaaaatgttg      60
taaccgcggt acacactgac ctttaacttt atgagaaaaa caggaactgc ggttgctctg     120
ttagcagatt ttagggttct cgttagcctg ggtaggaaag accccaacca cagtacccac     180
taacctttaa cttaatgaga aaacaggaa ctcggttgct tcgttagcag tttttagagt      240
tttaattcgc atgaacagga aagacttcaa ccgcaatatc tgctaatttt aactttata      300
agaaaaacag gaactgcggt tgccgcgtta cgagctttta gagttctcat tcgcctgggc     360
aggaaatact tcaaccgcgg tacccgctga tctttaaatt tatgagaaaa acaggaactg     420
cgattgccgc gttacgagct tttagagttc tcattcgcct ggacaggaaa tacttcaacc     480
gcggtacccg ctgatcttta actttatggg aaaaacagga actcggttgc cgcgttacga     540
gcttttagag ttctcattcg cctgggcagg aaatacttca accgcggtac cgctgatct      600
ttaactttat gagaaaaaca ggaactgcgg ttgccgcgtt acgagatttt gaagttctca     660
tccttattag caggaaagat ttcaaccgcg gtacccacta acctttaatt ttatgagaaa     720
aactggaact gcggttgctc cgttagcaga ttttagggtt ctcgttagcc taggtaggaa     780
agaccccaac cgcggtaccc actgatcttt aactttatga gaaaaacaga aattgcggtt     840
tcccccatta gcagattttg aagttctcat ccttattagc aggaaagatt tcaaccgcgg     900
tacccactaa cctttaactt tatgagaaaa acaggaactg cggttgctcc gttagcaggt     960
tttagggttc tcgttagcct gggtaggaaa gaccccaacc gcagtaccca ctaaccttta    1020
actttatgag aaaaacagga actcggttgc tccgttagca ggttttaggg ttctcgttag    1080
cctgggtaag aaagacccca accgcagtac ccactaacct ttaactttat gagaaaaaca    1140
ggaactgcgg ttgctccgtt agcaggtttt agggttctcg ttagcctggg taagaaagac    1200
cccaaccgca gtacccacta acctttaact ttatgagaaa acaggaact gcggttgctc     1260
cgttagcagg ttttagagtt ttaattcgca taatcaggaa agacttcaac cgcggtaccc    1320
actaaccttt aactttatga gaaaaacagg aattgcggtt gctccgttag cagattttag    1380
ggttctcgtt agcctgggta ggaaagaccc caaccgcagt acccactaac ctttaacttt    1440
atgagaaaaa cagaaactgc ggttgctccg ttagcagctt ttagagtttt aattcgcatg    1500
aacaggaaag acttcaaccg cggtacccgc tgatctttaa ctttctgaga aaaacaggaa    1560
ctgcggttgc cgcgttacga acttttgaa gttctcatcc ttattagcag aaagattta      1620
aaccgcagta cccactaacc tttaagttta tgaggaaaaa caggaactgc ggttgctttg    1680
ttagcatctt ttagagttct cattcgtatt ggcaggaaat acttcaaccg cggtacccac    1740
tgatctttaa ctttatgaag aaaaacagga actttgttgc tttgttagca gattttaaag    1800
ttctcatcct cattatcagg aaagacttca accgcagttc ccactgacct ttaagtttat    1860
gaggaaaaac aggaaatgcg gttgctttgt taacagcttt tagagttctc atccgtatgg    1920
gcaaaaaaa tttcaaccgc ggtacccact gatctttagc tttatcagaa aaacagaaa     1980
ctgcggttgc cccattagcg gattttaggg tcctcaccca cttgagtagg aaagacccta    2040
accgcggcac ccactgacct taactgtat gaagagaaac agaaactgcg gttgcccagt     2100
tagcaatttt taaggttctc acccgcttgg gtaggaaaga ccctaaccgc ggcacccact    2160
gacctttaac tttatgagga gaacagaaa ctgcggttgc cccgttagta atttttaagg     2220
ttctcacccg cttgggtagg aaagacccta accgcggcac ccactgacct ttaacttttt    2280
```

| | |
|---|---|
| gatgaaaaac agaagctgcg gttgccccgt tagcaattt taaggttctc acccgcttgg | 2340 |
| gtaggaaaga ccctaaccgc ggcacccact gacctttaac tttttgatga aaaacagaag | 2400 |
| ctgcggttgc cccgttagca attttaagg ttctcacccg cttgggtagg aaagacccta | 2460 |
| accgcggcac ccactgacat ttaaatttat ggaaaaacaa act | 2503 |

<210> SEQ ID NO 5
<211> LENGTH: 1242
<212> TYPE: DNA
<213> ORGANISM: Artificial
<220> FEATURE:
<223> OTHER INFORMATION: sequence of 20u in EXAMPLE 1

<400> SEQUENCE: 5

| | |
|---|---|
| agtgggtacc gcggttgggg tctttcctac ctaggctaac gagaaccta aaatctgcta | 60 |
| acggagcaac cgcagttcca gttttttctca taaaattaaa ggttagtggg taccgcggtt | 120 |
| gaaatctttc ctgctaataa ggatgagaac ttcaaaatct cgtaacgcgg caaccgcagt | 180 |
| tcctgttttt ctcataaagt taaagatcag cgggtaccgc ggttgaagta tttcctgccc | 240 |
| aggcgaatga gaactctaaa agctcgtaac gcggcaaccg agttcctgtt tttcccataa | 300 |
| agttaaagat cagcgggtac cgcggttgaa gtatttcctg tccaggcgaa tgagaactct | 360 |
| aaaagctcgt aacgcggcaa tcgcagttcc tgtttttctc ataaatttaa agatcagcgg | 420 |
| gtaccgcggt tgaagtattt cctgcccagg cgaatgagaa ctctaaaagc tcgtaacgcg | 480 |
| gcaaccgcag ttcctgtttt tcttataaag ttaaaaatta gcagatattg cggttgaagt | 540 |
| ctttcctgtt catgcgaatt aaaactctaa aaactgctaa cgaagcaacc gagttcctgt | 600 |
| ttttctcatt aagttaaagg ttagtgggta ctgtggttgg ggtctttcct acccaggcta | 660 |
| acgagaaccc taaaatctgc taacagagca accgcagttc ctgtttttct cataaagtta | 720 |
| aaggtcagtg tgtaccgcgg ttacaacatt tcccctgac taagtcattt atttcgtgag | 780 |
| aagcgctaac accaaaacca cattcctgtt tcatgatgtg tagcagatgt ttttaaaaaa | 840 |
| aaaacatgac aatttatcag taaagtgttc tttattatcc cgccttcaac cgcaaactcc | 900 |
| gtctttctca taaaaaata caagtcagcc ataagaagaa aacctcaaaa aatccagacc | 960 |
| acaaattcct gttttgagt aagatatgac aaaaccctaa attttgtaa gcatcagcta | 1020 |
| atttccattc catatttgtc taaaggggt gtatttctac acttgcggtt taacattata | 1080 |
| cagcgattgg ctccttcatc ctcgtcattt tcctgtacat cacacccgct atagaattgt | 1140 |
| atataagcag aagttacagc cagttcagtg ccacttttct caagaagtgg ctccggagaa | 1200 |
| cattctcatc acagagattc tttcttatat cgctgcagtc tg | 1242 |

<210> SEQ ID NO 6
<211> LENGTH: 1053
<212> TYPE: DNA
<213> ORGANISM: Artificial
<220> FEATURE:
<223> OTHER INFORMATION: sequence of 9u in EXAMPLE 1

<400> SEQUENCE: 6

| | |
|---|---|
| cagactgcag cgatataaga aagaatctct gtgatgagaa tgttctccgg agccacttct | 60 |
| tgagaaaagt ggcactgaac tggctgtaac ttctgcttat atacaattct atagcgggtg | 120 |
| tgatgtacag gaaaatgacg aggatgaagg agccaatcgc tgtataatgt taaaccgcaa | 180 |
| gtgtagaaat acaccccttt tagacaaata tggaatggaa attagctgat gcttacaaaa | 240 |
| atttagggtt ttgtcatatc ttactcaaaa acaggaattt gtggtctgga ttttttgagg | 300 |

| | |
|---|---|
| ttttcttctt atggctgact tgtatttttt tatgagaaag acggagtttg cggttgaagg | 360 |
| cgggataata aagaacactt tactgataaa ttgtcatgtt tttttttttaa aaacatctgc | 420 |
| tacacatcat gaaacaggaa tgtggttttg tgttagcgc ttctcacgaa ataaatgact | 480 |
| tagtcagggg aaaatgttgt aaccgcggta cacactgacc tttaactttta tgagaaaaac | 540 |
| aggaactgcg gttgctctgt tagcagattt tagggttctc gttagcctgg gtaggaaaga | 600 |
| ccccaaccac agtacccact aacctttaac ttaatgagaa aaacaggaac tgcggttgct | 660 |
| tcgttagcag ttttttagagt tttaattcgc atgaacagga aagacttcaa ccgcaatatc | 720 |
| tgctaattttt taactttata agaaaaacag gaactgcggt tgccgcgtta gcagctttta | 780 |
| gagttctcat tcgcctgggc aggaaatact tcaaccgcgg tacccgctga tctttaaatt | 840 |
| tatgagaaaa acaggaactg cgattgccgc gttagcagct tttagagttc tcattcgcct | 900 |
| ggacaggaaa tacttcaacc gcggtacccg ctgatcttta actttatggg aaaaacagga | 960 |
| actgcggttg ccgcgttagc agcttttaga gttctcattc gcctgggcag gaaatacttc | 1020 |
| aaccgcggta cccgctgatc tttaacttta tga | 1053 |

<210> SEQ ID NO 7
<211> LENGTH: 754
<212> TYPE: DNA
<213> ORGANISM: Artificial
<220> FEATURE:
<223> OTHER INFORMATION: sequence of MIE in EXAMPLE 1

<400> SEQUENCE: 7

| | |
|---|---|
| atcagcgggt accgcggttg aagtatttcc tgcccaggcg aatgagaact ctaaaagctc | 60 |
| gtaacgcggc aaccgcagtt cctgtttttc ttataaagtt aaaaattagc agatattgcg | 120 |
| gttgaagtct ttcctgttca tgcgaattaa aactctaaaa actgctaacg aagcaaccga | 180 |
| gttcctgttt ttctcattaa gttaaaggtt agtgggtact gtggttgggg tctttcctac | 240 |
| ccaggctaac gagaacccta aatctgcta acagagcaac cgcagttcct gttttttctca | 300 |
| taaagtaaaa ggtcagtgtg taccgcggtt acaacatttt cccctgacta agtcattttat | 360 |
| ttcgtgagaa gcgctaacac caaaaccaca ttcctgtttc atgatgtgta gcagatgttt | 420 |
| ttaaaaaaaa aacatgacaa tttatcagta agtgttctt tattatcccg ccttcaaccg | 480 |
| caaactccgt ctttctcata aaaaaataca agtcagccat aagaagaaaa cctcaaaaaa | 540 |
| tccagaccac aaattcctgt ttttgagtaa gatatgacaa acccctaaat tttgtaagc | 600 |
| atcagctaat ttccattcca tatttgtcta aaaggggtgt attttctacac ttgcggttta | 660 |
| acattataca gcgattggct ccttcatcct cgtcattttt c ctgtacatca cacccgctat | 720 |
| agaattgtat ataagcagaa gttacagcca gttc | 754 |

<210> SEQ ID NO 8
<211> LENGTH: 756
<212> TYPE: DNA
<213> ORGANISM: Artificial
<220> FEATURE:
<223> OTHER INFORMATION: sequence of U95 in EXAMPLE 1

<400> SEQUENCE: 8

| | |
|---|---|
| tttagggtcc tcacccactt gagtaggaaa gaccctaacc gcggcaccca ctgacccttta | 60 |
| actgtatgaa gagaaacaga aactgcggtt gcccagttag caattttttaa ggttctcacc | 120 |
| cgcttgggta ggaagaccc taaccgcggc acccactgac cttttaactttt atgaggagaa | 180 |
| acagaaactg cggttgcccc gttagtaatt tttaaggttc tcacccgctt gggtaggaaa | 240 |

```
gaccctaacc gcggcaccca ctgaccttta acttttgat gaaaaacaga agctgcggtt      300
gccccgttag caatttttaa ggttctcacc cgcttgggta ggaaagaccc taaccgcggc      360
acccactgac ctttaacttt tgatgaaaa acagaagctg cggttgcccc gttagcaatt      420
tttaaggttc tcacccgctt gggtaggaaa gaccctaacc gcggcaccca ctgacattta      480
aatttatgga aaacaaact ttttttgttca tcatgcactt ttttatatat cattatatct      540
ctatccaatc agcactcttg agggtgcata cattaaggca gtgttgattt tttttcattg      600
tacccactta cgaataacga atcaaaagcc gtgaagtaga atattttaat gatgtattaa      660
tcatcatttc ctaccacgcc tattaacttc agtatttata ggataggcaa tttgccgcta      720
tacgccatta gctgttcttc tgctagcttg gacaca                              756
```

<210> SEQ ID NO 9
<211> LENGTH: 655
<212> TYPE: DNA
<213> ORGANISM: Artificial
<220> FEATURE:
<223> OTHER INFORMATION: sequence of CMV in EXAMPLE 1

<400> SEQUENCE: 9

```
cgatgtacgg gccagatata cgcgttgaca ttgattattg actagttatt aatagtaatc       60
aattacgggg tcattagttc atagcccata tatggagttc cgcgttacat aacttacggt      120
aaatggcccg cctggctgac cgcccaacga ccccgccca ttgacgtcaa taatgacgta      180
tgttcccata gtaacgccaa tagggacttt ccattgacgt caatgggtgg agtatttacg      240
gtaaactgcc cacttggcag tacatcaagt gtatcatatg ccaagtacgc ccctattga       300 cgtcaatgac ggtaaatggc ccgcctggca ttatgcccag tacatgacct tatgggactt      360
tcctacttgg cagtacatct acgtattagt catcgctatt accatggtga tgcggttttg      420
gcagtacatc aatgggcgtg gatagcggtt tgactcacgg ggatttccaa gtctccaccc      480
cattgacgtc aatgggagtt tgttttggca ccaaaatcaa cgggactttc caaaatgtcg      540
taacaactcc gccccattga cgcaaatggg cggtaggcgt gtacggtggg aggtctatat      600
aagcagagct ctctggctaa ctagagaacc cactgcttac tggcttatcg aaatt          655
```

<210> SEQ ID NO 10
<211> LENGTH: 3136
<212> TYPE: DNA
<213> ORGANISM: Artificial
<220> FEATURE:
<223> OTHER INFORMATION: sequence of MIE/3K region in EXAMPLE 1

<400> SEQUENCE: 10

```
tgtgtccaag ctagcagaag aacagctaat ggcgtatagc ggcaaattgc ctatcctata       60
aatactgaag ttaataggcg tggtaggaaa tgatgattaa tacatcatta aaatattcta      120
cttcacggct tttgattcgt tattcgtaag tgggtacaat gaaaaaaaat caacactgcc      180
ttaatgtatg caccctcaag agtgctgatt ggatagagat ataatgatat ataaaaaagt      240
gcatgatgaa caaaaaagtt tgttttttcca taaatttaaa tgtcagtggg tgccgcggtt      300
agggtctttc ctacccaagc gggtgagaac cttaaaaatt gctaacgggg caaccgcagc      360
ttctgttttt catcaaaaag ttaaaggtca gtgggtgccg cggttagggt ctttcctacc      420
caagcgggtg agaaccttaa aaattgctaa cggggcaacc gcagcttctg tttttcatca      480 aaagttaaa ggtcagtggg tgccgcggtt agggtctttc ctacccaagc gggtgagaac      540
cttaaaaatt actaacgggg caaccgcagt ttctgttttct cctcataaag ttaaaggtca      600
```

```
gtgggtgccg cggttagggt ctttcctacc caagcgggtg agaaccttaa aaattgctaa      660
ctgggcaacc gcagtttctg tttctcttca tacagttaaa ggtcagtggg tgccgcggtt      720
agggtctttc ctactcaagt gggtgaggac cctaaaatcc gctaatgggg caaccgcagt      780
ttctgttttt tctgataaag ctaaagatca gtgggtaccg cggttgaaat ttttttgcc       840 catacggatg agaactctaa aagctgttaa caaagcaacc gcatttcctg ttttcctca       900 taaacttaaa ggtcagtggg aactgcggtt gaagtctttc ctgataatga ggatgagaac      960
tttaaaatct gctaacaaag caacaaagtt cctgttttc ttcataaagt taaagatcag      1020
tgggtaccgc ggttgaagta tttcctgcca atacgaatga aactctaaa agatgctaac      1080 aaagcaaccg cagttcctgt ttttcctcat aaacttaaag gttagtgggt actgcggttt     1140
aaatctttcc tgctaataag gatgagaact tcaaaagtct cgtaacgcgg caaccgcagt     1200
tcctgttttt ctcagaaagt taaagatcag cgggtaccgc ggttgaagtc tttcctgttc     1260
atgcgaatta aaactctaaa agctgctaac ggagcaaccg cagtttctgt ttttctcata     1320
aagttaaagg ttagtgggta ctgcggttgg ggtctttcct acccaggcta acgagaaccc     1380
taaaatctgc taacggagca accgcaattc ctgtttttct cataaagtta aaggttagtg     1440
ggtaccgcgg ttgaagtctt tcctgattat gcgaattaaa actctaaaac ctgctaacgg     1500
agcaaccgca gttcctgttt ttctcataaa gttaaaggtt agtgggtact gcggttgggg     1560
tctttcttac ccaggctaac gagaacccta aaacctgcta acggagcaac cgcagttcct     1620
gtttttctca taaagttaaa ggttagtggg tactgcggtt ggggtctttc ttacccaggc     1680
taacgagaac cctaaaacct gctaacggag caaccgagtt cctgttttc tcataaagtt      1740 aaaggttagt gggtactgcg gttggggtct ttcctaccca ggctaacgag aaccctaaaa     1800
cctgctaacg gagcaaccgc agttcctgtt tttctcataa agttaaaggt tagtgggtac     1860
cgcggttgaa atctttcctg ctaataagga tgagaacttc aaaatctgct aatggggaa      1920 accgcaattt ctgttttcct cataaagtta agatcagtg ggtaccgcgg ttggggtctt      1980
tcctacctag gctaacgaga accctaaaat ctgctaacgg agcaaccgca gttccagttt     2040
ttctcataaa attaaaggtt agtgggtacc gcggttgaaa tctttcctgc taataaggat     2100
gagaacttca aaatctcgta acgcggcaac cgcagttcct gttttctca taaagttaaa      2160 gatcagcggg taccgcggtt gaagtatttc ctgcccaggc gaatgagaac tctaaaagct     2220
cgtaacgcgg caaccgagtt cctgttttt ccataaagtt aaagatcagc gggtaccgcg      2280
gttgaagtat ttcctgtcca ggcgaatgag aactctaaaa gctcgtaacg cggcaatcgc     2340
agttcctgtt tttctcataa atttaaagat cagcgggtac cgcggttgaa gtatttcctg     2400
cccaggcgaa tgagaactct aaaagctcgt aacgcggcaa ccgcagttcc tgttttcctt     2460
ataaagttaa aaattagcag atattgcggt tgaagtctttt cctgttcatg cgaattaaaa    2520
ctctaaaaac tgctaacgaa gcaaccgagt tcctgttttt ctcattaagt taaaggttag     2580
tgggtactgt ggttggggtc tttcctaccc aggctaacga gaaccctaaa atctgctaac     2640
agagcaaccg cagttcctgt ttttctcata aagttaaagg tcagtgtgta ccgcggttac     2700 aacatttcc cctgactaag tcatttattt cgtgagaagc gctaacacca aaaccacatt      2760
cctgtttcat gatgtgtagc agatgttttt aaaaaaaaaa catgacaatt tatcagtaaa     2820
gtgttcttta ttatcccgcc ttcaaccgca aactccgtct ttctcataaa aaaatacaag     2880
tcagccataa gaagaaaacc tcaaaaaatc cagaccacaa attcctgttt ttgagtaaga     2940
tatgacaaaa ccctaaattt ttgtaagcat cagctaattt ccattccata tttgtctaaa    3000
```

```
agggqtqtat ttctacactt gcggtttaac attatacagc gattggctcc ttcatcctcg    3060
tcattttcct gtacatcaca cccgctatag aattgtatat aagcagaagt tacagccagt    3120
tcagtgccac tttcct                                                    3136
```

<210> SEQ ID NO 11
<211> LENGTH: 3136
<212> TYPE: DNA
<213> ORGANISM: Artificial
<220> FEATURE:
<223> OTHER INFORMATION: sequence of U95/3K region in EXAMPLE 1

<400> SEQUENCE: 11

```
agaaaagtgg cactgaactg gctgtaactt ctgcttatat acaattctat agcgggtgtg      60
atgtacagga aaatgacgag gatgaaggag ccaatcgctg tataatgtta aaccgcaagt     120
gtagaaatac accccttta gacaaatatg gaatggaaat tagctgatgc ttacaaaaat     180
ttagggtttt gtcatatctt actcaaaaac aggaatttgt ggtctggatt ttttgaggtt     240
ttcttcttat ggctgacttg tatttttta tgagaaagac ggagtttgcg gttgaaggcg     300
ggataataaa gaacacttta ctgataaatt gtcatgtttt tttttaaaa acatctgcta     360 cacatcatga acaggaatg tggttttggt gttagcgctt ctcacgaaat aaatgactta     420
gtcaggggaa aatgttgtaa ccgcggtaca cactgacctt taactttatg agaaaaacag     480
gaactgcggt tgctctgtta gcagatttta gggttctcgt tagcctgggt aggaaagacc     540
ccaaccacag tacccactaa cctttaactt aatgagaaaa acaggaactc ggttgcttcg     600
ttagcagttt ttagagtttt aattcgcatg aacaggaaag acttcaaccg caatatctgc     660 taattttaa ctttataaga aaacaggaa ctgcggttgc cgcgttacga gcttttagag     720
ttctcattcg cctgggcagg aaatacttca accgcggtac ccgctgatct ttaaatttat     780
gagaaaaaca ggaactgcga ttgccgcgtt acgagctttt agagttctca ttcgcctgga     840
caggaaatac ttcaaccgcg gtaccgctg atctttaact ttatgggaaa acaggaact     900 cggttgccgc gttacgagct tttagagttc tcattcgcct gggcaggaaa tacttcaacc     960
gcggtacccg ctgatctta actttatgag aaaaacagga actgcggttg ccgcgttacg    1020
agattttgaa gttctcatcc ttattagcag gaaagatttc aaccgcggta cccactaacc    1080
tttaatttta tgagaaaaac tggaactgcg gttgctccgt tagcagattt tagggttctc    1140
gttagcctag gtaggaaaga cccccaaccgc ggtacccact gatctttaac tttatgagaa    1200
aaacagaaat tgcggttttcc cccattagca gattttgaag ttctcatcct tattagcagg    1260
aaagatttca accgcggtac ccactaacct ttaactttat gagaaaaaca ggaactgcgg    1320
ttgctccgtt agcaggtttt agggttctcg ttagcctggg taggaaagac cccaaccgca    1380
gtacccacta acctttaact ttatgagaaa aacaggaact cggttgctcc gttagcaggt    1440
tttagggttc tcgttagcct gggtaagaaa gaccccaacc gcagtaccca ctaaccttta    1500
actttatgag aaaaacagga actgcggttg ctccgttagc aggttttagg gttctcgtta    1560
gcctgggtaa gaaagacccc aaccgcagta cccactaacc tttaacttta tgagaaaaac    1620
aggaactgcg gttgctccgt tagcaggttt tagagtttta attcgcataa tcaggaaaga    1680
cttcaaccgc ggtacccact aacctttaac tttatgagaa aacaggaat tgcggttgct    1740 ccgttagcag attttagggt tctcgttagc ctgggtagga agaccccaa ccgcagtacc    1800 cactaacctt taactttatg agaaaaacag aaactgcggt tgctccgtta gcagcttta    1860 gagttttaat tcgcatgaac aggaaagact tcaaccgcgg tacccgctga tctttaactt    1920
```

```
tctgagaaaa acaggaactg cggttgccgc gttacgagac ttttgaagtt ctcatcctta    1980
ttagcaggaa agatttaaac cgcagtaccc actaacctttt aagtttatga ggaaaaacag    2040
gaactgcggt tgctttgtta gcatctttta gagttctcat tcgtattggc aggaaatact    2100
tcaaccgcgg tacccactga tctttaactt tatgaagaaa acaggaact tgttgctttt    2160 gttagcagat tttaaagttc tcatcctcat tatcaggaaa gacttcaacc gcagttccca    2220
ctgaccttta agtttatgag gaaaaacagg aaatgcggtt gctttgttaa cagcttttag    2280
agttctcatc cgtatgggca aaaaaattt caaccgcggt acccactgat ctttagcttt    2340
atcagaaaaa acagaaactg cggttgcccc attagcggat tttagggtcc tcacccactt    2400
gagtaggaaa gaccctaacc gcggcaccca ctgacccttta actgtatgaa gagaaacaga    2460
aactgcggtt gcccgttag caatttttaa ggttctcacc cgcttgggta ggaaagaccc    2520
taaccgcggc acccactgac ctttaacttt atgaggagaa acagaaactg cggttgcccc    2580
gttagtaatt tttaaggttc tcacccgctt gggtaggaaa gaccctaacc gcggcaccca    2640 ctgacccttta acttttttgat gaaaaacaga agctgcggtt gccccgttag caatttttaa    2700
ggttctcacc cgcttgggta ggaaagaccc taaccgcggc acccactgac ctttaacttt    2760
ttgatgaaaa acagaagctg cggttgcccc gttagcaatt tttaaggttc tcacccgctt    2820
gggtaggaaa gaccctaacc gcggcaccca ctgacatta aatttatgga aaaacaaact    2880 ttttgttca tcatgcactt ttttatatat cattatatct ctatccaatc agcactcttg    2940
agggtgcata cattaaggca gtgttgattt tttttcattg tacccactta cgaataacga    3000
atcaaaagcc gtgaagtaga atatttaaat gatgtattaa tcatcatttc ctaccacgcc    3060
tattaacttc agtatttata ggataggcaa tttgccgcta tacgccatta gctgttcttc    3120
tgctagcttg gacaca                                                     3136

<210> SEQ ID NO 12
<211> LENGTH: 500
<212> TYPE: DNA
<213> ORGANISM: Artificial
<220> FEATURE:
<223> OTHER INFORMATION: HHV7 U95 promoter sequence

<400> SEQUENCE: 12
tgggttctca cccgtttagg caggaaacac ccagaccgca taacccactg acatttaaac      60
ccgtgaaaac aacaggaact gcggttgact tctcagcagg ttttatgggt tctcacccgt     120
ttaggtagga agacccaga ccgcataacc cactaacatt ttaatatgtg aaaataaaca      180
ggaactgcgg ttatagtttc agtacattct agagattaca tcctgctaag gcgaaaaaca     240
ctttaaccgc aaaagccact gattttttaaa cttgtgaaaa taacaggaaa ccacagaaac     300
gtcaggaaaa aaacgttgtt ttataattat gtccataaaa catgcaacat aatccaaacc     360
ggccaatgat ttttctgctt aaatgtaatt taaataattt attcatacgt aagttgttat     420
agccacgcct acgcagcaat gtatataagc agacaccgtc atttcgcagt tagtctgctg     480
gaaagcttgt gaagactaca                                                 500

<210> SEQ ID NO 13
<211> LENGTH: 148
<212> TYPE: DNA
<213> ORGANISM: Artificial
<220> FEATURE:
<223> OTHER INFORMATION: -574 to -427 from transcription initiation
      point of HHV-6B MIE

<400> SEQUENCE: 13
```

```
acccaggcta acgagaaccc taaaatctgc taacagagca accgcagttc ctgttttct      60 cataaagtta aaggtcagtg tgtaccgcgg ttacaacatt ttccctgac taagtcattt     120 atttcgtgag aagcgctaac accaaaac                                       148
```

<210> SEQ ID NO 14
<211> LENGTH: 625
<212> TYPE: DNA
<213> ORGANISM: Artificial
<220> FEATURE:
<223> OTHER INFORMATION: -1051 to -427 from transcription initiation
      point of HHV-6B MIE

<400> SEQUENCE: 14

```
ctagcccggg ctcgagatct tcagttaaag atcagcgggt accgcggttg aagtatttcc     60
tgcccaggcg aatgagaact ctaaaagctg ctaacgcggc aaccgcagtt cctgttttc     120 ccataaagtt aaagatcagc gggtaccgcg gttgaagtat ttcctgtcca ggcgaatgag    180
aactctaaaa gctgctaacg cggcaatcgc agttcctgtt tttctcataa atttaaagat    240
cagcgggtac cgcggttgaa gtatttcctg cccaggcgaa tgagaactct aaaagctgct    300
aacgcggcaa ccgcagttcc tgttttcctt ataaagttaa aaattagcag atattgcggt    360
tgaagtcttt cctgttcatg cgaattaaaa ctctaaaaac tgctaacgaa gcaaccgcag    420
ttcctgtttt tctcattaag ttaaaggtta gtgggtactg tggttggggt ctttcctacc    480
caggctaacg agaaccctaa aatctgctaa cagagcaacc gcagttcctg tttttctcat    540
aaagttaaag gtcagtgtgt accgcggtta caacattttc ccctgactaa gtcatttatt    600
tcgtgagaag cgctaacacc aaaac                                          625
```

<210> SEQ ID NO 15
<211> LENGTH: 515
<212> TYPE: DNA
<213> ORGANISM: Artificial
<220> FEATURE:
<223> OTHER INFORMATION: +22 to -493 from transcription initiation
      point of HHV-7 MIE

<400> SEQUENCE: 15

```
cgcagttcct gttgttttca catattaaaa tgttagtggg ttatgtggtt ggggtctttc     60
ctgcctaaac gggtgagaac ccgtaaaacc tgctgagaag gcaaccgcag ttcctgttgt    120
tttcacgggt ttaaatgtca gtgggttatg tggttggggt ctttcctgcc taaagcgagt    180
gggaatgtgt agaacttgct gagaagacaa ccgcaattcc tgttgtttca aagatttaaa    240
taccaattcg aaataaaata accgcaaaaa tcatgtttac gtaaaatata atccattgt     300 ggttttatt ggaaaaataa tattttaaaa aaatacatgt acaataagg ttaaacccta      360 attttttag tattataatt ttttggcttt ttttaattgg ttgatatatt aacgtcattt     420
tcctgtgcat cacatccgct tcaaaatgta tataataaga agacagatca actattttgc    480
cactttttct tcaagagctt gaagatacag ttctg                               515
```

<210> SEQ ID NO 16
<211> LENGTH: 500
<212> TYPE: DNA
<213> ORGANISM: Artificial
<220> FEATURE:
<223> OTHER INFORMATION: +16 to -484 from transcription initiation
      point of HHV-7 U95

<400> SEQUENCE: 16

```
tgggttctca cccgtttagg caggaaacac ccagaccgca taacccactg acatttaaac      60
ccgtgaaaac aacaggaact gcggttgact tctcagcagg ttttatgggt tctcacccgt     120
ttaggtagga aagacccaga ccgcataacc cactaacatt ttaatatgtg aaaataaaca     180
ggaactgcgg ttatagtttc agtacattct agagattaca tcctgctaag gcgaaaaaca     240
ctttaaccgc aaaagccact gattttttaaa cttgtgaaaa taacaggaaa ccacagaaac    300
gtcaggaaaa aaacgttgtt ttataattat gtccataaaa catgcaacat aatccaaacc     360
ggccaatgat ttttctgctt aaatgtaatt taaataattt attcatacgt aagttgttat     420
agccacgcct acgcagcaat gtatataagc agacaccgtc atttcgcagt tagtctgctg     480
gaaagcttgt gaagactaca                                                  500

<210> SEQ ID NO 17
<211> LENGTH: 816
<212> TYPE: DNA
<213> ORGANISM: Artificial
<220> FEATURE:
<223> OTHER INFORMATION: sequence of 9u-d2-7 in EXAMPLE 1

<400> SEQUENCE: 17
aaaatttagg gttttgtcat atcttactca aaaacaggaa tttgtggtct ggattttttg      60
aggttttctt cttatggctg acttgtattt ttttatgaga aagacggagt ttgcggttga    120
aggcgggata ataagaaca ctttactgat aaattgtcat gttttttttt taaaaacatc     180
tgctacacat catgaaacag gaatgtggtt ttggtgttag cgcttctcac gaaataaatg     240
acttagtcag gggaaaatgt tgtaaccgcg gtacacactg acctttaact ttatgagaaa     300
aacaggaact gcggttgctc tgttagcaga ttttagggtt ctcgttagcc tgggtaggaa     360
agaccccaac cacagtaccc actaaccttt aacttaatga gaaaaacagg aactgcggtt     420
gcttcgttag cagttttag agttttaatt cgcatgaaca ggaaagactt caaccgcaat     480
atctgctaat ttttaacttt ataagaaaaa caggaactgc ggttgccgcg ttagcagctt     540
ttagagttct cattcgcctg gcaggaaat acttcaaccg cggtacccgc tgatctttaa     600
atttatgaga aaaacaggaa ctgcgattgc cgcgttagca gcttttagag ttctcattcg     660
cctggacagg aaatacttca accgcggtac ccgctgatct ttaactttat gggaaaaaca     720
ggaactgcgg ttgccgcgtt agcagctttt agagttctca ttcgcctggg caggaaatac    780
ttcaaccgcg gtacccgctg atctttaact ttatga                                816

<210> SEQ ID NO 18
<211> LENGTH: 576
<212> TYPE: DNA
<213> ORGANISM: Artificial
<220> FEATURE:
<223> OTHER INFORMATION: sequence of 9u-d1-4 in EXAMPLE 1

<400> SEQUENCE: 18
acttagtcag gggaaaatgt tgtaaccgcg gtacacactg acctttaact ttatgagaaa      60
aacaggaact gcggttgctc tgttagcaga ttttagggtt ctcgttagcc tgggtaggaa    120
agaccccaac cacagtaccc actaaccttt aacttaatga gaaaaacagg aactgcggtt    180
gcttcgttag cagttttag agttttaatt cgcatgaaca ggaaagactt caaccgcaat     240
atctgctaat ttttaacttt ataagaaaaa caggaactgc ggttgccgcg ttagcagctt     300
ttagagttct cattcgcctg gcaggaaat acttcaaccg cggtacccgc tgatctttaa     360
atttatgaga aaaacaggaa ctgcgattgc cgcgttagca gcttttagag ttctcattcg     420
```

```
cctggacagg aaatacttca accgcggtac ccgctgatct ttaactttat gggaaaaaca    480
ggaactgcgg ttgccgcgtt agcagctttt agagttctca ttcgcctggg caggaaatac    540
ttcaaccgcg gtacccgctg atctttaact ttatga                              576
```

<210> SEQ ID NO 19
<211> LENGTH: 429
<212> TYPE: DNA
<213> ORGANISM: Artificial
<220> FEATURE:
<223> OTHER INFORMATION: sequence of 9u-d1-5 in EXAMPLE 1

<400> SEQUENCE: 19

```
tttaacttaa tgagaaaaac aggaactgcg gttgcttcgt tagcagtttt tagagttta     60 attcgcatga acaggaaaga cttcaaccgc aatatctgct aattttttaac tttataagaa   120 aaacaggaac tgcggttgcc gcgttagcag cttttagagt tctcattcgc ctgggcagga   180
aatacttcaa ccgcggtacc cgctgatctt taaatttatg agaaaaacag gaactgcgat   240
tgccgcgtta gcagctttta gagttctcat tcgcctggac aggaaatact tcaaccgcgg   300
tacccgctga tctttaactt tatgggaaaa acaggaactg cggttgccgc gttagcagct   360
tttagagttc tcattcgcct gggcaggaaa tacttcaacc gcggtacccg ctgatcttta   420
actttatga                                                            429
```

<210> SEQ ID NO 20
<211> LENGTH: 352
<212> TYPE: DNA
<213> ORGANISM: Artificial
<220> FEATURE:
<223> OTHER INFORMATION: sequence of 9u-d1-7 in EXAMPLE 1

<400> SEQUENCE: 20

```
agacttcaac cgcaatatct gctaattttt aactttataa gaaaaacagg aactgcggtt    60
gccgcgttag cagcttttag agttctcatt cgcctgggca ggaaatactt caaccgcggt   120
acccgctgat ctttaaattt atgagaaaaa caggaactgc gattgccgcg ttagcagctt   180
ttagagttct cattcgcctg acaggaaat acttcaaccg cggtacccgc tgatctttaa   240
ctttatggga aaaacaggaa ctgcggttgc cgcgttagca gcttttagag ttctcattcg   300
cctgggcagg aaatacttca accgcggtac ccgctgatct ttaactttat ga           352
```

<210> SEQ ID NO 21
<211> LENGTH: 278
<212> TYPE: DNA
<213> ORGANISM: Artificial
<220> FEATURE:
<223> OTHER INFORMATION: sequence of 9u-d3-7 in EXAMPLE 1

<400> SEQUENCE: 21

```
ttttagagtt ctcattcgcc tgggcaggaa atacttcaac cgcggtaccc gctgatcttt    60
aaatttatga gaaaaacagg aactgcgatt gccgcgttag cagcttttag agttctcatt   120
cgcctggaca ggaaatactt caaccgcggt acccgctgat ctttaacttt atgggaaaaa   180
caggaactgc ggttgccgcg ttagcagctt ttagagttct cattcgcctg gcaggaaat   240 acttcaaccg cggtacccgc tgatctttaa ctttatga                            278
```

<210> SEQ ID NO 22
<211> LENGTH: 242
<212> TYPE: DNA
<213> ORGANISM: Artificial
<220> FEATURE:

<223> OTHER INFORMATION: sequence of 9u-d5 in EXAMPLE 1

<400> SEQUENCE: 22

```
caaccgcggt acccgctgat ctttaaattt atgagaaaaa caggaactgc gattgccgcg      60
ttagcagctt ttagagttct cattcgcctg gacaggaaat acttcaaccg cggtacccgc     120
tgatctttaa ctttatggga aaaacaggaa ctgcggttgc cgcgttagca gcttttagag     180
ttctcattcg cctgggcagg aaatacttca accgcggtac ccgctgatct ttaactttat     240
ga                                                                    242
```

<210> SEQ ID NO 23
<211> LENGTH: 214
<212> TYPE: DNA
<213> ORGANISM: Artificial
<220> FEATURE:
<223> OTHER INFORMATION: sequence of 9u-d6 in EXAMPLE 1

<400> SEQUENCE: 23

```
ttatgagaaa aacaggaact gcgattgccg cgttagcagc ttttagagtt ctcattcgcc      60
tggacaggaa atacttcaac cgcggtaccc gctgatcttt aactttatgg gaaaaacagg     120
aactgcggtt gccgcgttag cagcttttag agttctcatt cgcctgggca ggaaatactt     180
caaccgcggt acccgctgat ctttaacttt atga                                 214
```

<210> SEQ ID NO 24
<211> LENGTH: 118
<212> TYPE: DNA
<213> ORGANISM: Artificial
<220> FEATURE:
<223> OTHER INFORMATION: sequence of 9u-d7 in EXAMPLE 1

<400> SEQUENCE: 24

```
ctttaacttt atgggaaaaa caggaactgc ggttgccgcg ttagcagctt ttagagttct      60
cattcgcctg ggcaggaaat acttcaaccg cggtacccgc tgatctttaa ctttatga      118
```

<210> SEQ ID NO 25
<211> LENGTH: 79
<212> TYPE: DNA
<213> ORGANISM: Artificial
<220> FEATURE:
<223> OTHER INFORMATION: sequence of 9u-d8 in EXAMPLE 1

<400> SEQUENCE: 25

```
gttagcagct tttagagttc tcattcgcct gggcaggaaa tacttcaacc gcggtacccg      60
ctgatcttta actttatga                                                   79
```

<210> SEQ ID NO 26
<211> LENGTH: 515
<212> TYPE: DNA
<213> ORGANISM: Artificial
<220> FEATURE:
<223> OTHER INFORMATION: sequence of 7MIEP(-493) in EXAMPLE 2

<400> SEQUENCE: 26

```
cgcagttcct gttgttttca catattaaaa tgttagtggg ttatgtggtt ggggtctttc      60
ctgcctaaac gggtgagaac ccgtaaaacc tgctgagaag caaccgcag ttcctgttgt     120
tttcacgggt ttaaatgtca gtgggttatg tggttggggt ctttcctgcc taaagcgagt     180
gggaatgtgt agaacttgct gagaagacaa ccgcaattcc tgttgtttca agatttaaa     240
taccaattcg aaataaaata accgcaaaaa tcatgtttac gtaaaatata aatccattgt     300
```

```
ggtttttatt ggaaaaataa tattttaaaa aaatacatgt acaaataagg ttaaaccctg       360 attttttag tattataatt ttttggcttt ttttaattgg ttgatatatt aacgtcattt       420
tcctgtgcat cacatccgct tcaaaatgta tataataaga agacagatca actattttgc      480 cacttttct tcaagagctt gaagatacag ttctg                                  515
```

<210> SEQ ID NO 27
<211> LENGTH: 410
<212> TYPE: DNA
<213> ORGANISM: Artificial
<220> FEATURE:
<223> OTHER INFORMATION: sequence of 7MIEP(-388) in EXAMPLE 2

<400> SEQUENCE: 27

```
cgcagttcct gttgttttca cgggtttaaa tgtcagtggg ttatgtggtt ggggtctttc       60
ctgcctaaag cgagtgggaa tgtgtagaac ttgctgagaa gacaaccgca attcctgttg      120
tttcaaagat ttaaatacca attcgaaata aaataaccgc aaaaatcatg ttacgtaaa      180 atataaatcc attgtggttt ttattggaaa aataatattt taaaaaaata catgtacaaa     240
taaggttaaa ccctaatttt tttagtatta taatttttg ctttttta attggttgat       300 atattaacgt cattttcctg tgcatcacat ccgcttcaaa atgtatataa taagaagaca     360
gatcaactat tttgccactt tttcttcaag agcttgaaga tacagttctg                410
```

<210> SEQ ID NO 28
<211> LENGTH: 255
<212> TYPE: DNA
<213> ORGANISM: Artificial
<220> FEATURE:
<223> OTHER INFORMATION: sequence of 7MIEP(-233) in EXAMPLE 2

<400> SEQUENCE: 28

```
accgcaaaaa tcatgtttac gtaaaatata aatccattgt ggttttatt ggaaaaataa       60 tattttaaaa aaatacatgt acaaataagg ttaaaccctg atttttttag tattataatt     120
ttttggcttt ttttaattgg ttgatatatt aacgtcattt tcctgtgcat cacatccgct     180
tcaaaatgta tataataaga agacagatca actattttgc cacttttct tcaagagctt      240 gaagatacag ttctg                                                       255
```

<210> SEQ ID NO 29
<211> LENGTH: 500
<212> TYPE: DNA
<213> ORGANISM: Artificial
<220> FEATURE:
<223> OTHER INFORMATION: sequence of 7U95P(-484) in EXAMPLE 2

<400> SEQUENCE: 29

```
tgggttctca cccgtttagg caggaaacac ccagaccgca taacccactg acatttaaac       60
ccgtgaaaac aacaggaact gcggttgact tctcagcagg ttttatgggt tctcacccgt     120
ttaggtagga aagacccaga ccgcataacc cactaacatt ttaatatgtg aaaataaaca     180
ggaactgcgg ttatagtttc agtacattct agagattaca tcctgctaag gcgaaaaaca     240
ctttaaccgc aaaagccact gattttaaa cttgtgaaaa taacaggaaa ccacagaaac       300
gtcaggaaaa aaacgttgtt ttataattat gtccataaaa catgcaacat aatccaaacc      360
ggccaatgat ttttctgctt aaatgtaatt taaataattt attcatacgt aagttgttat     420
agccacgcct acgcagcaat gtatataagc agacaccgtc atttcgcagt tagtctgctg     480
gaaagcttgt gaagactaca                                                  500
```

<210> SEQ ID NO 30
<211> LENGTH: 395
<212> TYPE: DNA
<213> ORGANISM: Artificial
<220> FEATURE:
<223> OTHER INFORMATION: sequence of 7U95P(-379) in EXAMPLE 2

<400> SEQUENCE: 30

| | | | | | |
|---|---|---|---|---|---|
| tgggttctca | cccgtttagg | taggaaagac | ccagaccgca | taacccacta | acattttaat | 60 |
| atgtgaaaat | aaacaggaac | tgcggttata | gtttcagtac | attctagaga | ttacatcctg | 120 |
| ctaaggcgaa | aaacacttta | accgcaaaag | ccactgattt | ttaaacttgt | gaaataaca | 180 |
| ggaaaccaca | gaaacgtcag | gaaaaaaacg | ttgttttata | attatgtcca | taaacatgc | 240 |
| aacataatcc | aaaccggcca | atgatttttc | tgcttaaatg | taatttaaat | aatttattca | 300 |
| tacgtaagtt | gttatagcca | cgcctacgca | gcaatgtata | taagcagaca | ccgtcatttc | 360 |
| gcagttagtc | tgctggaaag | cttgtgaaga | ctaca | | | 395 |

<210> SEQ ID NO 31
<211> LENGTH: 320
<212> TYPE: DNA
<213> ORGANISM: Artificial
<220> FEATURE:
<223> OTHER INFORMATION: sequence of 7U95P(-304) in EXAMPLE 2

<400> SEQUENCE: 31

| | | | | | |
|---|---|---|---|---|---|
| ggaactgcgg | ttatagtttc | agtacattct | agagattaca | tcctgctaag | gcgaaaaaca | 60 |
| ctttaaccgc | aaaagccact | gatttttaaa | cttgtgaaaa | taacaggaaa | ccacagaaac | 120 |
| gtcaggaaaa | aaacgttgtt | ttataattat | gtccataaaa | catgcaacat | aatccaaacc | 180 |
| ggccaatgat | ttttctgctt | aaatgtaatt | taaataattt | attcatacgt | aagttgttat | 240 |
| agccacgcct | acgcagcaat | gtatataagc | agacaccgtc | atttcgcagt | tagtctgctg | 300 |
| gaaagcttgt | gaagactaca | | | | | 320 |

<210> SEQ ID NO 32
<211> LENGTH: 4818
<212> TYPE: DNA
<213> ORGANISM: Artificial
<220> FEATURE:
<223> OTHER INFORMATION: sequence of pGL3 Basic in EXAMPLE 2

<400> SEQUENCE: 32

| | | | | | |
|---|---|---|---|---|---|
| ggtaccgagc | tcttacgcgt | gctagcccgg | gctcgagatc | tgcgatctaa | gtaagcttgg | 60 |
| cattccggta | ctgttggtaa | agccaccatg | gaagacgcca | aaaacataaa | gaaaggcccg | 120 |
| gcgccattct | atccgctgga | agatggaacc | gctggagagc | aactgcataa | ggctatgaag | 180 |
| agatacgccc | tggttcctgg | aacaattgct | tttacagatg | cacatatcga | ggtggacatc | 240 |
| acttacgctg | agtacttcga | aatgtccgtt | cggttggcag | aagctatgaa | acgatatggg | 300 |
| ctgaatacaa | atcacagaat | cgtcgtatgc | agtgaaaact | ctcttcaatt | ctttatgccg | 360 |
| gtgttgggcg | cgttatttat | cggagttgca | gttgcgcccg | cgaacgacat | ttataatgaa | 420 |
| cgtgaattgc | tcaacagtat | gggcatttcg | cagcctaccg | tggtgttcgt | ttccaaaaag | 480 |
| gggttgcaaa | aaattttgaa | cgtgcaaaaa | aagctcccaa | tcatccaaaa | aattattatc | 540 |
| atggattcta | aaacggatta | ccagggattt | cagtcgatgt | acacgttcgt | cacatctcat | 600 |
| ctacctcccg | gttttaatga | atacgatttt | gtgccagagt | ccttcgatag | ggacaagaca | 660 |
| attgcactga | tcatgaactc | ctctggatct | actggtctgc | ctaaaggtgt | cgctctgcct | 720 |

-continued

```
catagaactg cctgcgtgag attctcgcat gccagagatc ctattttttgg caatcaaatc    780
attccggata ctgcgatttt aagtgttgtt ccattccatc acggttttgg aatgtttact    840
acactcggat atttgatatg tggatttcga gtcgtcttaa tgtatagatt tgaagaagag    900
ctgtttctga ggagccttca ggattacaag attcaaagtg cgctgctggt gccaacccta    960
ttctccttct tcgccaaaag cactctgatt gacaaatacg atttatctaa tttacacgaa   1020
attgcttctg gtggcgctcc cctctctaag gaagtcgggg aagcggttgc caagaggttc   1080
catctgccag gtatcaggca aggatatggg ctcactgaga ctacatcagc tattctgatt   1140
acacccgagg gggatgataa accgggcgcg gtcggtaaag ttgttccatt ttttgaagcg   1200
aaggttgtgg atctggatac cgggaaaacg ctgggcgtta atcaaagagg cgaactgtgt   1260
gtgagaggtc ctatgattat gtccggttat gtaaacaatc cggaagcgac caacgccttg   1320
attgacaagg atggatggct acattctgga gacatagctt actgggacga agacgaacac   1380
ttcttcatcg ttgaccgcct gaagtctctg attaagtaca aaggctatca ggtggctccc   1440
gctgaattgg aatccatctt gctccaacac cccaacatct tcgacgcagg tgtcgcaggt   1500
cttcccgacg atgacgccgg tgaacttccc gccgccgttg ttgttttgga gcacggaaag   1560
acgatgacgg aaaagagat cgtggattac gtcgccagtc aagtaacaac cgcgaaaaag   1620
ttgcgcggag gagttgtgtt tgtggacgaa gtaccgaaag gtcttaccgg aaaactcgac   1680
gcaagaaaaa tcagagagat cctcataaag gccaagaagg cggaaagat cgccgtgtaa   1740
ttctagagtc ggggcggccg gccgcttcga gcagacatga taagatacat tgatgagttt   1800
ggacaaacca aactagaat gcagtgaaaa aaatgcttta tttgtgaaat ttgtgatgct   1860
attgctttat ttgtaaccat tataagctgc aataaacaag ttaacaacaa caattgcatt   1920
cattttatgt ttcaggttca gggggaggtg tgggaggttt tttaaagcaa gtaaaacctc   1980
tacaaatgtg gtaaaatcga taaggatccg tcgaccgatg cccttgagag ccttcaaccc   2040
agtcagctcc ttccggtggg cgcggggcat gactatcgtc gccgcactta tgactgtctt   2100
ctttatcatg caactcgtag gacaggtgcc ggcagcgctc ttccgcttcc tcgctcactg   2160
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
aaaaggccag gaaccgtaaa aaggccgcgt tgctggcgtt tttccatagg ctccgccccc   2340
ctgacgagca tcacaaaaat cgacgctcaa gtcagaggtg gcgaaacccg acaggactat   2400
aaagatacca ggcgtttccc cctggaagct ccctcgtgcg ctctcctgtt ccgaccctgc   2460
cgcttaccgg atacctgtcc gcctttctcc cttcgggaag cgtggcgctt tctcatagct   2520
cacgctgtag gtatctcagt tcggtgtagg tcgttcgctc caagctgggc tgtgtgcacg   2580
aaccccccgt tcagcccgac cgctgcgcct tatccggtaa ctatcgtctt gagtccaacc   2640
cggtaagaca cgacttatcg ccactggcag cagccactgg taacaggatt agcagagcga   2700
ggtatgtagg cggtgctaca gagttcttga agtggtggcc taactacggc tacactagaa   2760
gaacagtatt tggtatctgc gctctgctga agccagttac cttcggaaaa agagttggta   2820
gctcttgatc cggcaaacaa accaccgctg gtagcggtgg tttttttgtt tgcaagcagc   2880
agattacgcg cagaaaaaaa ggatctcaag aagatccttt gatcttttct acggggtctg   2940
acgctcagtg gaacgaaaac tcacgttaag ggattttggt catgagatta tcaaaaagga   3000
tcttcaccta gatccttttta aattaaaaat gaagttttaa atcaatctaa agtatatatg   3060
agtaaacttg gtctgacagt taccaatgct taatcagtga ggcacctatc tcagcgatct   3120
```

-continued

| | |
|---|---|
| gtctatttcg ttcatccata gttgcctgac tccccgtcgt gtagataact acgatacggg | 3180 |
| agggcttacc atctggcccc agtgctgcaa tgataccgcg agaccacgc tcaccggctc | 3240 |
| cagatttatc agcaataaac cagccagccg gaagggccga gcgcagaagt ggtcctgcaa | 3300 |
| ctttatccgc ctccatccag tctattaatt gttgccggga agctagagta agtagttcgc | 3360 |
| cagttaatag tttgcgcaac gttgttgcca ttgctacagg catcgtggtg tcacgctcgt | 3420 |
| cgtttggtat ggcttcattc agctccggtt cccaacgatc aaggcgagtt acatgatccc | 3480 |
| ccatgttgtg caaaaaagcg gttagctcct tcggtcctcc gatcgttgtc agaagtaagt | 3540 |
| tggccgcagt gttatcactc atggttatgg cagcactgca taattctctt actgtcatgc | 3600 |
| catccgtaag atgcttttct gtgactggtg agtactcaac caagtcattc tgagaatagt | 3660 |
| gtatgcggcg accgagttgc tcttgcccgg cgtcaatacg ggataatacc gcgccacata | 3720 |
| gcagaacttt aaaagtgctc atcattggaa aacgttcttc ggggcgaaaa ctctcaagga | 3780 |
| tcttaccgct gttgagatcc agttcgatgt aacccactcg tgcacccaac tgatcttcag | 3840 |
| catcttttac tttcaccagc gtttctgggt gagcaaaaac aggaaggcaa atgccgcaa | 3900 |
| aaaagggaat aagggcgaca cggaaatgtt gaatactcat actcttcctt tttcaatatt | 3960 |
| attgaagcat ttatcagggt tattgtctca tgagcggata catatttgaa tgtatttaga | 4020 |
| aaaataaaca ataggggtt ccgcgcacat ttccccgaaa agtgccacct gacgcgccct | 4080 |
| gtagcggcgc attaagcgcg gcgggtgtgg tggttacgcg cagcgtgacc gctacacttg | 4140 |
| ccagcgccct agcgcccgct cctttcgctt tcttcccttc ctttctcgcc acgttcgccg | 4200 |
| gctttccccg tcaagctcta aatcggggc tccctttagg gttccgattt agtgctttac | 4260 |
| ggcacctcga ccccaaaaaa cttgattagg gtgatggttc acgtagtggg ccatcgccct | 4320 |
| gatagacggt ttttcgccct tgacgttgg agtccacgtt ctttaatagt ggactcttgt | 4380 |
| tccaaactgg aacaacactc aaccctatct cggtctattc ttttgattta aagggattt | 4440 |
| tgccgatttc ggcctattgg ttaaaaaatg agctgattta caaaaatttt aacgcgaatt | 4500 |
| ttaacaaaat attaacgctt acaatttgcc attcgccatt caggctgcgc aactgttggg | 4560 |
| aagggcgatc ggtgcgggcc tcttcgctat tacgccagcc caagctacca tgataagtaa | 4620 |
| gtaatattaa ggtacgggag gtacttggag cggccgcaat aaaatatctt tattttcatt | 4680 |
| acatctgtgt gttggttttt tgtgtgaatc gatagtacta acatacgctc tccatcaaaa | 4740 |
| caaaacgaaa caaaacaaac tagcaaaata ggctgtcccc agtgcaagtg caggtgccag | 4800 |
| aacatttctc tatcgata | 4818 |

<210> SEQ ID NO 33
<211> LENGTH: 48
<212> TYPE: DNA
<213> ORGANISM: Artificial
<220> FEATURE:
<223> OTHER INFORMATION: RNAi of HIV-1 gp41

<400> SEQUENCE: 33

| | |
|---|---|
| aataagacag ggcttggaaa gacactttcc aagccctgtc ttatttt | 48 |

<210> SEQ ID NO 34
<211> LENGTH: 48
<212> TYPE: DNA
<213> ORGANISM: Artificial
<220> FEATURE:
<223> OTHER INFORMATION: RNAi of HIV-1 tat

<400> SEQUENCE: 34

```
aagcatccag gaagtcagcc tacaaggctg acttcctgga tgcttttt                    48

<210> SEQ ID NO 35
<211> LENGTH: 46
<212> TYPE: DNA
<213> ORGANISM: Artificial
<220> FEATURE:
<223> OTHER INFORMATION: RNAi of HTLV-1 tax

<400> SEQUENCE: 35
gaacattggt gaggaaggca cagccttcct caccaatgtt cttttt                     46
```

PROMOTER FOR INTRODUCING A GENE INTO A LYMPHOCYTE OR BLOOD CELL AND APPLICATION THEREOF

This application is a divisional of U.S. patent application Ser. No. 11/991,637 filed on Jul. 16, 2008 which is a national stage application under 35 U.S.C. §371 of PCT Application No. PCT/JP2006/317574 filed on Sep. 5, 2006 which claims priority to Japanese Patent Application No. 2005-261366 filed on Sep. 8, 2005, all of which are incorporated in their entirety herein by reference.

TECHNICAL FIELD

The present invention is related to a promoter for introducing a gene into lymphocytes or blood cells, and the application thereof.

BACKGROUND ART

There has been a demand for the establishment of a technique for gene therapy on lymphoid cells in order to treat various diseases targeting lymphoid cells, e.g., human immunodeficiency virus (HIV) infection. However, no satisfactory vector system for introducing a desired gene into lymphoid cells has been developed.

Herpesvirus (HHV) is a generic term referring to viruses of the family Herpesviridae. Both human herpesvirus 6 and 7 (HHV-6 and HHV-7) are double-stranded DNA viruses of the subfamily β Herpesviridae of the family Herpesviridae, which are responsible for exanthem subitum. (Yamanishi K. et al., "Identification of human herpesvirus 6 as a casual agent for exanthem subitum", Lancet 1988; i: 1065-1067 and Tanaka K. et al., "Human herpesvirus 7: Another casual agent for roseola (exanthem subitum)", J. pediatr., 1994; 125: 1-5) HHV-6 includes two strains, HHV-6A and HHV-6B. HHV-6 causes a viral infectious disease which often occurs during infancy and induces sudden high fever and exanthema before and after the reduction of fever. Its prognosis is generally good. HHV-7 infection tends to occur later than HHV-6 infection (Tanaka K. et al., "Seroepidemiological study of human herpesvirus-6 and -7 in children of different ages and detection of those two viruses in throat swabs by polymerase chain reaction", Journal of Medical Virology, 1996; 48: 88-94). Therefore, exanthem subitum caused by HHV-7 is clinically experienced as second exanthem subitum. A seroepidemiological study of HHV-6 and HHV-7 demonstrated that most children become positive for antibodies for HHV-6 and HHV-7 before the age of two or three. It has been reported that the inapparent infection rate is 20 to 40%.

HHV-7 is a herpesvirus which was newly found by Frenkel et al. in 1990 when a cytopathic effect occurred during culturing of CD4$^+$ T lymphoid cells of a healthy person's peripheral blood (Frankel N. et al., "Isolation of a new herpesvirus from human CD4$^+$ T cells", ProNAS USA, 87: 749-752, ProNAS USA, 87: 749-752, 1990). The virus was isolated from mononuclear cells of human peripheral blood. Both HHV-6 and -7 are CD4$^+$ T lymphoid cell tropic viruses. HHV-7 infects the cell via a CD4 receptor on the cell. HHV-7 can grow only in human T lymphoid cells. Therefore, HHV-7 is a virus which can be used for gene modification of human T lymphoid cells.

The HHV-7 genome is double-stranded DNA of about 145 kbp. The whole base sequence has been determined by Nicholas et al. It is known that at least 101 genes are present on the genome (John N. et al., Journal of Virology, September 1996, 5975 to 5989).

However, with respect to these HHVs, no detailed analysis has been conducted so far regarding the promoter activity thereof. Moreover, what is lymphoid cell specific for the viruses was due to the interaction with receptors in the cells, and the life cycle in which the viruses can only be propagated in human T-lymphocytes.

In addition, it is believed that these viruses, particularly HHV-7 virus, have no adverse effect on healthy persons. If a gene containing an antigenic determinant of various viruses (e.g., mumps) is incorporated into the viral genome of HHV-7 and is expressed in HHV-7, HHV-7 is considered to be useful as a vaccine. However, when HHV-7 is used as a vaccine, it is not preferable that the genotype is changed as the virus is subcultured, in terms of quality control and quality assurance. Therefore, when the recombinant virus is used as a vaccine, it is necessary to stably supply a virus derived from a single recombinant genotype virus. For this purpose, a technique for producing a HHV-7 recombinant virus having a single genotype has been desired.

In addition, the mutual relationship between the HIV infection of a T lymphoid cell strain SupT1 cell and a T lymphoid cell tropic human herpesvirus (HHV-6A (U1102 strain), HHV-7 (MRK, MSO strains)) has been studied. The HHV-7 strain, which is bound by a CD4 receptor of cells, exhibits satisfactory growth in SupT1 cells. However, infection could not been established for SupT1/HIV cells. In contrast, it has been recognized that the HHV-6A strain infects HIV-persistent infection SupT1 (SupT1/HIV) cells and exhibits clear CPE (Masao Yamada et al., "HIV Jizokukansen SupT1 Saibo heno HHV-6 oyobi-7 Choufukukannsen no Kokoromi (Attempt for HHV-6 and -7 Superinfection to HIV Persistent Infection Sup-T1 Cell)", Title No. 122, Titles and Abstracts of the 7th Annual Meeting of the Japanese Society for AIDS Research, 1993, Tokyo).

An ideal HIV vaccine can provide perfect and long-term protection from all types of HIV. On the other hand, conventional inactivated HIV vaccines have advantages and disadvantages, some of which will be described below. A method for producing a recombinant vaccine employs common techniques. However, since it is difficult to maintain immunogenicity (since immunogenicity is low), high antigenic load and frequent inoculation of an adjuvant are required. Safety is the greatest concern. A subunit vaccine containing either a native or recombinant subunit may be safe. However, such a subunit vaccine requires high antigen load and frequent vaccination with adjuvant, because of the use of a subunit and the low immunogenicity. Moreover, safety is the most important issue. Furthermore, subunit vaccines comprising either a native or a recombinant subunit may be safe, however, they are subjected to limitation due to low selectivity and low immunogenicity of the subunit, thereby they allow development of usable vaccines for treating an immune responsible cell such as HIV vaccines and the like.

[non-patent literature 1] Yamanishi K et al., "Identification of human herpesvirus 6 as a casual agent for exanthem subitum." Lancet 1988; i: pp. 1065-1067

[non-patent literature 2] Tanaka K et al., "Human herpesvirus 7: Another casual agent for roseola (exanthem subitum)" J pediatr. 1994; 125: pp. 1-5

[non-patent literature 3] Tanaka-Taya K et al., "Seroepidemiological study of human herpesvirus-6 and -7 in children of different ages and detection of those two viruses in throat swabs by polymerase chain reaction" Journal of Medical Virology. 1996; 48: pp. 88-94

[non-patent literature 4] Frankel N et al., "Isolation of a new herpesvirus from human CD4+T cells." ProNAS USA 87:749-752, ProNAS USA 87:749-752, 1990

[non-patent literature 5] John N. et al., Journal of Virology, Sep. 1996, pp. 5975-5989

[non-patent literature 6] Masao Yamada et al., "HIV Jizoku-kansen SupT1 Saibo heno HHV-6 oyobi -7 Choufuku-kannsen no Kokoromi (Attempt for HHV-6 and -7 Super-infection to HIV Persistent Infection Sup-T1 Cell)", Title No. 122, Titles and Abstracts of the 7th Annual Meeting of the Japanese Society for AIDS Research, 1993, Tokyo

DISCLOSURE OF THE INVENTION

Problem to be Solved by the Invention

It is an object of the present invention to provide a promoter which induces gene expression in an immune system cell or blood cell such as lymphoid cells, in a selective and potent manner.

Means for Solving the Problem

The above mentioned problems have been solved by the present invention by discovering that MIE promoter of HHV6, MIE promoter of HHV67, m and U95 promoter of HHV7 surprisingly induce specific expression in an immune responsible cell such as T lymphoid cell, or hemocyto-lineage cells.

In development of DNA vaccines, which are an attractive new technology, potent expression promoters are essential. To date, human cytomegalovirus (HCMV) immediate early (IE) promoter is widely used in DNA vaccines. This is due to the fact that HCMV IE promoters are believed to exhibit potent activity in a variety of cells in general. However, it is reported that the expression efficiency thereof is low in lymphoid lineage cells, and the phenomenon of inactivation due to methylation and the like is observed. Moreover, there are problems associated with a variety of restrictions which inhibit realization of the application of the HHV IE promoter on DNA vaccines.

HCMV is known to have a limited number of cells which it can infect, but is known to infect fibroblast cells and blood endothelial cells and the like. On the other hand, HHV-6 infects human infants and causes exanthema subitum or roseola infantum, and it is known that it proliferates well in human lymphocytes, in particular, T cells. The present inventors have elucidated in the present invention that major immediate early gene '(MIE) of HHV-6, which belongs to the same β virus subgenus of the human herpesvirus genus, the same as HCMV, exhibits strong promoter activity. The present inventors have also elucidated that the MIE gene promoter is available for DNA vaccines. HHV-7 is also a CD4$^+$ T lymphocyte directed virus, and the promoter thereof can be used to develop DNA vaccines, for example, to prevent or treat a disease related to CD4$^+$ T lymphocytes. The present inventors have elucidated in the present invention the utility of HHV 7 MIE promoter and HHV 7 U95 promoter, and thus also elucidated that these promoters can be used for DNA vaccines.

Therefore, the present invention provides the following:

(1) An MIE promoter of HHV6B.

(2) The promoter according to item 1, which comprises at least eight contiguous nucleotides of the sequence set forth in SEQ ID NO: 1.

(3) The promoter according to item 1, which comprises at least the R3 region of the sequence set forth in SEQ ID NO: 1 or a functional variant thereof.

(4) The promoter according to item 1, which comprises at least the sequence of −574 to −427 (SEQ ID NO: 13) from the transcription initiation point of the SEQ ID NO: 1.

(5) The promoter according to item 1, which comprises at least the sequence of −1051 to −427 (SEQ ID NO: 14) from the transcription initiation point of SEQ ID NO: 1.

(6) The promoter according to item 1, which comprises a motif of NF-κB and a motif of AP-1.

(7) The promoter according to item 1, which comprises the sequence set forth in SEQ ID NO: 1.

(8) The promoter according to item 1, wherein the promoter comprises: (a) a polynucleotide having the base sequence set forth in SEQ ID NO: 1, or the base sequence corresponding thereto or a fragment sequence thereof;
(b) a polynucleotide of an allelic variant of the base sequence set forth in SEQ ID NO: 1 or the base sequence corresponding thereto or a fragment sequence thereof;
(c) a polynucleotide which hybridizes a polynucleotide of any of (a) or (b) and has a biological activity thereof; or
(d) a polynucleotide which consists of the base sequence of any of (a) to (c) or a complement sequence thereof with at least 70% identity, and has a biological activity thereof.

(9) The promoter according to item 1, which is at least 10 contiguous nucleotides in length.

(10) The promoter according to item 8, wherein the biological activity is the promoter activity.

(11) A nucleic acid construct comprising the promoter according to item 1.

(12) The nucleic acid construct according to Item 11, which comprises a sequence encoding a foreign gene which is not related to the promoter but is operatively linked to the sequence of the promoter.

(13) The nucleic acid construct according to item 12, wherein the foreign gene encodes an RNAi molecule, a drug, a recessive gene to be deleted, or a selective marker.

(14) The nucleic acid construct according to item 13, wherein the selective marker allows selection in a medium of a host in which the nucleic acid construct is introduced.

(15) The nucleic acid construct according to item 13, wherein the selective marker allows visual selection in a host in which the nucleic acid construct is introduced.

(16) The nucleic acid construct according to item 13, wherein the selective marker comprises hypoxanthine guanine phosphoribosyl transferase (hprt) or a fluorescent marker selected from the group consisting of green fluorescent protein (GFP), cyan fluorescent protein (CFP), yellow fluorescent protein (YFP) and red fluorescent protein (dsRed).

(17) The nucleic acid construct according to item 13, wherein the selective marker does not substantially exhibit toxicity against the host in which the nucleic acid construct is introduced.

(18) The nucleic acid construct according to item 13, wherein the recessive gene to be deleted is selected from the group consisting of ADA gene, PNP gene, γ c chain gene, TAP gene, MHC II gene, X-linked WASP, CD40 ligand, PI3K-like gene and DNA helicase.

(19) The nucleic acid construct according to item 13, wherein the drug is selected from the group consisting of a cytokine, a chemokine, a growth factor, a protein hormone, and a peptide hormone (e.g. interferon (IFN)-α, IFN-γ, interleukin [IL]-2, IL-12, granulocyte colony stimulating factor [G-CSF], granulocyte macrophage colony stimulating factor [GM-CSF]).

(20) The nucleic acid construct according to item 12, wherein the promoter induces specific expression of the foreign gene in a hemocyto-lineage cell, in particular, in a T cell.

(21) An expression vector comprising the nucleic acid construct according to item 11.

(22) A cell comprising the nucleic acid construct according to item 11.

(23) The cell according to item 22, wherein the cell is heterogenous to the promoter sequence.

(24) A tissue comprising the nucleic acid construct according to item 11.

(25) An organ comprising the nucleic acid construct according to item 11.

(26) An organism comprising the nucleic acid construct according to item 11.

(27) A pharmaceutical composition comprising the promoter according to item 1 and a sequence encoding an antigen.

(28) The pharmaceutical composition according to item 27, which is a DNA vaccine.

(29) A pharmaceutical composition for treating a disease, disorder or condition in which a lymphocyte-specific treatment is desired, which comprises the promoter according to item 1, and a nucleic acid sequence for the treatment.

(30) The pharmaceutical composition according to item 29, wherein the nucleic acid sequence for the treatment comprises a sequence selected from the group consisting of those encoding cytokines, chemokines, growth factors, protein hormones, peptide hormones, ribozymes and RNAis

```
(HIV-1 gp41:
                                          (SEQ ID NO: 33)
AATAAGACAGGGCTTGGAAAGACACTTTCCAAGCCCTGTCTTATTTTT/

HIV-1 tat:
                                          (SEQ ID NO: 34)
AAGCATCCAGGAAGTCAGCCTACAAGGCTGACTTCCTGGATGCTTTTT/

HTLV-1 tax:
                                          (SEQ ID NO: 35)
GAACATTGGTGAGGAAGGCACAGCCTTCCTCACCAATGTTCTTTTT).
```

(31) A method for expressing a protein in a lymphocyte specific manner, comprising the steps of:

A) preparing a nucleic acid construct in which the promoter according to item 1 is operatively linked to a nucleic acid sequence encoding the protein; and B) placing the nucleic acid construct under a condition in which the promoter induces the expression of the nucleic acid sequence encoding the protein.

(32) A kit for expressing a protein in a lymphocyte specific manner, comprising:

A) a nucleic acid construct in which the promoter according to item 1 is operatively linked to a nucleic acid sequence encoding the protein; and B) means for placing the nucleic acid construct under a condition in which the promoter induces the expression of the nucleic acid sequence encoding the protein.

(33) A kit for expressing a protein in a lymphocyte specific manner, comprising:

A) the promoter according to item 1; and

B) means for producing a nucleic acid construct in which the promoter is linked to a nucleic acid sequence encoding the protein.

(34) A method for treating or preventing a disease, disorder or condition which requires the expression of a protein in a lymphocyte specific manner, comprising the steps of:

A) producing a nucleic acid construct in which the promoter according to item 1 is linked to a nucleic acid sequence encoding the protein; and B) placing the nucleic acid construct under a condition in which the promoter induces the expression of the nucleic acid sequence encoding the protein.

(35) A kit for treating or preventing a disease, disorder or condition which requires the expression of a protein in a lymphocyte specific manner, comprising:

A) a nucleic acid construct in which the promoter according to item 1 is linked to a nucleic acid sequence encoding the protein; and B) means for placing the nucleic acid construct under a condition in which the promoter induces the expression of the nucleic acid sequence encoding the protein.

(36) A kit for treating or preventing a disease, disorder or condition which requires the expression of a protein in a lymphocyte specific manner, comprising:

A) the promoter according to item 1; and

B) means for producing a nucleic acid construct in which the promoter is linked to a nucleic acid sequence encoding the protein.

(37) A method for producing a protein, comprising the steps of:

A) preparing a nucleic acid construct in which the promoter according to item 1 is linked to a nucleic acid sequence encoding the protein; and B) placing the nucleic acid construct under a condition in which the promoter induces the expression of the nucleic acid sequence encoding the protein.

(38) A kit for producing a protein, comprising:

A) a nucleic acid construct in which the promoter according to item 1 is linked to a nucleic acid sequence encoding the protein; and B) means for placing the nucleic acid construct under a condition in which the promoter induces the expression of the nucleic acid sequence encoding the protein.

(39) A kit for producing a protein, comprising:

A) the promoter according to item 1; and

B) means for producing a nucleic acid construct in which the promoter is linked to a nucleic acid sequence encoding the protein.

(40) Use of the promoter according to item 1, for manufacture of a pharmaceutical composition for treating or preventing a disease, disorder or condition which requires the expression of a protein in a lymphocyte specific manner.

(41) An MIE promoter of HHV7.

(42) The promoter according to item 41, which comprises at least eight contiguous nucleotides of the sequence set forth in SEQ ID NO: 2.

(43) The promoter according to item 41, which comprises at least the R2 region of the sequence set forth in SEQ ID NO: 2 or a functional variant thereof.

(44) The promoter according to item 41, which comprises at least the sequence of +22 to −233 of the SEQ ID NO: 2.

(45) The promoter according to item 41, which comprises at least the sequence of +22 to −388 of the SEQ ID NO: 2.

(46) The promoter according to item 41, which comprises a motif of NF-κB present in the R2 region.

(47) The promoter according to item 41, which comprises the sequence set forth in SEQ ID NO: 15.

(48) The promoter according to item 41, wherein the promoter comprises:

(a) a polynucleotide having the base sequence set forth in SEQ ID NO. 2, or a base sequence corresponding thereto or a fragment sequence thereof;

(b) a polynucleotide of an allelic variant of the base sequence set forth in SEQ ID NO. 2 or the base sequence corresponding thereto or a fragment sequence thereof;

(c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof.

(49) The promoter according to item 41, which is at least 10 contiguous nucleotides in length.

(50) The promoter according to item 48, wherein the biological activity is the promoter activity.

(51) A nucleic acid construct comprising the promoter according to item 41.

(52) The nucleic acid construct according to Item 51, which comprises a sequence encoding a foreign gene which is not related to the promoter but is operatively linked to the sequence of the promoter.

(53) The nucleic acid construct according to item 52, wherein the foreign gene encodes an RNAi molecule, a drug, a recessive gene to be deleted, or a selective marker.

(54) The nucleic acid construct according to item 53, wherein the selective marker allows selection in a medium of a host in which the nucleic acid construct is introduced.

(55) The nucleic acid construct according to item 53, wherein the selective marker allows visual selection in a host in which the nucleic acid construct is introduced.

(56) The nucleic acid construct according to item 53, wherein the selective marker comprises hypoxanthine guanine phosphoribosyl transferase (hprt) or a fluorescent marker selected from the group consisting of green fluorescent protein (GFP), cyan fluorescent protein (CFP), yellow fluorescent protein (YFP) and red fluorescent protein (dsRed).

(57) The nucleic acid construct according to item 53, wherein the selective marker does not substantially exhibit toxicity against the host in which the nucleic acid construct is introduced.

(58) The nucleic acid construct according to item 53, wherein the recessive gene to be deleted is selected from the group consisting of ADA gene, PNP gene, γ c chain gene, TAP gene, MHC II gene, X-linked WASP, CD40 ligand, PI3K-like gene and DNA helicase.

(59) The nucleic acid construct according to item 53, wherein the drug is selected from the group consisting of a cytokine, a chemokine, a growth factor, a protein hormone, and a peptide hormone (IFN-α, IFN-γ, IL-2, IL-12, G-CSF, GM-CSF).

(60) The nucleic acid construct according to item 52, wherein the promoter induces specific expression of the foreign gene in a hemocyto-lineage cell, in particular, in a T cell.

(61) An expression vector comprising the nucleic acid construct according to item 51.

(62) A cell comprising the nucleic acid construct according to item 51.

(63) The cell according to item 62, wherein the cell is heterogenous to the promoter sequence.

(64) A tissue comprising the nucleic acid construct according to item 51.

(65) An organ comprising the nucleic acid construct according to item 51.

(66) An organism comprising the nucleic acid construct according to item 51.

(67) A pharmaceutical composition comprising the promoter according to item 41 and a sequence encoding an antigen.

(68) The pharmaceutical composition according to item 67, which is a DNA vaccine.

(69) A pharmaceutical composition for treating a disease, disorder or condition in which a lymphocyte-specific treatment is desired, which comprises the promoter according to item 41, and a nucleic acid sequence for the treatment.

(70) The pharmaceutical composition according to item 69, wherein the nucleic acid sequence for the treatment comprises a sequence selected from the group consisting of those encoding cytokines, chemokines, growth factors, protein hormones, peptide hormones, ribozymes and RNAis

```
(HIV-1 gp41:
                                         (SEQ ID NO: 33)
AATAAGACAGGGCTTGGAAAGACACTTTCCAAGCCCTGTCTTATTTTT/

HIV-1 tat:
                                         (SEQ ID NO: 34)
AAGCATCCAGGAAGTCAGCCTACAAGGCTGACTTCCTGGATGCTTTTT/

HTLV-1 tax:
                                         (SEQ ID NO: 35)
GAACATTGGTGAGGAAGGCACAGCCTTCCTCACCAATGTTCTTTTT).
```

(71) A method for expressing a protein in a lymphocyte specific manner, comprising the steps of:
A) preparing a nucleic acid construct in which the promoter according to item 41 is operatively linked to a nucleic acid sequence encoding the protein; and
B) placing the nucleic acid construct under a condition in which the promoter induces the expression of the nucleic acid sequence encoding the protein.

(72) A kit for expressing a protein in a lymphocyte specific manner, comprising:
A) a nucleic acid construct in which the promoter according to item 41 is operatively linked to a nucleic acid sequence encoding the protein; and
B) means for placing the nucleic acid construct under a condition in which the promoter induces the expression of the nucleic acid sequence encoding the protein.

(73) A kit for expressing a protein in a lymphocyte specific manner, comprising:
A) the promoter according to item 41; and
B) means for producing a nucleic acid construct in which the promoter is linked to a nucleic acid sequence encoding the protein.

(74) A method for treating or preventing a disease, disorder or condition which requires the expression of a protein in a lymphocyte specific manner, comprising the steps of:
A) producing a nucleic acid construct in which the promoter according to item 41 is linked to a nucleic acid sequence encoding the protein; and
B) placing the nucleic acid construct under a condition in which the promoter induces the expression of the nucleic acid sequence encoding the protein.

(75) A kit for treating or preventing a disease, disorder or condition which requires the expression of a protein in a lymphocyte specific manner, comprising:
A) a nucleic acid construct in which the promoter according to item 41 is linked to a nucleic acid sequence encoding the protein; and
B) means for placing the nucleic acid construct under a condition in which the promoter induces the expression of the nucleic acid sequence encoding the protein.

(76) A kit for treating or preventing a disease, disorder or condition which requires the expression of a protein in a lymphocyte specific manner, comprising:
A) the promoter according to item 41; and
B) means for producing a nucleic acid construct in which the promoter is linked to a nucleic acid sequence encoding the protein.

(77) A method for producing a protein, comprising the steps of:

A) preparing a nucleic acid construct in which the promoter according to item 41 is linked to a nucleic acid sequence encoding the protein; and B) placing the nucleic acid construct under a condition in which the promoter induces the expression of the nucleic acid sequence encoding the protein.

(78) A kit for producing a protein, comprising:

A) a nucleic acid construct in which the promoter according to item 41 is linked to a nucleic acid sequence encoding the protein; and B) means for placing the nucleic acid construct under a condition in which the promoter induces the expression of the nucleic acid sequence encoding the protein.

(79) A kit for producing a protein, comprising:

A) the promoter according to item 41; and

B) means for producing a nucleic acid construct in which the promoter is linked to a nucleic acid sequence encoding the protein.

(80) Use of the promoter according to item 41, for manufacture of a pharmaceutical composition for treating or preventing a disease, disorder or condition which requires the expression of a protein in a lymphocyte specific manner.

(81) A U95 promoter of HHV7.

(82) The promoter according to item 81, which comprises at least eight contiguous nucleotides of the sequence set forth in SEQ ID NO: 12.

(83) The promoter according to item 81, which comprises at least the R2 region of the sequence set forth in SEQ ID NO: 12 or a functional variant thereof.

(84) The promoter according to item 81, which comprises at least the sequence of +16 to −233 of the SEQ ID NO: 12.

(85) The promoter according to item 81, which comprises at least the sequence of +16 to −379 of the SEQ ID NO: 12.

(86) The promoter according to item 81, which comprises a motif of NF-κB present in the R2 region.

(87) The promoter according to item 81, which comprises the sequence set forth in SEQ ID NO: 16.

(88) The promoter according to item 81, wherein the promoter comprises:

(a) a polynucleotide having the base sequence set forth in SEQ ID NO. 12, or the base sequence corresponding thereto or a fragment sequence thereof;

(b) a polynucleotide of an allelic variant of the base sequence set forth in SEQ ID NO. 12 or the base sequence corresponding thereto or a fragment sequence thereof;

(c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof.

(89) The promoter according to item 81, which is at least 10 contiguous nucleotides in length.

(90) The promoter according to item 88, wherein the biological activity is the promoter activity.

(91) A nucleic acid construct comprising the promoter according to item 81.

(92) The nucleic acid construct according to Item 91, which comprises a sequence encoding a foreign gene which is not related to the promoter but is operatively linked to the sequence of the promoter.

(93) The nucleic acid construct according to item 92, wherein the foreign gene encodes an RNAi molecule, a drug, a recessive gene to be deleted, or a selective marker.

(94) The nucleic acid construct according to item 93, wherein the selective marker allows selection in a medium of a host in which the nucleic acid construct is introduced.

(95) The nucleic acid construct according to item 93, wherein the selective marker allows visual selection in a host in which the nucleic acid construct is introduced.

(96) The nucleic acid construct according to item 93, wherein the selective marker comprises hypoxanthine guanine phosphoribosyl transferase (hprt) or a fluorescent marker selected from the group consisting of green fluorescent protein (GFP), cyan fluorescent protein (CFP), yellow fluorescent protein (YFP) and red fluorescent protein (dsRed).

(97) The nucleic acid construct according to item 93, wherein the selective marker does not substantially exhibit toxicity against the host in which the nucleic acid construct is introduced.

(98) The nucleic acid construct according to item 93, wherein the recessive gene to be deleted is selected from the group consisting of ADA gene, PNP gene, γ c chain gene, TAP gene, MHC II gene, X-linked WASP, CD40 ligand, PI3K-like gene and DNA helicase.

(99) The nucleic acid construct according to item 93, wherein the drug is selected from the group consisting of a cytokine, a chemokine, a growth factor, a protein hormone, and a peptide hormone (IFN-α, IFN-γ, IL-2, IL-12, G-CSF, GM-CSF).

(100) The nucleic acid construct according to item 92, wherein the promoter induces specific expression of the foreign gene in a hemocyto-lineage cell, in particular, in a T cell.

(101) An expression vector comprising the nucleic acid construct according to item 91.

(102) A cell comprising the nucleic acid construct according to item 91.

(103) The cell according to item 102, wherein the cell is heterogenous to the promoter sequence.

(104) A tissue comprising the nucleic acid construct according to item 91.

(105) An organ comprising the nucleic acid construct according to item 91.

(106) An organism comprising the nucleic acid construct according to item 91.

(107) A pharmaceutical composition comprising the promoter according to item 81 and a sequence encoding an antigen.

(108) The pharmaceutical composition according to item 107, which is a DNA vaccine.

(109) A pharmaceutical composition for treating a disease, disorder or condition in which a lymphocyte-specific treatment is desired, which comprises the promoter according to item 81, and a nucleic acid sequence for the treatment.

(110) The pharmaceutical composition according to item 109, wherein the nucleic acid sequence for the treatment comprises a sequence selected from the group consisting of those encoding cytokines, chemokines, growth factors, protein hormones, peptide hormones, ribozymes and RNAis

```
(HIV-1 gp41:
                                            (SEQ ID NO: 33)
AATAAGACAGGGCTTGGAAAGACACTTTCCAAGCCCTGTCTTATTTTT/

HIV-1 tat:
                                            (SEQ ID NO: 34)
AAGCATCCAGGAAGTCAGCCTACAAGGCTGACTTCCTGGATGCTTTTT/

HTLV-1 tax:
                                            (SEQ ID NO: 35)
GAACATTGGTGAGGAAGGCACAGCCTTCCTCACCAATGTTCTTTTT).
```

(111) A method for expressing a protein in a lymphocyte specific manner, comprising the steps of:
A) preparing a nucleic acid construct in which the promoter according to item 81 is operatively linked to a nucleic acid sequence encoding the protein; and
B) placing the nucleic acid construct under a condition in which the promoter induces the expression of the nucleic acid sequence encoding the protein.

(112) A kit for expressing a protein in a lymphocyte specific manner, comprising:
A) a nucleic acid construct in which the promoter according to item 81 is operatively linked to a nucleic acid sequence encoding the protein; and
B) means for placing the nucleic acid construct under a condition in which the promoter induces the expression of the nucleic acid sequence encoding the protein.

(113) A kit for expressing a protein in a lymphocyte specific manner, comprising:
A) the promoter according to item 81; and
B) means for producing a nucleic acid construct in which the promoter is linked to a nucleic acid sequence encoding the protein.

(114) A method for treating or preventing a disease, disorder or condition which requires the expression of a protein in a lymphocyte specific manner, comprising the steps of:
A) producing a nucleic acid construct in which the promoter according to item 81 is linked to a nucleic acid sequence encoding the protein; and
B) placing the nucleic acid construct under a condition in which the promoter induces the expression of the nucleic acid sequence encoding the protein.

(115) A kit for treating or preventing a disease, disorder or condition which requires the expression of a protein in a lymphocyte specific manner, comprising:
A) a nucleic acid construct in which the promoter according to item 81 is linked to a nucleic acid sequence encoding the protein; and
B) means for placing the nucleic acid construct under a condition in which the promoter induces the expression of the nucleic acid sequence encoding the protein.

(116) A kit for treating or preventing a disease, disorder or condition which requires the expression of a protein in a lymphocyte specific manner, comprising:
A) the promoter according to item 81; and
B) means for producing a nucleic acid construct in which the promoter is linked to a nucleic acid sequence encoding the protein.

(117) A method for producing a protein, comprising the steps of:
A) preparing a nucleic acid construct in which the promoter according to item 81 is linked to a nucleic acid sequence encoding the protein; and
B) placing the nucleic acid construct under a condition in which the promoter induces the expression of the nucleic acid sequence encoding the protein.

(118) A kit for producing a protein, comprising:
A) a nucleic acid construct in which the promoter according to item 81 is linked to a nucleic acid sequence encoding the protein; and
B) means for placing the nucleic acid construct under a condition in which the promoter induces the expression of the nucleic acid sequence encoding the protein.

(119) A kit for producing a protein, comprising:
A) the promoter according to item 81; and
B) means for producing a nucleic acid construct in which the promoter is linked to a nucleic acid sequence encoding the protein.

(120) Use of the promoter according to item 81, for manufacture of a pharmaceutical composition for treating or preventing a disease, disorder or condition which requires the expression of a protein in a lymphocyte specific manner.

Hereinafter, preferable embodiments of the present invention are presented. It should be understood that those skilled in the art would appropriately practice the embodiments thereof based on the description of the present invention in view of the well known and routinely used technology in the art, and the functions and effects attained by the present invention should be readily understood.

Effects of the Invention

The present invention provides promoters which selectively induce the expression of a protein in a cell of the immune system such as T lymphocytes. The promoters of the present invention are used to provide a method and medicament for effectively preventing or treating immunological disease such as innate immune deficiency syndrome and the like. The present invention also provides a technology in order to efficiently conduct gene therapy.

BRIEF DESCRIPTION OF SEQUENCE LISTING

Figure 1:
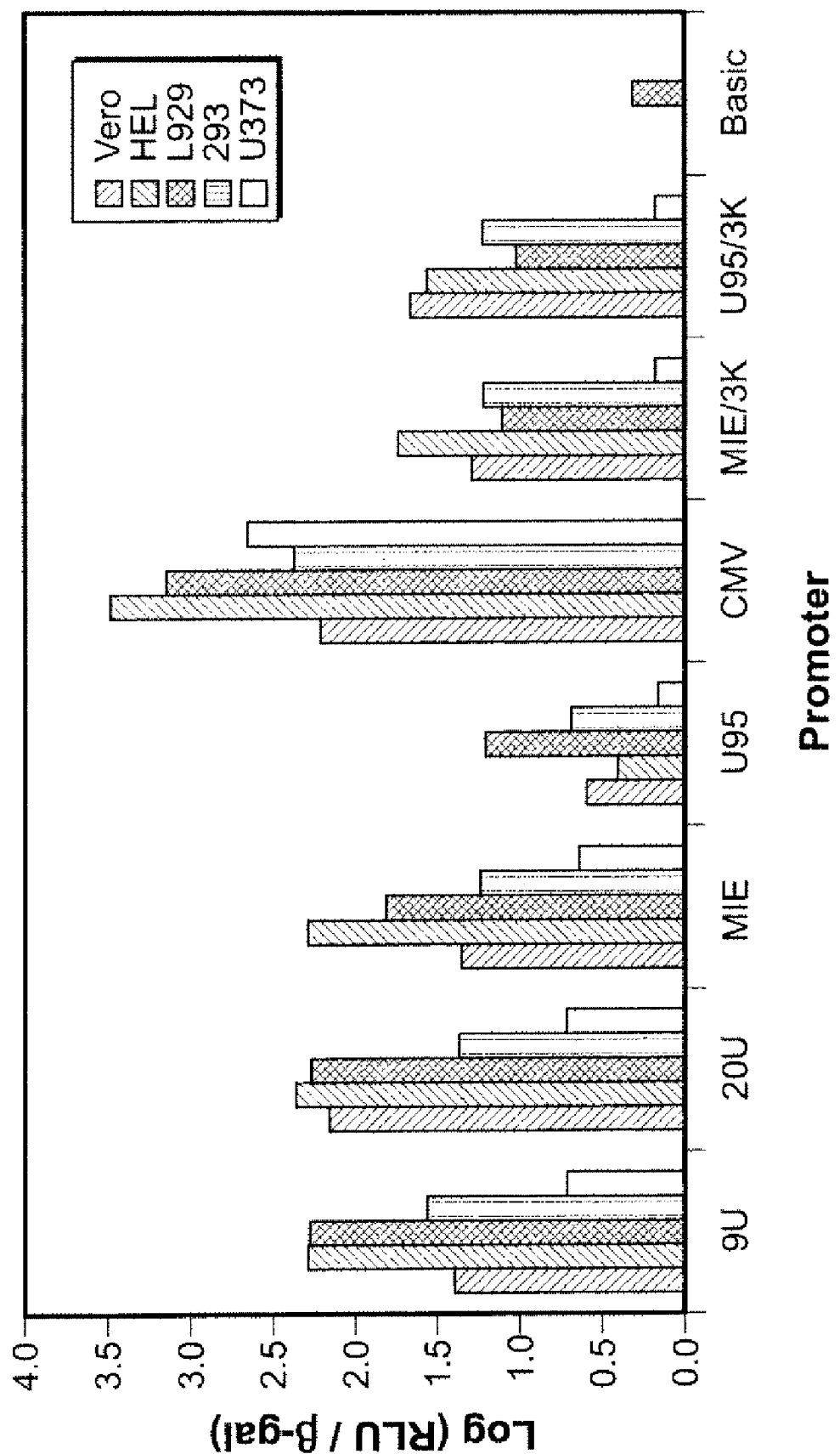
FIG. 1 depicts a comparison of promoter activities in adhesive cells. The x-axis aligns a variety of promoters, and the promoter activities of the Vero cell, the HEL cell, the L929 cell, the 293 cell and the 373 cell are shown using Log(RLU)/β-gal with logarithmic reference.

SEQ ID NO: 1 is the sequence of HHV6B MIE promoter.
SEQ ID NO: 2 is the sequence of HHV7 MIE promoter.
SEQ ID NO: 3 is the sequence of HHV6A MIE promoter.
SEQ ID NO: 4 is the sequence of HHV6B R3 region.
SEQ ID NO: 5 is the sequence of 20u used in Example 1.
SEQ ID NO: 6 is the sequence of 9u used in Example 1.
SEQ ID NO: 7 is the sequence of MIE used in Example 1.
SEQ ID NO: 8 is the sequence of U95 used in Example 1.
SEQ ID NO: 9 is the sequence of CMV used in Example 1.
SEQ ID NO: 10 is the sequence of MIE/3K used in Example 1.
SEQ ID NO: 11 is the sequence of U95/3K used in Example 1.
SEQ ID NO: 12 is the sequence of HHV7 U95 promoter
SEQ ID NO: 13 is the sequence of −574 to −427 from the transcription initiation site of HHV6B MIE.
SEQ ID NO: 14 is the sequence of −1051 to −427 from the transcription initiation site of HHV6B MIE.
SEQ ID NO: 15 is the sequence of +22 to −493 from the transcription initiation site of HHV7 MIE.
SEQ ID NO: 16 is the sequence of +16 to −484 from the transcription initiation site of HHV7 MIE.
SEQ ID NO: 17 is the sequence of 9u-d2-7 used in Example 1.
SEQ ID NO: 18 is the sequence of 9u-d1-4 used in Example 1.
SEQ ID NO: 19 is the sequence of 9u-d1-5 used in Example 1.
SEQ ID NO: 20 is the sequence of 9u-d1-7 used in Example 1.
SEQ ID NO: 21 is the sequence of 9u-d3-7 used in Example 1.
SEQ ID NO: 22 is the sequence of 9u-d5 used in Example 1.
SEQ ID NO: 23 is the sequence of 9u-d6 used in Example 1.
SEQ ID NO: 24 is the sequence of 9u-d7 used in Example 1.
SEQ ID NO: 25 is the sequence of 9u-d8 used in Example 1.
SEQ ID NO: 26 is the sequence of 7MIEP (−493) used in Example 2.
SEQ ID NO: 27 is the sequence of 7MIEP (−388) used in Example 2.
SEQ ID NO: 28 is the sequence of 7MIEP (−233) used in Example 2.
SEQ ID NO: 29 is the sequence of 7U95P (−484) used in Example 2.
SEQ ID NO: 30 is the sequence of 7U95P (−379) used in Example 2.
SEQ ID NO: 31 is the sequence of 7U95P (−304) used in Example 2.
SEQ ID NO: 32 is the sequence of pGL3 Basic used in Example 2.
SEQ ID NO: 33 is an example of RNAi of HIV-1 gp41.
SEQ ID NO: 34 is an example of RNAi of HIV-1 tat.
SEQ ID NO: 35 is an example of RNAi of HIV-1 tax.

BEST MODE FOR CARRYING OUT THE INVENTION

Hereinafter, the present invention will be described. It should be understood throughout the present specification that articles for singular forms (e.g., "a", "an", "the", etc. in English, and articles, adjectives, etc. in other languages) include plural referents unless the context clearly dictates otherwise. It should be also understood that the terms as used herein have definitions typically used in the art unless otherwise mentioned. Accordingly, unless otherwise defined, all terminology and technical terms used herein will have the same meanings as those generally understood by those skilled in the art belonging to the filed of the present invention. If there is contradiction, the present specification (including the definition) takes precedence.

DEFINITION OF TERMS

The definitions of terms used herein are described below.

As used herein the term "HHV" refers to a human herpes virus, of which there are types 1, 2, 3, 4, 5, 6, 7, 8 and the like.

As used herein, the term "herpesvirus" includes all of HHV-6A, HHV-6B, and HHV-7, and both their wild-types and recombinant types unless otherwise mentioned. As used herein, the term "HHV-6 (human herpes virus 6)" includes HHV-6A and HHV-6B, and both their wild-types and recombinant types unless otherwise mentioned. HHV6 belongs to the β subgenus as cytomegalovirus HHV-5, and HHV6B is a causative virus of exanthema subitum, and it is said that most Japanese will have been infected therewith by the age of two years old. As used herein, the term "HHV-7 (human herpes virus 7)" refers to any herpes virus belonging to this type of herpes virus. HHV7 is also said to be a causative body of exanthema subitum, however, in comparison to HHV6B, the occurrence thereof is lower, and the age where the patients are infected is older. As with HHV6, HHV7 belongs to the β subgenus, and it is also said that it is believed to infect CD4$^+$ cells, and thus cause the onset of pityriasis rosea Gibert, and it is also said that most Japanese will have been infected therewith by the age of two years old.

As used herein, the term "wild strain" in relation to herpesvirus refers to a herpesvirus strain which is not artificially modified and is isolated from nature. An example of a wild strain includes, but is not limited to, strain J1.

As used herein, the term "wild strain" in relation to HHV-6A refers to a HHV-6A strain which is not artificially modified and is isolated from nature. An example of a wild strain includes, but is not limited to, strain U1102.

As used herein, the term "mutant strain" refers to a herpesvirus strain which has a mutation due to mutagenesis, multiple subculturings or the like. Mutagenesis of a herpesvirus strain may be either random mutagenesis or site-specific mutagenesis.

As used herein, the term "wild strain" in relation to HHV-6B refers to a HHV-6B strain which is not artificially modified and is isolated from nature. An example of a wild strain includes, but is not limited to, strain HST.

The terms "protein", "polypeptide", "oligopeptide" and "peptide" as used herein have the same meaning and refer to an amino acid polymer having any length.

The terms "polynucleotide", "oligonucleotide", and "nucleic acid" as used herein have the same meaning and refer to a nucleotide polymer having any length. Unless otherwise indicated, a particular nucleic acid sequence also implicitly encompasses conservatively-modified variants thereof (e.g. degenerate codon substitutions) and complementary sequences as well as the sequence explicitly indicated. Specifically, degenerate codon substitutions may be produced by generating sequences in which the third position of one or more selected (or all) codons is substituted with mixed-base and/or deoxyinosine residues (Batzer et al., Nucleic Acid Res. 19:5081(1991); Ohtsuka et al., J. Biol. Chem. 260:2605-2608 (1985); Rossolini et al., Mol. Cell. Probes 8:91-98 (1994)).

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene. As used herein, "gene" may refer to "polynucleotide", "oligonucleotide", "nucleic acid", and "nucleic acid molecule" and/or "protein", "polypeptide", "oligopeptide" and "peptide". As used herein, the term "open reading frame" or "ORF" in relation to a gene, refers to a reading frame which is one of three frames obtained by sectioning the base sequence of a gene at intervals of three bases, and has a start codon and a certain length curtailed by the appearance of a stop codon, and has the possibility of actually coding a protein. The entire base sequence of the genome of herpesvirus has been determined, identifying at least 101 genes. Each of the genes is known to have an open reading frame (ORF).

As used herein, the term "RNAi" is an abbreviation of RNA interference and refers to a phenomenon where an agent for causing RNAi, such as double-stranded RNA (also called dsRNA), is introduced into cells and mRNA homologous thereto is specifically degraded, so that the synthesis of gene products is suppressed, and techniques using the phenomenon. As used herein, RNAi may have the same meaning as that of an agent which causes RNAi.

As used herein, the term "an agent causing RNAi" refers to any agent capable of causing RNAi. As used herein, "an agent causing RNAi of a gene" indicates that the agent causes RNAi relating to the gene and that the effect of RNAi is successfully achieved (e.g., suppression of expression of the gene, and the like). Examples of such an agent causing RNAi include, but are not limited to, a sequence having at least about 70% homology with the nucleic acid sequence of a target gene or a sequence hybridizable thereto under stringent conditions, and RNA containing a double-stranded portion having a length of at least 10 nucleotides or variants thereof. Here, this agent may be preferably DNA containing a 3' protruding end, and more preferably the 3' protruding end has a length of 2 or more nucleotides (e.g., 2-4 nucleotides in length).

Though not wishing to be bound by any theory, a mechanism which causes RNAi is considered to be as follows. When a molecule which causes RNAi, such as dsRNA, is introduced into a cell, an RNaseIII-like nuclease having a helicase domain (called dicer) cleaves the molecule at about 20 base pair intervals from the 3' terminus in the presence of ATP in the case where the RNA is relatively long (e.g., 40 or more base pairs). As used herein, the term "siRNA" is an abbreviation of short interfering RNA and refers to short double-stranded RNA of 10 or more base pairs which are artificially chemically synthesized or biochemically synthesized, synthesized by an organism, or produced by double-stranded RNA of about 40 or more base pairs being degraded within the organism. siRNA typically has a structure comprising 5'-phosphate and 3'-OH, where the 3' terminus projects by about 2 bases. A specific protein is bound to siRNA to form RISC(RNA-induced-silencing-complex). This complex recognizes and binds to mRNA having the same sequence as that of siRNA and cleaves mRNA at the middle of siRNA due to RNaseIII-like enzymatic activity. It is preferable that the relationship between the sequence of siRNA and the sequence of mRNA to be cleaved as a target is a 100% match. However, base mutations at a site away from the middle of siRNA do not completely remove the cleavage activity by RNAi, leaving partial activity, while base mutations in the middle of siRNA have a large influence and the mRNA cleavage activity by RNAi is considerably lowered. By utilizing such a characteristic, only mRNA having a mutation can be specifically degraded. Specifically, siRNA in which the mutation is provided in the middle thereof is synthesized and is introduced into a cell. Therefore, in the present invention, siRNA per se, as well as an agent capable of producing siRNA (e.g., representatively dsRNA of about 40 or more base pairs) can be used as an agent capable of eliciting RNAi.

Also, though not wishing to be bound by any theory, apart from the above-described pathway, the antisense strand of siRNA binds to mRNA and siRNA functions as a primer for RNA-dependent RNA polymerase (RdRP), so that dsRNA is synthesized. This dsRNA is a substrate for a dicer again, leading to production of new siRNA. It is intended that such a reaction is amplified. Therefore, in the present invention, siRNA per se, as well as an agent capable of producing siRNA are useful. In fact, in insects and the like, for example, 35 dsRNA molecules can substantially or completely degrade 1,000 or more copies of intracellular mRNA, and therefore, it will be understood that siRNA per se, as well as an agent capable of producing siRNA, is useful.

In the present invention, double-stranded RNA having a length of about 20 bases (e.g., representatively about 21 to 23 bases) or less than about 20 bases, called siRNA, can be used. Expression of siRNA in cells can suppress expression of a pathogenic gene targeted by the siRNA. Therefore, siRNA can be used for the treatment, prophylaxis, prognosis, and the like of diseases.

The siRNA of the present invention may be in any form as long as it can elicit RNAi.

In another embodiment, an agent capable of causing RNAi may have a short hairpin structure having a sticky portion at the 3' terminus (shRNA; short hairpin RNA). As used herein, the term "shRNA" refers to a molecule of about 20 or more base pairs in which a single-stranded RNA partially contains a palindromic base sequence and forms a double-strand structure therein (i.e., a hairpin structure). shRNA can be artificially chemically synthesized. Alternatively, shRNA can be produced by linking sense and antisense strands of a DNA sequence in reverse directions and synthesizing RNA in vitro with T7 RNA polymerase using the DNA as a template. Though not wishing to be bound by any theory, it should be understood that after shRNA is introduced into a cell, the shRNA is degraded in the cell to a length of about 20 bases (e.g., representatively 21, 22, 23 bases), and causes RNAi as with siRNA, leading to the treatment effects of the present invention. It should be understood that such an effect is exhibited in a wide range of organisms, such as insects, plants, animals (including mammals), and the like. Thus, shRNA elicits RNAi as with siRNA and therefore can be used as an effective component of the present invention. shRNA may preferably have a 3' protruding end. The length of the double-stranded portion is not particularly limited, but is preferably about 10 or more nucleotides, and more preferably about 20 or more nucleotides. Here, the 3' protruding end may be preferably DNA, more preferably DNA of at least 2 nucleotides in length, and even more preferably DNA of 2-4 nucleotides in length.

An agent capable of causing RNAi used in the present invention may be artificially synthesized (chemically or biochemically) or naturally occurring. There is substantially no difference between the two in terms of the effect of the present invention. A chemically synthesized agent is preferably purified by liquid chromatography or the like.

An agent capable of causing RNAi used in the present invention can be produced in vitro. In this synthesis system, T7 RNA polymerase and T7 promoter are used to synthesize antisense and sense RNAs from template DNA. These RNAs are annealed and thereafter introduced into a cell. In this case, RNAi is caused via the above-described mechanism, thereby achieving the effect of the present invention. Here, for example, the introduction of RNA into a cell can be carried out using a calcium phosphate method.

Another example of an agent capable of causing RNAi according to the present invention is a single-stranded nucleic acid hybridizable to mRNA, or all nucleic acid analogs thereof. Such agents are useful for the method and composition of the present invention.

As used herein, the term "corresponding" amino acid or nucleic acid refers to an amino acid or nucleotide in a given polypeptide or polynucleotide molecule, which has, or is anticipated to have, a function similar to that of a predetermined amino acid or nucleotide in a polypeptide or polynucleotide as a reference for comparison. For example, in the case of ubiquitin, it refers to an amino acid contributing in a similar manner to the catalytic activity and present in a similar location as in the sequence (for example, glycine at the C-terminus) which is responsible for lysine. For example, in the case of nucleic acid sequence, the term refers to a similar portion which affects a similar function to the particular portion which it encodes.

As used herein, the term "corresponding" gene (e.g., a polypeptide or polynucleotide molecule) refers to a gene in a given species, which has, or is anticipated to have, a function similar to that of a predetermined gene in a species as a reference for comparison. When there are pluralities of genes having such a function, the term refers to a gene having the same evolutionary origin. Therefore, a gene corresponding to a given gene may be an ortholog of the given gene. Therefore, genes corresponding to those such as herpes virus type 6B and tumor antigen and the like, can be found in other organisms (for example, herpes virus type 7). Such a corresponding gene can be identified by techniques well known in the art. Therefore, for example, a corresponding gene in a given organism can be found by searching a sequence database of the organism (e.g., herpes virus 6B) using the sequence of a reference gene (e.g., mouse cyclin gene, etc.) as a query sequence. Alternatively, wet experiments are used for screening a library to find out the same.

As used herein, the term "isolated" means that naturally accompanying material is at least reduced, or preferably substantially or completely eliminated, in normal circumstances. Therefore, the term "isolated cell" refers to a cell substantially free from other accompanying substances (e.g., other cells, proteins, nucleic acids, etc.) in natural circumstances. The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized.

As used herein, the term "purified" biological agent (e.g., nucleic acids, proteins, and the like) refers to one from which at least a portion of naturally accompanying agents has been removed. Therefore, ordinarily, the purity of a purified biological agent is higher than that of the biological agent in a normal state (i.e., concentrated).

As used herein, the terms "purified" and "isolated" mean that the same type of biological agent is present preferably at least 75% by weight, more preferably at least 85% by weight, even more preferably at least 95% by weight, and most preferably at least 98% by weight.

As used herein, the term "homology" in relation to a sequence (e.g., a nucleic acid sequence, an amino acid sequence, etc.) refers to the proportion of identity between two or more gene sequences. Therefore, the greater the homology between two given genes, the greater the identity or similarity between their sequences. Whether or not two genes have homology is determined by comparing their sequences directly or by a hybridization method under stringent conditions. When two gene sequences are directly compared with each other, these genes have homology if the DNA sequences of the genes have representatively at least 50% identity, preferably at least 70% identity, more preferably at least 80%, 90%, 95%, 96%, 97%, 98%, or 99% identity with each other.

As used herein, "polynucleotides hybridizing under stringent conditions" refers to conditions commonly used and well known in the art. Such a polynucleotide can be obtained by conducting colony hybridization, plaque hybridization, Southern blot hybridization, or the like using a polynucleotide selected from the polynucleotides of the present invention. Specifically, a filter on which DNA derived from a colony or plaque is immobilized is used to conduct hybridization at 65° C. in the presence of 0.7 to 1.0 M NaCl. Thereafter, a 0.1 to 2-fold concentration SSC (saline-sodium citrate) solution (1-fold concentration SSC solution is composed of 150 mM sodium chloride and 15 mM sodium citrate) is used to wash the filter at 65° C. Polynucleotides identified by this method are referred to as "polynucleotides hybridizing under stringent conditions" Hybridization can be conducted in accordance with a method described in, for example, Molecular Cloning 2nd ed., Current Protocols in Molecular Biology, Supplement 1-38, DNA Cloning 1: Core Techniques, A Practical Approach, Second Edition, Oxford University Press (1995), and the like. Here, sequences hybridizing under stringent conditions exclude, preferably, sequences containing only A or T. "Hybridizable polynucleotide" refers to a polynucleotide which can hybridize to other polynucleotides under the above-described hybridization conditions. Specifically, the hybridizable polynucleotide includes at least a polynucleotide having a homology of at least 60% to the base sequence of DNA encoding a polypeptide having an amino acid sequence specifically herein disclosed, preferably a polynucleotide having a homology of at least 80%, and more preferably a polynucleotide having a homology of at least 95%.

The similarity, identity and homology of amino acid sequences and base sequences are herein compared using FASTA with the default parameters. Alternatively, an identity search may be conducted, for example, using NCBI's BLAST 2.2.9 (published May 12, 2004). As used herein, the value of identity usually refers to the value as a result of alignment with the BLAST as described above using the default parameters. If the change of parameters results in higher values, then the highest value is employed herein as the value of the identity. When a plurality of regions are evaluated for identity, the highest value is employed herein as the value of the identity.

As used herein, the term "search" indicates that a given nucleic acid sequence is utilized to find other nucleic acid base sequences having a specific function and/or property either electronically or biologically, or using other methods. Examples of an electronic search include, but are not limited to, BLAST (Altschul et al., J. Mol. Biol. 215:403-410 (1990)), FASTA (Pearson & Lipman, Proc. Natl. Acad. Sci., USA 85:2444-2448 (1988)), Smith and Waterman method (Smith and Waterman, J. Mol. Biol. 147:195-197 (1981)), and Needleman and Wunsch method (Needleman and Wunsch, J. Mol. Biol. 48:443-453 (1970)), and the like. Examples of a biological search include, but are not limited to, a macroarray in which genomic DNA is attached to a nylon membrane or the like or a microarray (microassay) in which genomic DNA is attached to a glass plate under stringent hybridization, PCR and in situ hybridization, and the like. As used herein, it is intended that promoters used in the present invention encompass a sequence corresponding to those identified by such an electronic or biological search.

As used herein, the term "expression" of a gene product, such as a gene, a polynucleotide, a polypeptide, or the like, indicates that the gene or the like is affected by a predetermined action in vivo to be changed into another form. Preferably, the term "expression" indicates that genes, polynucleotides, or the like are transcribed and translated into polypeptides. In one embodiment of the present invention, genes may be transcribed into mRNA. More preferably, these polypeptides may have post-translational processing modifications.

As used herein amino acids may be referred to with the generally known three-letter abbreviation or the one letter-abbreviation proposed by the IUPAC-IUB Biochemical Nomenclature Commission. Nucleotides may also be referred to with the generally known one-letter abbreviations which are generally accepted.

The letter codes are as follows:

| Amino Acids: | | |
| --- | --- | --- |
| 3-letter | single-letter | reference |
| Ala | A | alanine |
| Cys | C | cysteine |
| Asp | D | aspartic acid |
| Glu | E | glutamic acid |
| Phe | F | phenylalanine |
| Gly | G | glycine |
| His | H | histidine |
| Ile | I | isoleucine |
| Lys | K | lysine |
| Leu | L | leucine |
| Met | M | methionine |
| Asn | N | asparagine |
| Pro | P | proline |
| Gln | Q | glutamine |
| Arg | R | arginine |
| Ser | S | serine |
| Thr | T | threonine |
| Val | V | valine |
| Trp | W | tryptophane |
| Tyr | Y | tyrosine |
| Asx | | asparatic acid or asparagine |
| Glx | | glutamine or glutamic acid |
| Xaa | | unknown or other amino acid |

| Base (Nucleotide) | |
| --- | --- |
| abbreviation | reference |
| a | adenine |
| g | guanine |
| c | cytosine |
| t | thymine |
| u | uracyl |
| r | guanine or adenine purine |
| y | thymine/uracil or cytosine purimidine |
| m | adenin or cytocine amino group |
| k | guanine or thymine uracil keto group |
| s | guanin or cytosine |
| w | adenine or thymine/uracil |
| b | guanine or cytocine or thymine/uracil |
| d | adenine or guanine or thymine/uracil |
| h | adenine or cytosine or thymine/uracil |
| v | adenine or guanine or cytosine |
| n | adenine or guanine or cytosine or thymine/uracil, unknown or other base |

As used herein, the term "fragment" with respect to a polypeptide or polynucleotide refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more nucleotides. Lengths represented by integers which are not herein specified (e.g., 11 and the like) may be appropriate as a lower limit. For example, in the case of polynucleotides, the lower limit of the length of the fragment includes 5, 6, 7, 8, 9, 10, 15, 20, 25, 30, 40, 50, 75, 100, 200, 300, 400, 500, 600, 700, 800, 900, 1000 or more nucleotides. Lengths represented by integers which are not herein specified (e.g., 11 and the like) may be appropriate as a lower limit.

A polypeptide used in the present invention may have at least one (for example, one or several or more) amino acid substitutions, addition and/or deletion in the amino acid sequence, as long as it has substantially identical function as the wild type polypeptide.

It is well known that if a given amino acid is substituted with another amino acid having a similar hydrophobicity index, the resultant protein may still have a biological function similar to that of the original protein (e.g., a protein having an equivalent enzymatic activity). For such an amino acid substitution, the hydrophobicity index is preferably within ±2, more preferably within ±1, and even more preferably within ±0.5. It is understood in the art that hydrophobicity is considered in the modification of a protein. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1) alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5. A hydrophilicity index is also useful for modification of an amino acid sequence of the present invention. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably ±1, and even more preferably ±0.5.

The term "conservative substitution" as used herein refers to an amino acid substitution in which a substituted amino acid and a substituting amino acid have similar hydrophilicity indices or/and hydrophobicity indices. For example, the conservative substitution is carried out between amino acids having a hydrophilicity or hydrophobicity index of within ±2, preferably within ±1, and more preferably within ±0.5. Examples of conservative substitution include, but are not limited to, substitutions within each of the following residue pairs: arginine and lysine; glutamic acid and aspartic acid; serine and threonine; glutamine and asparagine; and valine, leucine, and isoleucine, which are well known to those skilled in the art.

As used herein, the term "variant" refers to a substance, such as a polypeptide, polynucleotide, or the like, which differs partially from the original substance. Examples of such a variant include a substitution variant, an addition variant, a deletion variant, a truncated variant, an allelic variant, and the like. Examples of such a variant include, but are not limited to, a nucleotide or polypeptide having one or several substitutions, additions and/or deletions or a nucleotide or polypeptide having at least one substitution, addition and/or deletion. The term "allele" as used herein refers to a genetic variant located at a locus identical to a corresponding gene, where the two genes are distinguishable from each other. Therefore, the term "allelic variant" as used herein refers to a variant which has an allelic relationship with a given gene. Such an allelic variant ordinarily has a sequence the same as or highly similar to that of the corresponding allele, and ordinarily has almost the same biological activity, though it rarely has different biological activity. The term "species homolog" or "homolog" as used herein refers to one that has an amino acid or nucleotide homology with a given gene in a given species (preferably at least 60% homology, more preferably at least 80%, at least 85%, at least 90%, and at least 95% homology). A method for obtaining such a species homolog is clearly understood from the description of the present specification. The term "orthologs" (also called orthologous genes) refers to genes in different species derived from a common ancestry (due to speciation). For example, in the case of the hemoglobin gene family having multigene structure, human and mouse α-hemoglobin genes are orthologs, while the human α-hemoglobin gene and the human β-hemoglobin gene are paralogs (genes arising from gene duplication). Orthologs are useful for estimation of molecular phylogenetic trees. Usually, orthologs in different species may have a function similar to that of the original species. Therefore, orthologs of the present invention may be useful in the present invention.

As used herein the term "functional variant" refers to a variant which retains a biological activity (in particular, promoter activity" which the sequence of standard is responsible for.

As used herein, the term "conservative (or conservatively modified) variant" applies to both amino acid and nucleic acid sequences. With respect to particular nucleic acid sequences, conservatively modified variants refer to those nucleic acids which encode identical or essentially identical amino acid sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" which represent one species of conservatively modified variation. In a nucleic acid, a conservative substitution can be confirmed by measuring promoter activity, for example.

In order to prepare functionally equivalent polypeptides, amino acid additions, deletions, or modifications can be performed in addition to amino acid substitutions. Amino acid substitution(s) refers to the replacement of at least one amino acid of an original peptide with different amino acids, such as the replacement of 1 to 10 amino acids, preferably 1 to 5 amino acids, and more preferably 1 to 3 amino acids with different amino acids. Amino acid addition(s) refers to the addition of at least one amino acid to an original peptide chain, such as the addition of 1 to 10 amino acids, preferably 1 to 5 amino acids, and more preferably 1 to 3 amino acids to an original peptide chain. Amino acid deletion(s) refers to the deletion of at least one amino acid, such as the deletion of 1 to 10 amino acids, preferably 1 to 5 amino acids, and more preferably 1 to 3 amino acids. Amino acid modification includes, but is not limited to, amidation, carboxylation, sulfation, halogenation, truncation, lipidation, alkylation, glycosylation, phosphorylation, hydroxylation, acylation (e.g., acetylation), and the like. Amino acids to be substituted or added may be naturally-occurring or nonnaturally-occurring amino acids, or amino acid analogs. Naturally-occurring amino acids are preferable.

Nucleic acid embodiment of the polypeptide to be expressed as used herein refers to a nucleic acid which allows expression of the protein embodiment of the polypeptide. Such a nucleic acid includes one in which a part of the sequence of the nucleic acid is deleted or is substituted with other base(s), or an additional nucleic acid sequence is inserted, as long as a polypeptide expressed by the nucleic acid has substantially the same activity as that of the naturally-occurring polypeptide, as described above. Alternatively, an additional nucleic acid may be linked to the 5' terminus and/or 3' terminus of the nucleic acid. The nucleic acid molecule may include one that is hybridizable to a gene encoding a polypeptide under stringent conditions and encodes a polypeptide having substantially the same function as that of that polypeptide. Such a gene is known in the art and can be used in the present invention.

The above-described nucleic acid can be obtained by a well-known PCR method, i.e., chemical synthesis. This method may be combined with, for example, site-specific mutagenesis, hybridization, or the like.

As used herein, the term "substitution, addition or deletion" for a polypeptide or a polynucleotide refers to the substitution, addition or deletion of an amino acid or its substitute, or a nucleotide or its substitute with respect to the original polypeptide or polynucleotide. This is achieved by techniques well known in the art, including a site-specific mutagenesis technique and the like. A polypeptide or a polynucleotide may have any number (>0) of substitutions, additions, or deletions. The number can be as large as a variant having such a number of substitutions, additions or deletions can maintain an intended function (e.g., the information transfer function of hormones and cytokines, etc.). For example, such a number may be one or several, and preferably within 20% or 10% of the full length sequence, or no more than 100, no more than 50, no more than 25, or the like.

(Promoter)

As used herein, the term "promoter (or promoter sequence)" refers to a base sequence which determines the initiation site of transcription of a gene and is a DNA region which directly regulates the frequency of transcription. Transcription is started by RNA polymerase binding to a promoter. Accordingly, as used herein a portion having the function of a promoter of a gene refers to "a promoter portion". A promoter region can be deduced by predicting the protein coding region in a genomic base sequence using DNA analysis software. Deduced promoter regions are usually located upstream of the structural gene although it varies, and is not limited thereto, and may also be downstream of the structural gene.

As used herein, the term "MIE promoter" refers to a major immediate early promoter, which is a promoter of a gene which is immediately transcribed by a transcription factor derived from a host and a virion after viral infection. The MIE gene may be identified by RT-PCR using an RNA extracted from an infected cell treated with cycloheximide.

As used herein, the term "U95 promoter" refers to a promoter of the immediate early gene U95. U95 is also an immediate early gene, and thus is immediately transcribed by a transcription factor derived from a host or a virion after the viral infection.

As used herein, the identification method of a promoter is as follows: some sequences in the vicinity of the structural gene are screened (for example, using an expression cassette described in the Examples), and the sequence having the gene expression promoting activity is mapped. As such, a sequence having significant promoting activity may be identified. Usually, it is located upstream of the structural gene, but is not limited thereto.

As used herein, the term "HHV6B MIE promoter" or "MIE promoter of HHV6B" refers to any sequence having promoter activity in SEQ ID NO: 1. Preferably, the promoter has position −814 to position 0 from the transcription initiation point in SEQ ID NO: 1. Such a sequence includes, but is not limited to SEQ ID NO: 1 or a sequence corresponding thereto. In the expression control of HHV6B gene, it is preferable to be located in the region at −574 to −427 from the upstream, and preferably, in the region of −1051 to −427, and the base sequence thereof includes sequences set forth in SEQ ID NO: 15, 16 and the like. Amongst them, it has been elucidated herein that NF-κB and AP-1 motifs (−603 to −594 from the transcription initiation point as the origin, corresponds to NF-κ B motif, and −488 to −478 and −249 to −239 correspond to the AP-1 motifs) may be motifs from experiments of base sequence substitution. Accordingly, preferably, the HHV6B MIE promoter of the present invention comprises: (a) a polynucleotide having the base sequence set forth in SEQ ID NO: 1, or the base sequence corresponding thereto or a fragment sequence thereof; (b) a polynucleotide of an allelic variant of the base sequence set forth in SEQ ID NO: 1 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof.

As used herein, the term "HHV7 MIE promoter" or "MIE promoter of HHV7" refers to any sequence having promoter activity in SEQ ID NO: 2. Preferably, the promoter has position −493 to position +22 from the transcription initiation point in SEQ ID NO: 2. Such a sequence includes, but is not limited to SEQ ID NO: 2 or a sequence corresponding thereto. In the expression control of the HHV7 gene, it is preferable to be located in the region at −427 from the upstream, and preferably, in the region of −493, and the base sequence thereof includes sequences set forth in SEQ ID NO: 2 and the like. Amongst them, it has been elucidated herein that NF-κB motifs (−464 to −478 and −359 to −350 from the transcription initiation point as the origin, corresponds to NF-κB motifs) may be motifs from experiments of base sequence substitution. Accordingly, preferably, the HHV7 MIE promoter of the present invention comprises: (a) a polynucleotide having the base sequence set forth in SEQ ID NO: 2, or the base sequence corresponding thereto or a fragment sequence thereof; (b) a polynucleotide of an allelic variant of the base sequence set forth in SEQ ID NO: 2 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof.

As used herein, the term "HHV7 U95 promoter" or "U95 promoter of HHV7" refers to any sequence having promoter activity in SEQ ID NO: 12. Preferably, the promoter has position −484 to position +16 from the transcription initiation point in SEQ ID NO: 12. In the expression control of the HHV7 gene, it is preferable to be located in the region at −379 from the upstream, and preferably, in the region of −484, and the base sequence thereof includes sequences set forth in SEQ ID NO: 2 and the like. Amongst them, it has been elucidated herein that NF-κB motifs (−478 to −469 and −373 to −364 from the transcription initiation point as the origin, correspond to NF-κB motifs) may be motifs from experiments of base sequence substitution. Accordingly, preferably, the HHV7 U95 promoter of the present invention comprises: (a) a polynucleotide having the base sequence set forth in SEQ ID NO: 12, or the base sequence corresponding thereto or a fragment sequence thereof; (b) a polynucleotide of an allelic variant of the base sequence set forth in SEQ ID NO: 12 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof.

"Constitutive" expression of a gene by a promoter of the present invention as used herein refers to a trait in which expression is found at a substantial but unchanged amount in any tissue of an organism during any stage in the course of the growth of the organism. Specifically, when northern blot analysis is carried out under conditions similar to those in the examples described herein, if substantial and similar expression is observed in the same or corresponding site thereof on any time points (e.g. two or more time points such as day 5 and day 15), the expression is regarded as being constitutive by the definition in the present invention. Constitutive promoters are believed to play a role in the homeostasis of organisms in a normal growth environment. These traits can be determined by extracting RNA from an arbitrary portion and subjecting the RNA to northern blot analysis to analyze expression amounts.

"Enhancer" may be used so as to enhance the expression efficiency of a gene of interest. As such an enhancer, an enhancer region containing an upstream sequence within the CaMV35S promoter is preferable. A plurality of enhancers or a single enhancer may be used, or no enhancer may be used. A region in a promoter which enhances the activity of the promoter may also be referred to as an enhancer.

As used herein, "operatively linked" or "operative link" refers to the fact that the expression (operation) of a desired sequence is located under the control of a transcription regulation sequence (e.g. promoter, enhancer or the like) or a translation regulation sequence. In order that a promoter is operably linked to a gene, the promoter is usually located immediately upstream of the gene, but is not necessarily located in a flanking manner.

(Nucleic Acid Construct)

As used herein, the term "nucleic acid construct" or "gene cassette" are interchangeably used to refer to a nucleic acid sequence comprising nucleic acid (for example, DNA, RNA) encoding a gene, a nucleic acid sequence comprising a gene promoter operably linked thereto (such that it can control the expression of the nucleic acid), a promoter, and optionally a heterologous gene operably linked thereto (i.e., in frame). It is intended that the use of this cassette or the construct optionally in combination with another regulatory element is encompassed in the present invention. Preferably expression cassettes or nucleic acid constructs are those which are amenable to specific restriction enzyme digestion and are feasible for recovery.

When a gene is mentioned herein, the term "recombinant vector" refers to a vector transferring a polynucleotide sequence of interest to a target cell. Such a vector is capable of self-replication or incorporation into a chromosome of a host cell (e.g., a prokaryotic cell, yeast, an animal cell, a plant cell, an insect cell, an individual animal, and an individual plant, etc.), and contains a promoter at a site suitable for transcription of a polynucleotide of the present invention. In the present application, for example, BAC vectors may be used. BAC vector refers to a plasmid produced based on the F plasmid of an $E.\ coli$, and is capable of propagating and stably maintaining a DNA fragment of about 300 kb or greater in size, in a bacteria such as $E.\ coli$ or the like. BAC vector comprises at least a region essential for replication of BAC vectors. Such a region essential for replication includes, for example, oriS, a replication initiation point of F plasmid, or a variant thereof.

As used herein, "selective marker" refers to a gene which functions as guidance for selecting a host cell comprising a nucleic acid construct or a vector. Selective markers include, but are not limited to: fluorescent markers, luminescent markers and drug selective markers. "Fluorescent markers" include, but are not limited to gene encoding fluorescence proteins such as green fluorescent protein (GFP), cyan fluorescent protein (CFP), yellow fluorescent protein (YFP), red fluorescent protein (dsRFP). "Luminescent markers" include but are not limited to genes encoding luminescent proteins such as luciferases. "Drug selective markers" include but are not limited to: hypoxanthine guanine phosphoribosyl transferase (hprt), dihydrofolate reductase gene, glutamine synthase gene, aspartate transaminase, metallothionein (MT), adenosine aminase (ADA), AMP deaminase (AMPD1,2), xanthine-guanine-phosphoribosyl transferase, UMP synthase, P-glycoprotein, asparagine synthase, and ornithine decarboxylase. A combination of a drug in conjunction with these drug selective markers including those encoding proteins, for example: the combination of dihydrofolate reductase (DHFR) gene and methotrexate (MTX); the combination of glutamine synthase (GS) gene and methionine sulfoximine (Msx); the combination of aspartate transaminase (AST) gene and N-phosphone acetyl-L-aspartate (PALA); the combination of MT gene and cadmium ($Cd^{2+}$); the combination of adenosine deaminase (ADA) gene and adenosine, alanosine, 2'-deoxycoformycin; the combination of AMP deaminase (AMPD1.2) gene and adenine, azaserine and coformycin; the combination of xanthine-guanine-phosphoribosyl transferase gene and mycophenolic acid; the combination of UMP synthase gene and 6-azauridine, pyrazofuran; the combination of P-glycoprotein (P-gp, MDR) gene and multi drugs; the combination of aspartate synthase (AS) gene and β-aspartyl hydroxamic acid or albizziin; ornithine carboxylase (ODC) gene and α-difluoromethyl-ornithine (DFMO) and the like.

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes (e.g. kanamycin resistant gene, hygromycin resistant gene and the like), and enhancers. It is well known in the art that a type of expression vector of a living organism such as an animal and a species of a regulatory element used may vary depending on the type of host cell used.

As used herein, the term "recombinant vector" refers to a vector transferring a polynucleotide sequence of interest to a target cell. Such a vector is capable of self-replication or incorporation into a chromosome in a host cell (e.g., a prokaryotic cell, yeast, an animal cell, a plant cell, an insect cell, an individual animal, and an individual plant, etc.), and contains a promoter at a site suitable for transcription of a polynucleotide of the present invention.

As used herein, the term "terminator" refers to a sequence which is located downstream of a protein-encoding region of a gene and which is involved in the termination of transcription when DNA is transcribed into mRNA, and the addition of a poly-A sequence. It is known that a terminator contributes to the stability of mRNA, and has an influence on the amount of gene expression. Terminators include, but are not limited to, a sequence including AATAAA.

As used herein, the term "foreign gene" to a particular organism refers to a gene which does not natively exist in the particular organism. Such a foreign gene may be a gene modified from a gene which naturally occurs in the particular organism, or a gene which naturally occurs in an organism that is different from the particular organism (such as ADA gene), or an artificially synthesized gene, or a complex thereof such as a fusion. An organism comprising such a foreign gene may express a genetic product which is not expressed in nature. For example, a recessive gene to be deleted (for example, ADA gene, PNP gene, γ c chain gene, TAP gene, MHC II gene, X-linked WASP, CD40 ligand, PI3K-like gene, DNA helicase) may be used as a foreign gene.

As used herein, the foreign gene may be a gene of a cytokine. As used herein, the term "cytokine" is defined as in the broadest sense used in the art, and a physiologically active substance which is produced from a cell and acts on the same cell or a different cell. Cytokines are generally a protein or a polypeptide, and have a controlling action of immunological response, regulation of endocrine system, regulation of the nerve system, antitumor activity, antiviral activity, regulation of cell proliferation, regulation of cellular differentiation and the like. As used herein, cytokines may exist in a form of protein or nucleic acid, and at the actual time of action, cytokines usually mean a protein form. As used herein, the term "growth factor" refers to a substance which promotes or controls the growth of a cell. Growth factors may substitute the action of serum macromolecular substances by addition to a medium in cell culture or tissue culture. Many growth factors have been found to function as a regulation factor of a differentiation state other than growth of a cell. Cytokines typically include interleukins, chemokines, hematopoietic factors such as colony stimulation factors, tumor necrosis factors, interferons. Growth factors typically include platelet derived growth factor (PDGF), epidermal growth factor (EGF), fibroblast growth factor (FGF), hepatocytic growth factor (HGF), vessel endothelial growth factor (VEGF), and the like, which show growth activity.

In the present invention, those having homology with a foreign gene of a native form as described above may be used as a foreign gene to be expressed. Such foreign genes having such homology include, but are not limited to: for example, when conducting comparison using default parameters of Blast in comparison to a foreign gene of reference to be compared, nucleic acids having sequences of identity or similarity of at least about 30%, at least about 35%, at least about 40%, at least about 30%, at least about 45%, at least about 50%, at least about 55%, at least about 60%, at least about 65%, at least about 70%, at least about 75%, at least about 80%, at least about 85%, at least about 90%, at least about 95%, at least about 99%, or polypeptides having amino acid sequence of identity or similarity of at least about 30%, at least about 35%, at least about 40%, at least about 30%, at least about 45%, at least about 50%, at least about 55%, at least about 60%, at least about 65%, at least about 70%, at least about 75%, at least about 80%, at least about 85%, at least about 90%, at least about 95%, at least about 99%.

As used herein, the term "expression" of a gene product, such as a gene, a polynucleotide, a polypeptide, or the like, indicates that the gene or the like is affected by a predetermined action in vivo to be changed into another form. Preferably, the term "expression" indicates that genes, polynucleotides, or the like are transcribed and translated into polypeptides. In one embodiment of the present invention, genes may be transcribed into mRNA. More preferably, these polypeptides may have post-translational processing modifications.

Accordingly, as used herein, "reduction" of "expression" of a gene, a polynucleotide, a polypeptide or the like refers to when an agent of the present invention is subjected to an action, whereby the amount of expression is significantly reduced compared to that when the agent is not subjected to an action. Preferably, the reduction of expression includes a reduction of the level of polypeptide expression. As used herein, the "increase" of "expression" of a gene, a polynucleotide, a polypeptide or the like refers to when an agent of the present invention is subjected to an action (or an agent relating to gene expression into a cell, for example, a gene to be expressed or an agent for regulating the same), whereby the amount of expression is significantly increased compared to when the agent is not subjected to an action. Preferably, the increase of expression includes an increase in the level of polypeptide expression. As used herein, the term "induction" of "expression" of a gene refers to an increase in the level of expression of the gene by acting an agent on a cell. Accordingly, the induction of expression encompasses when the level of expression of the gene is observed to increase from an observed level of no expression, to a noticeable level of expression of the gene.

As used herein, the term "specifically express(ing)" of a gene refers to expression in a different level (preferably in a higher level) in a specific site or period of time than that of the other site or period of time. Specific expression may refer to expression in a certain site (specific site) or may also refer to the expression including that in another site. Preferably, specific expression refers to the expression in the certain site only.

Methods of introducing a recombinant vector are also achieved by any of the above-mentioned methods for introducing DNA into a cell, and include for example, transfection, transduction, transformation and the like, such as calcium phosphate, liposome methods, DEAE dextran methods, electroporation methods, particle gun methods (gene gun), and the like, lipofection, spheroplast Proc. Natl. Acad. Sci. USA, 84, 1929 (1978)], lithium acetate method [J. Bacteriol., 153, 163 (1983)], a method described in Proc. Natl. Acad. Sci. USA, 75, 1929 (1978) and the like.

Transitional expression of Cre enzyme, DNA mapping on the chromosomes and the like, used in a method for removing a genome or genomic locus used herein or the like are well known in the art as described in "FISH jikken purotokooru hito/genomu kaiseki kara senshokutai/idenshi shindan made (FISH Experimental Protocol: from human/genomic analysis to chromosomal/genetic diagnosis)" one of "Saibo Kogaku Bessatsu Jikken Purotokooru siriizu (Cell Engineering, Special Edition, Experimental Protocol Series), ed. Ken'ichi Matsubara, Hiroshi Yoshikawa, Shujunsha (Tokyo) and the like.

As used herein, gene expression (e.g., mRNA expression, polypeptide expression) may be "detected" or "quantified" by an appropriate method, including mRNA measurement and immunological measurement. Examples of molecular biological measurement methods include Northern blotting methods, dot blotting methods, PCR methods, and the like. Examples of immunological measurement methods include ELISA methods, RIA methods, fluorescent antibody methods, Western blotting methods, immunohistological staining methods, and the like, where a microtiter plate may be used. Examples of quantification methods include ELISA methods, RIA methods, and the like. A gene analysis method using an array (e.g., a DNA array, a protein array, etc.) may be used. The DNA array is widely reviewed in Saibo-Kogaku [Cell Engineering], special issue, "DNA Microarray and Up-to-date PCR Method", edited by Shujun-sha. The protein array is described in detail in Nat. Genet. 2002 December; 32 Suppl: 526-32. Examples of methods for analyzing gene expression include, but are not limited to, RT-PCR methods, RACE methods, SSCP methods, immunoprecipitation methods, two-hybrid systems, in vitro translation methods, and the like in addition to the above-described techniques. Other analysis methods are described in, for example, "Genome Analysis Experimental Method, Yusuke Nakamura's Lab-Manual, edited by Yusuke Nakamura, Yodo-sha (2002), and the like. All of the above-described publications are herein incorporated by reference.

As used herein, the term "expression level (or amount)" refers to the amount of a polypeptide or mRNA expressed in a subject cell. The term "expression level" includes the level of protein expression of a polypeptide evaluated by any appropriate method using an antibody, including immunological measurement methods (e.g., an ELISA method, an RIA method, a fluorescent antibody method, a Western blotting method, an immunohistological staining method, and the like, or the mRNA level of expression of a polypeptide evaluated by any appropriate method, including molecular biological measurement methods (e.g., a Northern blotting method, a dot blotting method, a PCR method, and the like). The term "change in expression level" indicates that an increase or decrease in the protein or mRNA level of expression of a polypeptide evaluated by an appropriate method including the above-described immunological measurement method or molecular biological measurement method.

As used herein, the terms "transformation", "transduction" and "transfection" are used interchangeably unless otherwise mentioned, and refer to introduction of a nucleic acid into host cells. As a transformation method, any technique for introducing DNA into host cells can be used, including various well-known techniques, such as, for example, the electroporation method, the particle gun method (gene gun), the calcium phosphate method, and the like.

As used herein, the term "transformant" refers to the whole or a part of an organism, such as a cell, which is produced by transformation. Examples of a transformant include prokaryotic cells, yeast, animal cells, plant cells, insect cells and the like. Transformants may be referred to as transformed cells, transformed tissue, transformed hosts, or the like, depending on the subject. As used herein, all of the forms are encompassed, however, a particular form may be specified in a particular context.

Examples of prokaryotic cells include prokaryotic cells of the genera *Escherichia, Serratia, Bacillus, Brevibacterium, Corynebacterium, Microbacterium, Pseudomonas*, and the like, e.g., *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21(DE3), *Escherichia coli* BL21(DE3) pLysS, *Escherichia coli* HMS174(DE3), *Escherichia coli* HMS174(DE3)pLysS, *Serratia ficaria, Serratia fonticola, Serratia liquefaciens, Serratia marcescens, Bacillus subtilis, Bacillus amyloliquefaciens, Brevibacterium ammmoniagenes, Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, *Pseudomonas* sp.D-0110, and the like.

Examples of animal cells include cord blood mononuclear cells, peripheral blood mononuclear cells, Sup-T1 cells, and the like.

The term "animal" is used herein in its broadest sense and refers to vertebrates and invertebrates (e.g., arthropods). Examples of animals include, but are not limited to, any of the class Mammalia, the class Aves, the class Reptilia, the class Amphibia, the class Pisces, the class Insecta, the class Vermes, and the like.

As used herein, the term "tissue" in relation to organisms refers to an aggregate of cells having substantially the same function. Therefore, a tissue may be a part of an organ. Organs usually have cells having the same function, and may have coexisting cells having slightly different functions. Therefore, as used herein, tissues may have various kinds of cells as long as a certain property is shared by the cells.

As used herein, the term "organ" refers to a structure which has a single independent form and in which one or more tissues are associated together to perform a specific function. In plants, examples of organs include, but are not limited to, callus, root, stem, trunk, leaf, flower, seed, embryo bud, embryo, fruit, and the like. In animals, examples of organs include, but are not limited to, stomach, liver, intestine, pancreas, lung, airway, nose, heart, artery, vein, lymph node (lymphatic system), thymus, ovary, eye, ear, tongue, skin, and the like.

As used herein, the term "transgenic" refers to incorporation of a specific gene into an organism (e.g., plants or animals (mice, etc.)) or such an organism having an incorporated gene.

When organisms of the present invention are animals, the transgenic organisms can be produced by a microinjection method (a trace amount injection method), a viral vector method, an embryonic stem (ES) cell method, a sperm vector method, a chromosome fragment introducing method (transonic method), an episome method, or the like. These transgenic animal producing techniques are well known in the art.

As used herein, the term "screening" refers to selection of a substance, a host cell, a virus, or the like having a given specific property of interest from a number of candidates using a specific operation/evaluation method. It will be understood that the present invention encompasses viruses having desired activity obtained by screening.

As used herein, the terms "chip" or "microchip" are used interchangeably to refer to a micro-integrated circuit which has versatile functions and constitutes a portion of a system. Examples of a chip include, but are not limited to, DNA chips, protein chips, and the like.

The herpesvirus promoters of the present invention can be used as an ingredient of a pharmaceutical composition for the treatment, prevention, and/or therapy of lymphatic lineage or hemato-lineage, immune, and infectious diseases.

As used herein, the term "effective amount" in relation to a drug refers to an amount which causes the drug to exhibit intended efficacy. As used herein, an effective amount corresponding to a smallest concentration may be referred to as a minimum effective amount. Such a minimum effective amount is well known in the art. Typically, the minimum effective amount of a drug has been determined or can be determined as appropriate by those skilled in the art. The determination of such an effective amount can be achieved by actual administration, use of an animal model, or the like. The present invention is also useful for the determination of such an effective amount.

As used herein, the term "pharmaceutically acceptable carrier" refers to a material which is used for production of a pharmaceutical agent or an agricultural chemical (e.g., an animal drug), and has no adverse effect on effective ingredients. Examples of such a pharmaceutically acceptable carrier include, but are not limited to: antioxidants, preservatives, colorants, flavoring agents, diluents, emulsifiers, suspending agents, solvents, fillers, bulking agents, buffers, delivery vehicles, excipients, and/or agricultural or pharmaceutical adjuvants.

The type and amount of a pharmaceutical agent used in the treatment method of the present invention can be easily determined by those skilled in the art based on information obtained by the method of the present invention (e.g., information relating to a disease) in view of the purpose of use, the target disease (type, severity, etc.), the subject's age, size, sex, and case history, the morphology and type of a site of a subject of administration, or the like. The frequency of subjecting a subject (patient) to the monitoring method of the present invention is also easily determined by those skilled in the art with respect to the purpose of use, the target disease (type, severity, etc.), the subject's age, size, sex, and case history, the progression of the therapy, and the like. Examples of the frequency of monitoring the state of a disease include once per day to once per several months (e.g., once per week to once per month). Preferably, monitoring is performed once per week to once per month with reference to the progression.

As used herein, the term "instructions" refers to a description of the method of the present invention for a person who performs administration, such as a medical doctor, a patient, or the like. Instructions state when to administer a medicament of the present invention, such as immediately after or before radiation therapy (e.g., within 24 hours, etc.). The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

In a therapy of the present invention, two or more pharmaceutical agents may be used as required. When two or more pharmaceutical agents are used, these agents may have similar properties or may be derived from similar origins, or alternatively, may have different properties or may be derived from different origins. A method of the present invention can be used to obtain information about the drug resistance level of a method of administering two or more pharmaceutical agents.

Culturing methods used in the present invention are described and supported in, for example, "Doubutsu Baiyosibo Manuaru (Animal Culture Cell Manual), Eeno et al. eds., Kyoritsu shuppan, 1993, the entirety of which is hereby incorporated by reference.

(Methods for Producing Polypeptides)

The polypeptides of the present invention may be produced by culturing a transformant derived from a microorganism or an animal cell possessing a recombinant vector with a DNA encoding the polypeptide of the present invention incorporated therein, in a normal culturing manner, and producing and depositing the polypeptide of the present invention, and recovering the polypeptide of the present invention from the culture of the present invention.

The method for culturing the transformant of the present invention in a medium may be conducted according to the normal methods used in the culture of a host. Culture medium for culturing the transformant obtained by using a prokaryotic cell such as $E.\ coli$ and the like or a eukaryotic cell such as yeast as a host, include those comprising a carbon source, nitrogen source, inorganic salts and the like which can be assimilated by the organism of the present invention, and in which a transformant can efficiently be cultured, which may be natural or synthetic.

As a carbon source, those which can be assimilated by the microorganism can be used and include, for example, glucose, fructose, sucrose, sugar or honey containing the same, starch, starch hydrolysate, organic acids such as acetic acid and propionic acid, alcohols such as ethanol and propanol and the like.

As a nitrogen source, for example, the following can be used: ammonia, a variety of ammonium salts of inorganic or organic acid salt such as ammonium chloride, ammonium sulfate, ammonium acetate, ammonium phosphate, other nitrogen containing substance and the like, peptin, meat extract, yeast extract, corn steep liquid, casein hydrolysate, soybean powder, soybean powder hydrolysate, a variety of fermented bacterial bodies, and the digests thereof and the like.

As inorganic salts, the following can be used for example: potassium primary phosphate, potassium secondary phosphate, magnesium phosphate, magnesium sulfate, sodium chloride, ferrous phosphate, manganese sulfate, copper sulfate, calcium carbonate and the like. Culture will be conducted under aerobic conditions such as shaking or deep aerator agitating culture.

Culture temperature is preferably from 15-40 degrees Celsius. The period of time for culture is usually from five hours to seven days but is not limited thereto. The pH during the culture is kept from 3.0 to 9.0. The adjustment of the pH may be conducted by adding inorganic or organic acid or alkaline solution, urea, calcium carbonate, ammonia and the like. During the culture, antibiotics such as ampicillin or tetracycline or the like may be added as necessary.

When culturing a microorganism which has been transformed using an expression vector containing an inducible promoter, the culture medium may be optionally supplemented with an inducer. For example, when a microorganism, which has been transformed using an expression vector containing a lac promoter, is cultured, isopropyl-β-D-thiogalactopyranoside or the like may be added to the culture medium. When a microorganism, which has been transformed using an expression vector containing a trp promoter, is cultured, indole acrylic acid or the like may be added to the culture medium. A cell or an organ into which a gene has been introduced can be cultured in a large volume using a jar fermenter. Generally used medium for culture are used herein such as Murashige and Skoog (MS) medium, White medium, or these medium supplemented with auxin, cytokine or plant hormones and the like.

For example, when using an animal cell, mediums used for culturing the cell of the subject invention include, for example those generally used such as RMPI1640 medium [The Journal of the American Medical Association, 199, 519(1967)], Eagle's MEM medium [Science, 122, 501(1952)] DMEM medium [Virology, 8, 396(1959)], 199 medium [Proceedings of the Society for the Biological Medicine, 73, 1(1950)], or such a culture medium supplemented with fetal bovine serum or the like.

Culture is normally carried out for 1 to 7 days under conditions such as pH 6 to 8, 25 to 40° C., 5% $CO_2$. An antibiotic, such as kanamycin, penicillin, streptomycin, or the like may be optionally added to the culture medium during cultivation.

A polypeptide of the present invention can be isolated or purified from a culture of a transformant, which has been transformed with a nucleic acid sequence encoding the polypeptide, using an ordinary method for isolating or purifying enzymes, which are well known and commonly used in the art. For example, when a polypeptide of the present invention is secreted outside a transformant for producing the polypeptide, the culture is subjected to centrifugation or the like to obtain a soluble fraction. A purified specimen can be obtained from the soluble fraction by a technique, such as solvent extraction, salting-out/desalting with ammonium sulfate or the like, precipitation with organic solvent, anion exchange chromatography with a resin (e.g., diethylaminoethyl (DEAE)-Sepharose, DIAION HPA-75 (Mitsubishi Chemical Corporation), etc.), cation exchange chromatography with a resin (e.g., S-Sepharose FF (Pharmacia), etc.), hydrophobic chromatography with a resin (e.g., buthylsepharose, phenylsepharose, etc.), gel filtration with a molecular sieve, affinity chromatography, chromatofocusing, electrophoresis (e.g., isoelectric focusing electrophoresis, etc.).

When the polypeptide of the present invention has been expressed and formed insoluble bodies within cells, the cells are harvested, pulverized, and centrifuged. From the resulting precipitate fraction, the polypeptide of the present invention is collected using a commonly used method. The insoluble polypeptide is solubilized using a polypeptide denaturant.

The resulting solubilized solution is diluted or dialyzed into a denaturant-free solution or a dilute solution, where the concentration of the polypeptide denaturant is too low to denature the polypeptide. The polypeptide of the present invention is allowed to form a normal three-dimensional structure, and the purified specimen is obtained by isolation and purification as described above.

Purification can be carried out in accordance with a commonly used protein purification method (J. Evan. Sadler et al.: Methods in Enzymology, 83, 458). Alternatively, the polypeptide of the present invention can be fused with other proteins to produce a fusion protein, and the fusion protein can be purified using affinity chromatography using a substance having affinity to the fusion protein (Akio Yamakawa, Experimental Medicine, 13, 469-474 (1995)). For example, in accordance with a method described in Lowe et al., Proc. Natl. Acad. Sci., USA, 86, 8227-8231 (1989), Genes Develop., 4, 1288 (1990)), a fusion protein of the polypeptide of the present invention with protein A is produced, followed by purification with affinity chromatography using immunoglobulin G.

A fusion protein of the polypeptide of the present invention with a FLAG peptide is produced, followed by purification with affinity chromatography using anti-FLAG antibodies (Proc. Natl. Acad. Sci., USA, 86, 8227 (1989), Genes Develop., 4, 1288 (1990)).

The polypeptide of the present invention can be purified with affinity chromatography using antibodies which bind to the polypeptide. The polypeptide of the present invention can be produced using an in vitro transcription/translation system in accordance with a known method (J. Biomolecular NMR, 6, 129-134; Science, 242, 1162-1164; J. Biochem., 110, 166-168 (1991)).

The polypeptide of the present invention can also be produced by a chemical synthesis method, such as the Fmoc method (fluorenylmethyloxycarbonyl method), the tBoc method (t-buthyloxycarbonyl method), or the like, based on the amino acid information thereof. The peptide can be chemically synthesized using a peptide synthesizer (manufactured by Advanced ChemTech, Applied Biosystems, Pharmacia Biotech, Protein Technology Instrument, Synthecell-Vega, PerSeptive, Shimadzu, or the like).

The structure of the purified polypeptide of the present invention can be produced by methods commonly used in protein chemistry (see, for example, Hisashi Hirano. "Protein Structure Analysis for Gene Cloning", published by Tokyo Kagaku Dojin, 1993). The physiological activity of a polypeptide of the present invention can be measured in accordance with a known measurement method.

(Method for Producing Variant Polypeptides)

Deletion, substitution or addition of an amino acid of the polypeptide of the present invention may be carried out by site directed mutagenesis, which was well known prior to the present application. Those with one or more amino acids deleted, substituted or added may be prepared in accordance with the methods described in: Molecular Cloning, A Laboratory Manual, Second Edition, Cold Spring Harbor Laboratory Press (1989), Current Protocols in Molecular Biology, Supplement 1~38, John Wiley & Sons (1987-1997), Nucleic Acids Research, 10, 6487(1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985), Proc. Natl. Acad. Sci., USA, 81, 5662 (1984), Science, 224, 1431 (1984), PCT WO85/00817 (1985), Nature, 316, 601 (1985) and the like.

(Gene Therapy)

In certain embodiments, a nucleic acid comprising a sequence encoding an antibody or a functional derivative thereof is administered for the purpose of gene therapy for treating, inhibiting or preventing a disease or disorder related to abnormal expression and/or activity of a polypeptide used in the present invention. Gene therapy refers to a therapy performed by administering a nucleic acid, which has been expressed or is capable of being expressed, into subjects. In this embodiment of the present invention, a nucleic acid produces a protein encoded thereby and the protein mediates a therapeutic effect.

Any method available in the art for gene therapy may be used in accordance with the present invention. Illustrative methods are described below.

See the following review articles for gene therapy: Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62:191-217 (1993); and May, TIBTECH 11(5):155-215 (1993). Generally known recombinant DNA techniques used for gene therapy are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

(Demonstration of Therapeutic Activity or Preventive Activity)

The compounds or pharmaceutical compositions of the present invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those skilled in the art (including, but not limited to, cell lysis assays). In accordance with the present invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

(Therapeutic/Prophylactic Administration and Composition)

The present invention provides methods of treatment, prevention and prophylaxis by administration to a subject of an effective amount of a component or pharmaceutical composition comprising the promoter of the present invention. In a preferable aspect, the component comprising a promoter may be substantially purified (for example, including the state where the effects are reduced, or a substance causing undesirable side effect is substantially free). Subjects may preferably be an animal including but not limited to: cattle, pigs, horses, chickens, cats, dogs and the like, and preferably primates, and most preferably humans.

When a nucleic acid molecule or polypeptide of the present invention is used as a medicament, the medicament may further comprise a pharmaceutically acceptable carrier. Any pharmaceutically acceptable carrier known in the art may be used in the medicament of the present invention.

Examples of a pharmaceutically acceptable carrier or a suitable formulation material include, but are not limited to, antioxidants, preservatives, colorants, flavoring agents, diluents, emulsifiers, suspending agents, solvents, fillers, bulky agents, buffers, delivery vehicles, and/or pharmaceutical adjuvants. Typically, a medicament of the present invention is administered in the form of a composition comprising a polypeptide or a polynucleotide or a variant or fragment thereof, or a variant or derivative thereof, or an agent capable of modulating any of these substances, with at least one physiologically acceptable carrier, excipient or diluent. For example, an appropriate vehicle may be injection solution, physiological solution, or artificial cerebrospinal fluid, which can be supplemented with other substances which are commonly used for compositions for parenteral delivery.

Acceptable carriers, excipients or stabilizers used herein preferably are nontoxic to recipients and are preferably inert at the dosages and concentrations employed, and preferably include phosphate, citrate, or other organic acids; ascorbic acid, α-tocopherol; low molecular weight polypeptides; proteins (e.g., serum albumin, gelatin, or immunoglobulins); hydrophilic polymers (e.g., polyvinylpyrrolidone); amino acids (e.g., glycine, glutamine, asparagine, arginine or lysine); monosaccharides, disaccharides, and other carbohydrates (glucose, mannose, or dextrins); chelating agents (e.g., EDTA); sugar alcohols (e.g., mannitol or sorbitol); salt-forming counterions (e.g., sodium); and/or nonionic surfactants (e.g., Tween, pluronics or polyethylene glycol (PEG)).

Examples of appropriate carriers include neutral buffered saline or saline mixed with serum albumin. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

The medicament of the present invention may be administered orally or parenterally. Alternatively, the medicament of the present invention may be administered intravenously or subcutaneously. When systemically administered, the medicament for use in the present invention may be in the form of a pyrogen-free, pharmaceutically acceptable aqueous solution. The preparation of such pharmaceutically acceptable compositions, with due regard to pH, isotonicity, stability and the like, is within the skill of the art. Administration methods may be herein oral, parenteral administration (e.g., intravenous, intramuscular, subcutaneous, intradermal, to mucosa, intrarectal, vaginal, topical to an affected site, to the skin, etc.). A prescription for such administration may be provided in any formulation form. Such a formulation form includes liquid formulations, injections, sustained preparations, and the like.

The medicament of the present invention may be prepared for storage by mixing a sugar chain composition having the desired degree of purity with optional physiologically acceptable carriers, excipients, or stabilizers (Japanese Pharmacopeia ver. 14, or a supplement thereto or the latest version; Remington's Pharmaceutical Sciences, 18th Edition, A. R. Gennaro, ed., Mack Publishing Company, 1990; and the like), in the form of lyophilized cake or aqueous solutions.

The type and amount of a pharmaceutical agent used in the treatment method of the present invention can be easily determined by those skilled in the art based on information obtained by the method of the present invention (e.g., information relating to a disease) in view of the purpose of use, the target disease (type, severity, etc.), the subject's age, size, sex, and case history, the morphology and type of a site of a subject of administration, or the like. The frequency of subjecting a subject (patient) to the monitoring method of the present invention is also easily determined by those skilled in the art with respect to the purpose of use, the target disease (type, severity, etc.), the subject's age, size, sex, and case history, the progression of the therapy, and the like. Examples of the frequency of monitoring the state of a disease include once per day to once per several months (e.g., once per week to once per month). Preferably, monitoring is performed once per week to once per month with reference to the progression.

(Immune Therapy)

As used herein the term "vaccine" refers to a composition (for example, suspension or solution) comprising a usually infectious agent or a portion of an infectious agent, an agent (for example, gene sequence) which allows production of such an agent or portion, to induce an active immune response. Antigenic portions constituting vaccines may be a microorganism (such as a virus or bacteria or the like), a native product purified from such a microorganism, a synthetic product or genetically engineered proteins, peptides, polysaccharides or similar products and nucleic acid molecules comprising a nucleic acid sequence encoding such proteins. Vaccines express the effects thereof by causing a neutralizing antibody.

As used herein the term "gene vaccine" refers to a composition (for example, suspension or solution or the like) comprising an agent (typically nucleic acid molecule) which is expressed in the subject to be administered and whose expressed product has vaccine action. Typical genetic vaccines may be nucleic acid molecules comprising the nucleic acid sequence encoding a gene product having antigenicity (for example, vectors, plasmids, Naked DNA and the like).

As used herein, immunologic effects of the vaccines according to the present invention can be confirmed by using any method known in the art. Such a method includes, but is not limited to: for example, CTL precursor cell frequency analysis, ELISPOT method, tetramer method, realtime PCR method and the like. As an exemplary description for CTL precursor frequency analysis, peripheral lymphocyte or antigenic peptide and lymphocyte cultured in the presence of IL-2, were subjected to limitation dilution, and IL-2 and feeder cells were cultured under coexistence, and the wells having propagation were stimulated with vaccines or their candidates, and the presence or absence of IFN-γ production is measured using ELISA. Herein, positive wells are used to calculate the frequency of CTL precursor cells according to the Poisson Analysis, to evaluate efficacy of the vaccines. As used herein, the number of positive cells is the number of antigen-specific CTLs and the greater the number is, the greater the efficacy of the vaccine.

The present invention may be used as a cancer vaccine. In such a case cancer antigens may be incorporated as a foreign gene.

As used herein, the term "cancer antigen" refers to an antigen molecule which will be newly expressed in association with canceration of a normal cell. Such a cancer antigen includes, but is not limited to, for example:

(1) tumor virus derived antigens (for example, T antigens or the like from DNA type tumor virus such as adenovirus, polyoma virus, SV40 and the like). In RNA-type tumor virus of human or mouse, viral envelope proteins are expressed on the cellular surface;

(2) tumor specific transplantation antigen (TSTA); this antigen refers to a target antigen of a cancer cell of the same lineage, when the cancer cell is rejected as a result of formation of a specific immune response. Genetic mutations cause variant proteins in a cancer cell, which allows expression thereof on the cellular surface of the cancer cell by association with a molecule of major histocompatibility (MHC) antigen gene complex as peptide fragments, as in other intracellular normal proteins;

(3) tumor associated antigen (TAA): antigens which exhibit specific expression in association with canceration, although it is not necessarily specific to the cancer cell. For example, it corresponds to α-fetoprotein in liver cancer, carcinoembryonic antigen (CEA) in enteric cancer and the like. These are proteins which are originally present only in normal fetuses, and are not found in the tissues of an adult. However, these proteins are called oncofetal antigens as re-expression will occur with the canceration.

As used herein, any form of cancer antigen may be used, and in particular, a form of carcinoma-related antigen is preferably used. This is because it will be expressed on the surface of a cancer cell upon association with MHC.

As used herein, the term "adjuvant" refers to a substance which increases, or otherwise alters, immune response when mixed with immunogen administered thereinto. Adjuvants are classified in view of minerals, bacteria, plants, synthetic, or products of a host, for example.

As used herein, the term "pathogen" refers to an organism or agent which allows onset of a disease or a disorder to a host.

As used herein, the terms "prophylaxis", "prophylactic" "prevention" and "prevent" refer to a treatment of a disease or a disorder, in which such a disease or disorder should not be caused prior to the actual onset thereof.

As used herein, the terms "therapy", "treatment" and "treat" refer to a treatment in which in the case where such occurs, deterioration of such a disease or disorder is prevented, preferably, at least maintaining the status quo, more preferably, alleviation further more preferably, cleared.

The vaccines of the present invention are preferably tested in vitro, and then in vivo for the desired therapeutic or prophylactic activity, prior to use in humans. For example, in vitro assays to demonstrate the therapeutic or prophylactic utility of vaccines according to the present invention include testing the effect of a vaccine on a cell line or a patient tissue sample. The effect of the vaccines on the cell line and/or tissue sample can be determined utilizing techniques known to those of skill in the art (for example, immunological assay such as ELISA). In vivo tests include but are not limited to: for example, a method for testing whether a neutralizing antibody is raised.

As used herein the term "patient" or "subject" refers to an organism to which the treatment or composition of the present invention is applied. Preferably, the patient may be a human.

The present invention provides methods of treatment, inhibition and prophylaxis by administration to a subject of an effective amount of a gene vaccine of the present invention. In a preferred aspect, the compound is substantially purified (e.g., substantially free from substances that limit its effect or produce undesired side-effects).

As used herein, the term "administer" means that the polypeptides, polynucleotides or the like of the present invention or pharmaceutical compositions containing them are incorporated into the cells, tissue or body of an organism either alone or in combination with other therapeutic agents. Combinations may be administered either concomitantly (e.g., as an admixture), separately but simultaneously or concurrently; or sequentially. This includes presentations in which the combined agents are administered together as a therapeutic mixture, and also procedures in which the combined agents are administered separately but simultaneously (e.g., as through separate or the same mucosa into the same individual). "Combination" administration further includes the separate administration of one of the compounds or agents given first, followed by the second.

Administration of vaccines according to the present invention may be conducted in any manner, and preferably it is advantageous to use a needleless syringe. This is because it can administer without causing undue load to a patient.

As used herein the term "needleless syringe" refers to a medical device which transfers a drug solution into the skin by moving a piston by gas pressure or elasticity of an elastic member, thereby administering a drug component into subcutaneous or preferably into the cell's subcutaneous site.

Specifically, for example, Shimajet™ (manufactured by Shimadzu, inc.), Medi-Jector Vision™ (manufactured by Elitemedica), PenJet™ (manufactured by Penjet), which are commercially available. Gene gun (particle gun) refers to a medical and experimental device which allows in vivo gene introduction by accelerating high density particles such as gold or tungsten coated with DNA using gas pressure of helium or the like. Advantageous effects of gene guns include effective intracellular introduction of a low amount of DNA, and stable results have been obtained with different operators.

Specifically, for example, Helios Gene Gun from Bio-Rad, USA is commercially available.

As used herein, the term "instructions" refers to a description of the method of the present invention for a person who performs administration, such as a medical doctor, a patient, or the like. Instructions state when to administer a medicament of the present invention, such as immediately after or before radiation therapy (e.g., within 24 hours, etc.). The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

The judgment of termination of treatment or prevention with a method of the present invention may be supported by the result of an antibody raised using a commercially available assay or device.

The present invention also provides a pharmaceutical package or kit comprising containers loaded with one or more pharmaceutical compositions according to the present invention. A notice in a form defined by a government agency which regulates the production, use or sale of pharmaceutical products or biological products may be arbitrarily attached to such a container, representing the approval of the government agency relating to production, use or sale with respect to administration to humans.

(General Techniques Used Herein)

Techniques used herein are within the technical scope of the present invention unless otherwise specified. These techniques are commonly used in the fields of sugar chain science, fluidics, microfabrication, organic chemistry, biochemistry, genetic engineering, molecular biology, microbiology, genetics, and their relevant fields. The techniques are sufficiently well described in documents described below and other documents mentioned herein.

Microfabrication is described in, for example, Campbell, S. A. (1996), The Science and Engineering of Microelectronic Fabrication, Oxford University Press; Zaut, P. V. (1996), Micromicroarray Fabrication: a Practical Guide to Semiconductor Processing, Semiconductor Services; Madou, M. J. (1997), Fundamentals of Microfabrication, CRC1 5 Press; Rai-Choudhury, P. (1997), Handbook of Microlithography, Micromachining & Microfabrication: Microlithography; and the like, the relevant portions of which are hereby incorporated by reference.

Molecular biology techniques, biochemistry techniques, and microbiology techniques used herein are well known and commonly used in the art, and are described in, for example, Maniatis, T. et al. (1989), Molecular Cloning: A Laboratory Manual, Cold Spring Harbor and its 3rd Ed. (2001); Ausubel, F. M. et al. eds, Current Protocols in Molecular Biology, John Wiley & Sons Inc., NY, 10158 (2000); Innis, M. A. (1990), PCR Protocols: A Guide to Methods and Applications, Academic Press; Innis, M. A. et al. (1995), PCR Strategies, Academic Press; Sninsky, J. J. et al. (1999), PCR Applications: Protocols for Functional Genomics, Academic Press; Gait, M. J. (1985), Oligonucleotide Synthesis: A Practical Approach, IRL Press; Gait, M. J. (1990), Oligonucleotide Synthesis: A Practical Approach, IRL Press; Eckstein, F. (1991), Oligonucleotides and Analogues: A Practical Approac, IRL Press; Adams, R. L. et al. (1992), The Biochemistry of the Nucleic Acids, Chapman & Hall; Shabarova, Z. et al. (1994), Advanced Organic Chemistry of Nucleic Acids, Weinheim; Blackburn, G. M. et al. (1996), Nucleic Acids in Chemistry and Biology, Oxford University Press; Hermanson, G. T. (1996), Bioconjugate Techniques, Academic Press; Method in Enzymology 230, 242, 247, Academic Press, 1994; Special issue, Jikken Igaku (Experimental Medicine) "Idenshi Donyu & Hatsugenkaiseki Jikkenho (Experimental Method for Gene introduction & Expression Analysis)", Yodo-sha, 1997; and the like. Relevant portions (or possibly the entirety) of each of these publications are herein incorporated by reference.

DESCRIPTION OF PREFERRED EMBODIMENTS

Hereinafter, the present invention will be described by way of embodiments. Embodiments described below are provided only for illustrative purposes. Accordingly, the scope of the present invention is not limited by the embodiments except as by the appended claims. It will be clearly appreciated by those skilled in the art that variations and modifications can be made without departing from the scope of the present invention with reference to the specification.

In an aspect, the present invention provides MIE promoters of HHV (including HHV6A and HHV6B, in particular HHV6B) and HHV7, and/or U95 promoter of HHV7. In particular, it has been discovered that MIE promoter of HHV6B, MIE promoter of HHV7, and U95 promoter of HHV7 are surprisingly enhanced in selectivity to lymphocytes in comparison to IE promoters of HCMV. In particular, adhesive cells (293 cells, Vero cells and the like) only showed one hundredth the activity of that of HCMV IE promoter, whereas in lymphoid cells such as SupT1, U937 and the like, a several fold increase in expression efficiency has been obtained. Such a high level of selectivity or specificity elucidated that it can be applied to the development of a pharmaceutical which is targeted to DNA vaccines, gene therapy, in particular, to lymphocytes. Moreover, in an expression system in vivo, since activities are diminished even in the case of CMV promoters which have potent activity, due to the action of methylase, it is understood that the promoter of the present invention may be used to secure expression amount in vivo in blood cells or lymphocyte cells. In genetic diseases, gene therapy of cancer, retroviruses are generally used, however, LTR activity is not so potent, as a promoter, the introduction of the promoter of the present invention upstream of the gene to be expressed allows potent expression in blood cell lineage cells. The present invention is also useful in gene therapy targeting blood cell diseases such as leukemia and the like. Furthermore, RNAi is used as a method of knocking out gene expression, and the promoter of the present invention is used as a promoter for hair-pin type RNA expression vectors, allowing more efficient effects of inhibition of expression in the blood cell lineage. Macrophages or dendritic cells or the like are purified from native peripheral blood using flow cytometry, and these cells are transfected with plasmids constructed so as to express cancer specific antigen or tumor necrosis factor (TNF) or the like under the control of the promoter of the present invention, and reintroduced to the original body after confirmation of expression of cancer antigen, thereby practicing the gene therapy of cancer as a result of efficient activation of tumor antigen specific CTL via Glass I-HLA.

In one embodiment, the promoters of the present invention may have a length of at least 8 contiguous nucleotides. Preferably, the promoter of the present invention includes at least the R3 region or the functional variant thereof, amongst the sequence set forth in SEQ ID NO: 1. More preferably, the promoter of the present invention includes at least the sequence of −574 to −427 from the transcription initiation point of the SEQ ID NO: 1; more preferably, at least the sequence of −1051 to −427 from the transcription initiation point of the SEQ ID NO: 1. This is because it is predicted that these regions have regions having enhancer activity.

In one embodiment, the promoter of the present invention comprises NF-κB and AP-1 motives.

In a preferable embodiment, the promoter of the present invention comprises a sequence set forth in SEQ ID NO: 1, and more preferably consists essentially of the sequence set forth in SEQ ID NO: 1.

In one embodiment, the promoter of the present invention comprises: (a) a polynucleotide having the base sequence set forth in SEQ ID NO: 1, or the base sequence corresponding thereto or a fragment sequence thereof; (b) a polynucleotide of an allelic variant of the base sequence set forth in SEQ ID NO: 1 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof. As used herein, the biological activity may be promoter and/or enhancer activities but is not limited thereto. Promoter and enhancer activities may be measured using well known technology in the art, and such a technology is described herein and exemplified in the Examples.

In one preferred embodiment, the number of substitutions, additions and deletions described in (a) through (d) above may be limited to, for example, preferably 50 or less, 40 or less, 30 or less, 20 or less, 15 or less, 10 or less, 9 or less, 8 or less, 7 or less, 6 or less, 5 or less, 4 or less, 3 or less, or 2 or less. The number of substitutions, additions and deletions is preferably small, but may be large as long as the biological activity is maintained (preferably, the activity is similar to or substantially the same as that of HHV6B MIE promoter).

In a preferred embodiment, the identity to any one of the polynucleotides described in (a) to (d) above or a complementary sequence thereof may be at least about 80%, more preferably at least about 90%, even more preferably at least about 98%, and most preferably at least about 99%.

In a preferred embodiment, the nucleic acid molecule of the present invention may have a length of at least 8 contiguous nucleotides. The appropriate nucleotide length of the nucleic acid molecule of the present invention may vary depending on the purpose of use of the present invention. More preferably, the nucleic acid molecule of the present invention may have a length of at least 10 contiguous nucleotides, even more preferably at least 15 contiguous nucleotides, and still even more preferably at least 20 contiguous nucleotides. These lower limits of the nucleotide length may be present between the above-specified numbers (e.g., 9, 11, 12, 13, 14, 16, and the like) or above the above-specified numbers (e.g., 21, 22, ... 30, and the like). The upper limit of the length of the polypeptide of the present invention is not limited as long as it can be used for the intended purpose (e.g. promoter). Stringency may be high, or intermediate or low, and the level of stringency may be appropriately determined according to the circumstances.

In a different embodiment, the promoter according to the present invention may have a length of at least 8 contiguous nucleotides. Preferably, the promoter of the present invention includes at least the R2 region or the functional variant thereof, amongst the sequence set forth in SEQ ID NO; 2. More preferably, the promoter of the present invention includes at least the sequence of −388 to +22 from the transcription initiation point of the SEQ ID NO: 2; more preferably, at least the sequence of −493 to +22 from the transcription initiation point of the SEQ ID NO: 2. This is because it is predicted that these regions contain regions having enhancer activity.

In one embodiment, the promoter according to the present invention includes NF-κB motifs (−464 to −478 and −359 to −350 in SEQ ID NO: 2).

In a preferable embodiment, the promoter of the present invention comprises, the sequence set forth in SEQ ID NO: 2, and more preferably, consists essentially of the sequence set forth in SEQ ID NO; 2.

In one embodiment, the promoter of the present invention comprises: (a) a polynucleotide having the base sequence set forth in SEQ ID NO: 2, or the base sequence corresponding thereto or a fragment sequence thereof; (b) a polynucleotide of an allelic variant of the base sequence set forth in SEQ ID NO: 2 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof. As used herein, the biological activity may be promoter and/or enhancer activities but is not limited thereto. Promoter and enhancer activities may be measured using well known technology in the art, and such a technology is described herein and exemplified in the Examples.

In one preferred embodiment, the number of substitutions, additions and deletions described in (a) through (d) above may be limited to, for example, preferably 50 or less, 40 or less, 30 or less, 20 or less, 15 or less, 10 or less, 9 or less, 8 or less, 7 or less, 6 or less, 5 or less, 4 or less, 3 or less, or 2 or less. The number of substitutions, additions and deletions is preferably small, but may be large as long as the biological activity is maintained (preferably, the activity is similar to or substantially the same as that of HHV7 MIE promoter).

In a preferred embodiment, the identity to any one of the polynucleotides described in (a) to (d) above or a complementary sequence thereof may be at least about 80%, more preferably at least about 90%, even more preferably at least about 98%, and most preferably at least about 99%.

In a preferred embodiment, the nucleic acid molecule of the present invention may have a length of at least 8 contiguous nucleotides. The appropriate nucleotide length of the nucleic acid molecule of the present invention may vary depending on the purpose of use of the present invention. More preferably, the nucleic acid molecule of the present invention may have a length of at least 10 contiguous nucleotides, even more preferably at least 15 contiguous nucleotides, and still even more preferably at least 20 contiguous nucleotides. These lower limits of the nucleotide length may be present between the above-specified numbers (e.g., 9, 11, 12, 13, 14, 16, and the like) or above the above-specified numbers (e.g., 21, 22, ... 30, and the like). The upper limit of the length of the polypeptide of the present invention is not limited as long as it can be used for the intended purpose (e.g. promoter). Stringency may be high, or intermediate or low, and the level of stringency may be appropriately determined according to the circumstances.

In another embodiment, the promoter of the present invention may have a length of at least 8 contiguous nucleotides. Preferably, the promoter of the present invention includes at least the R2 region or the functional variant thereof, amongst the sequence set forth in SEQ ID NO; 12. More preferably, the promoter of the present invention includes at least the sequence of −379 to +16 from the transcription initiation point of the SEQ ID NO: 12; more preferably, at least the sequence of −484 to +16 from the transcription initiation point of the SEQ ID NO: 12. This is because it is predicted that these regions containing regions having enhancer activity.

In one embodiment, the promoter according to the present invention includes NF-κB motifs (−478 to −469 and −373 to −364 in SEQ ID NO: 12).

In a preferable embodiment, the promoter of the present invention comprises, the sequence set forth in SEQ ID NO: 12, and more preferably, consists essentially of the sequence set forth in SEQ ID NO; 12.

In one embodiment, the promoter of the present invention comprises: (a) a polynucleotide having the base sequence set forth in SEQ ID NO: 12, or the base sequence corresponding thereto or a fragment sequence thereof; (b) a polynucleotide of an allelic variant of the base sequence set forth in SEQ ID NO: 12 or the base sequence corresponding thereto or a fragment sequence thereof; (c) a polynucleotide which hybridizes a polynucleotide of any of (a) or (b) and has a biological activity thereof; or (d) a polynucleotide which consists of the base sequence of any of (a) to (c) or a complement sequence thereof with at least 70% identity, and has a biological activity thereof. As used herein, the biological activity may be promoter and/or enhancer activities but is not limited thereto. Promoter and enhancer activities may be measured using well known technology in the art, and such a technology is described herein and exemplified in the Examples.

In one preferred embodiment, the number of substitutions, additions and deletions described in (a) through (d) above may be limited to, for example, preferably 50 or less, 40 or less, 30 or less, 20 or less, 15 or less, 10 or less, 9 or less, 8 or less, 7 or less, 6 or less, 5 or less, 4 or less, 3 or less, or 2 or less. The number of substitutions, additions and deletions is preferably small, but may be large as long as the biological activity is maintained (preferably, the activity is similar to or substantially the same as that of the HHV7 U95 promoter).

In a preferred embodiment, the identity to any one of the polynucleotides described in (a) to (d) above or a complementary sequence thereof may be at least about 80%, more preferably at least about 90%, even more preferably at least about 98%, and most preferably at least about 99%.

In a preferred embodiment, the nucleic acid molecule of the present invention may have a length of at least 8 contiguous nucleotides. The appropriate nucleotide length of the nucleic acid molecule of the present invention may vary depending on the purpose of use of the present invention. More preferably, the nucleic acid molecule of the present invention may have a length of at least 10 contiguous nucleotides, even more preferably at least 15 contiguous nucleotides, and still even more preferably at least 20 contiguous nucleotides. These lower limits of the nucleotide length may be present between the above-specified numbers (e.g., 9, 11, 12, 13, 14, 16, and the like) or above the above-specified numbers (e.g., 21, 22, . . . 30, and the like). The upper limit of the length of the polypeptide of the present invention is not limited as long as it can be used for the intended purpose (e.g. promoter). Stringency may be high, or intermediate or low, and the level of stringency may be appropriately determined according to the circumstances.

In another aspect, the present invention provides a nucleic acid construct comprising a promoter of the present invention (MIE promoter of HHV6, MIE promoter of HHV7, U95 promoter of HHV7 and the like). Such a nucleic acid construct has a property of inducing expression in a lymphocyte specific manner, and the utility thereof is high, and exhibits unexpectedly high selectivity in comparison to human cytomegalovirus (HCMV) IE promoter.

Accordingly, in one embodiment, the nucleic acid construct of the present invention comprises a sequence encoding a foreign gene having a different origin than the promoter of the present invention, with a sequence of the present invention operably linked thereto.

Such a foreign gene includes, but is not limited to, for example, those encoding an RNAi molecule, drug resistance, a recessive gene to be deleted, a selective marker and the like.

Preferably, selective markers used in the present invention are those allowing selection in a medium for the host into which the nucleic acid construct is introduced, and for example, these selective markers may be those allowing visible selection in the host into which the nucleic acid construct is introduced, and exemplifies hypoxanthine guanine transferase (hprt) or a fluorescent marker selected from the group consisting of green fluorescent protein (GFP), cyan fluorescent protein (CFP), yellow fluorescent protein (YFP) and red fluorescent protein (dsRed) and the like.

Preferably, selective markers included in the nucleic acid construct of the present invention are advantageously those substantially exhibiting no toxicity against the host into which the nucleic acid construct is introduced according to the present invention. This is because, when using the present invention for the purpose of therapy or prevention, adverse effects should be preferably none.

Those to be included in the nucleic acid construct according to the present invention include for example, a recessive gene to be deleted. As used herein, a recessive gene to be deleted refers to any recessive gene which exhibits diseased condition when deleted, and includes, but is not limited to, for example: ADA gene (which is related to severe combined immunodeficiency (SCID)), PNP gene (severe combined immunodeficiency (SCID)), γ c chain gene (which is related to severe combined immunodeficiency (SCID)), TAP gene (which is related to MHC I deficiency), MHC II gene (which is related to MHC II deficiency), X-linked WASP (which is related to Wiskott-Aldrich syndrome), CD40 ligand (which is related to X-linked high IgM syndrome), PI3K-like gene (which is related to granuloma telangiectaticum) and DNA helicase (which is related to Bloom's syndrome), and the like.

In a preferable embodiment, drugs to be included in the nucleic acid construct of the present invention may be proteineous agents such as a cytokine, a chemokine, a growth factor, a protein hormone, and a peptide hormone such as IFN-α, IFN-γ, IL-2, IL-12, G-CSF, GM-CSF and the like.

In one embodiment, in the nucleic acid construct of the present invention the promoter induces specific expression of the foreign gene in a hemocyto-lineage cell, in particular, in a T cell.

In another aspect, the present invention provides an expression vector comprising the nucleic acid construct according to the present invention. Such an expression vector may include elements essential to expression, which may not exist in the nucleic acid construct of the present invention, for example, terminator, enhancer sequences, in an operably linked manner, which allow expression in the host.

In another preferable embodiment, selective markers may be immortalizing genes (for example bcl-2). Alternatively, selective markers may be hypoxanthine guanine phosphoribosyl transferase (hprt), a gene encoding a toxic product, a toxic gene product depending on a condition in combination with a suicide substrate (for example, herpes simplex virus thymidine kinase (HSV-TK) in combination with acyclovir.

In another aspect, the present invention provides a cell comprising the nucleic acid construct according to the present invention. Such a cell, in the case of a lymphocyte, promotes the expression of a protein encoding a foreign gene.

Preferably, it may be advantageous that the cell of the present invention is heterogenous to the promoter sequence of the present invention. It is one of the surprising effects to have promoter activity even if the cell is heterogenous. A method for introducing a nucleic acid into a cell used in the present invention is well known in the art, and described in detail hereinabove. Alternatively, such a cell may be identified by screening a cell comprising the nucleic acid molecule in a sample comprising the same. The cell comprising the nucleic acid molecule according to the present invention may preferably be in an undifferentiated state. The cells expressing the nucleic acid molecule of the present invention is usually in a state of undifferentiation. Accordingly, a cell into which such a nucleic acid molecule has been introduced so as to be expressed in a controllable manner, may be controlled with respect to the undifferentiated state. Alternatively, such a cell may be used to produce a large amount of the nucleic acid according to the present invention. Such production methods are well known in the art and are described in the literature described herein.

In another aspect, the present invention provides a tissue comprising the nucleic acid construct according to the present invention. Such a nucleic acid sequence is preferably operably linked to a control sequence. Such an organ may be an animal tissue, or a tissue of a different organism such as a plant. Alternatively, such a tissue is used to produce a nucleic acid molecule according to the present invention in a large amount. Such a production method is well known in the art, and described in the reference described herein.

In another aspect, the present invention provides an organ comprising the nucleic acid construct according to the present invention. Such a nucleic acid sequence is preferably operably linked to a control sequence. Such an organ may be an animal organ, or an organ of a different organism such as a plant. Alternatively, such an organ is used to product a nucleic acid molecule according to the present invention in a large amount. Such a production method is well known in the art, and described in the reference described herein.

In another aspect, the present invention provides an organism comprising the nucleic acid construct according to the present invention. Such an organism is used to product a nucleic acid molecule according to the present invention in a large amount. Such a production method is well known in the art, and described in the reference described herein.

In another aspect, the present invention provides a pharmaceutical composition comprising the promoter according to the present invention. As used herein, antigen used may be any proteins desired to raise immune response in a host. Such antigens include, but are not limited to, for example, cancer antigen and the like. Accordingly, the pharmaceutical composition according to the present invention may preferably be DNA vaccine.

In another aspect, the present invention provides a pharmaceutical composition for treating a disease, disorder or condition in which a lymphocyte-specific treatment is desired, which comprises the promoter according to the present invention, and a nucleic acid sequence for the treatment. As used herein, the target of the pharmaceutical composition may appropriately be any diseases, disorders, conditions and the like desired to have lymphocyte specific treatment, and are exemplified by acquired immunodeficiency syndromes. Acquired immunodeficiency syndromes include, severe combined immunodeficiency (SCID), MHC I deficiency, MHC II deficiency, Wiskott-Aldrich syndrome, X-linked high IgM syndrome, granuloma telangiectaticum, Bloom's syndrome and the like. Although not wishing to be bound by theory, acquired immunodeficiency syndrome is caused by some deficiency in a recessive gene (which is herein also called a recessive gene to be deleted). It is thus possible to carry out somatic gene therapy in which this gene to be deleted is introduced to bone marrow cells taken from a patient then the cells are reintroduced into the patient. In this regard, the HHV6B MIE promoter of the present invention is likely employed to increase the gene expression efficiency in a cell differentiated into T cell or macrophage and the like. Introduction of such a gene construct is, for example, possible by using retrovirus and the like.

In a preferable embodiment, the nucleic acid sequences for the treatment include a sequence selected from the group consisting of those encoding cytokines, chemokines, growth factors, protein hormones, peptide hormones, ribozymes and siRNA

```
(HIV-1 gp41:
                                       (SEQ ID NO: 33)
AATAAGACAGGGCTTGGAAAGACACTTTCCAAGCCCTGTCTTATTTTT/

HIV-1 tat:
                                       (SEQ ID NO: 34)
AAGCATCCAGGAAGTCAGCCTACAAGGCTGACTTCCTGGATGCTTTTT/

HTLV-1 tax:
                                       (SEQ ID NO: 35)
GAACATTGGTGAGGAAGGCACAGCCTTCCTCACCAATGTTCTTTTT).
```

In another aspect, the present invention provides a method for expressing a protein in a lymphocyte specific manner, comprising the steps of: A) preparing a nucleic acid construct in which the promoter according to the present invention is operatively linked to a nucleic acid sequence encoding the protein; and B) placing the nucleic acid construct under a condition in which the promoter induces the expression of the nucleic acid sequence encoding the protein.

In another aspect, the present invention provides a kit for expressing a protein in a lymphocyte specific manner, comprising: A) a nucleic acid construct in which the promoter according to the present invention is operatively linked to a nucleic acid sequence encoding the protein; and B) means for placing the nucleic acid construct under a condition in which the promoter induces the expression of the nucleic acid sequence encoding the protein.

In another aspect, the present invention further provides a kit for expressing a protein in a lymphocyte specific manner, comprising: A) the promoter according to the present invention; and B) means for producing a nucleic acid construct in which the promoter is linked to a nucleic acid sequence encoding the protein.

In another aspect, the present invention further provides a method for treating or preventing a disease, disorder or condition which requires the expression of a protein in a lymphocyte specific manner, comprising the steps of: A) producing a nucleic acid construct in which the promoter according to the present invention is linked to a nucleic acid sequence encoding the protein; and B) placing the nucleic acid construct under a condition in which the promoter induces the expression of the nucleic acid sequence encoding the protein.

In another aspect, the present invention further provides a kit for treating or preventing a disease, disorder or condition which requires the expression of a protein in a lymphocyte specific manner, comprising: A) a nucleic acid construct in which the promoter according to the present invention is linked to a nucleic acid sequence encoding the protein; and B) means for placing the nucleic acid construct under a condition in which the promoter induces the expression of the nucleic acid sequence encoding the protein.

In another aspect, the present invention further provides a kit for treating or preventing a disease, disorder or condition which requires the expression of a protein in a lymphocyte specific manner, comprising: A) the promoter according to the present invention; and B) means for producing a nucleic acid construct in which the promoter is linked to a nucleic acid sequence encoding the protein.

In another aspect, the present invention further provides a method for producing a protein, comprising the steps of: A) preparing a nucleic acid construct in which the promoter according to the present invention is linked to a nucleic acid sequence encoding the protein; and B) placing the nucleic acid construct under a condition in which the promoter induces the expression of the nucleic acid sequence encoding the protein.

In another aspect, the present invention further provides a kit for producing a protein, comprising: A) a nucleic acid construct in which the promoter according to the present invention is linked to a nucleic acid sequence encoding the protein; and B) means for placing the nucleic acid construct under a condition in which the promoter induces the expression of the nucleic acid sequence encoding the protein.

In another aspect, the present invention further provides a kit for producing a protein, comprising: A) the promoter according to the present invention; and B) means for producing a nucleic acid construct in which the promoter is linked to a nucleic acid sequence encoding the protein.

In another aspect, the present invention further provides use of the promoter according to the present invention, for manufacture of a pharmaceutical composition for treating or preventing a disease, disorder or condition which requires the expression of a protein in a lymphocyte specific manner.

All scientific literature, patents, published patent applications and publications cited herein are incorporated by reference as if set forth fully herein.

The preferred embodiments of the present invention have been heretofore described for a better understanding of the present invention. Hereinafter, the present invention will be described by way of examples. Examples described below are provided only for illustrative purposes. Accordingly, the scope of the present invention is not limited except as by the appended claims.

EXAMPLES

Handling of animals used in the following Examples are in accordance with the provisions set forth in Osaka University.

Example 1

Search for HHV6B Promoters and Development of DNA Vaccines

With respect to promoters of immediate early protein of HHV-6 (9U, 20U, MIE, U95, MIE/3K, U95/3K, which are different in size), the activity thereof was compared to that of cytomegalovirus (CMV) promoter. With respect to methods, the respective promoter regions were inserted upstream of the luciferase gene of pGL3-Basic Vector (Promega), which were transfected with the respective cells to compare the activity thereof using luciferase activity as reference. Hereinafter, the details of materials and methods are described.

(Materials and Methods)
(Outline)

The promoter region of MIE gene of HHV-6B (about 1.2 kbp) was cloned, which was linked to an outer membrane glycoprotein of Japan encephalitis virus Beijing-1 strain cDNA downstream thereof to construct the plasmid p9u/JEVenv. Green fluorescence protein expression plasmid pEGFP-N1 used was commercially available (available from Clontech).

It was constructed using a plasmid (pcDNA3.1/JEVenv) as reference in which JEVenv was linked downstream of HCMV-IE promoter of pcDNA3.1Zeo+ vector. Green fluorescence protein expression plasmid pEGFP-N1 used was commercially available (available from BD Biosciences). Furthermore, luciferase expression plasmid used herein was that which has already been constructed (pGL3-Basic; available from Promega).

These plasmids were introduced to the following cells: 293 cell (derived from human kidney), Vero cell (derived from simian kidney), SupT1 cell (derived from human T lymphocyte), U937 cell (derived from human monocyte) and the like (these cells are available from American Type Culture Collection (ATCC), RIKEN Cell Bank, Gene banks and the like). The expression of outer membrane glycoprotein in a cell was studied using indirect fluorescence antibody method using anti-JEV polyclonal antibody, and Western blot with cell extract thereof.

HHV-6MIE promoter region was inserted upstream of firefly luciferase gene of luciferase vector pGL3-Basic (Promega) to form p9u, which was used to prepare truncated mutants by removing bases by Mung Bean Exonuclease from upstream of MIE promoter.

Vero cell was transfected with these truncated mutants and Renilla luciferase expression plasmid for transfection efficiency correction (phRL-SV40) by the lipofection method. Cells were collected 24 hours after the transfection, and cell lysis solution was added thereto. Thereafter, luminescent level was measured in the firefly luciferase and Renilla luciferase in the lysate. In order to correct the efficiency of transfection, the luminescence level of the firefly luciferase was divided by that of Renilla luciferase.

1) Cells—The following eight types of cell lines were used for promoter activity measurement.
  (1) Vero cell (derived from simian kidney)
  (2) HEL cell (derived from human embryonic fibroblast cell)
  (3) L929 cell (derived from murine fibroblast cell)
  (4) 293 cell (derived from human kidney)
  (5) U373 cell (derived from human glioma)
  (6) THP-1 cell (derived from human monocyte)
  (7) SupT1 cell (derived from human T cell)
  (8) U937 cell (derived from human monocyte)
(These cells are available from American Type Culture Collection (ATCC)).

2) Plasmids for the Measurement of Promoter Activity

In order to measure promoter activity, pGL3-Basic (Promega) having firefly luciferase gene was used. This plasmid has no promoter sequence or enhancer sequence derived from eukaryotic cells, a variety of base sequences are introduced upstream of the luciferase gene, and the amount of luciferase expressed is measured to allow measurement of the promoter activity of the inserted sequence.

3) Promoter Sequence with pGL3-Basic Incorporated Therein

For measurement, as described below, HHV-6MIE promoter region, the promoter region of U95 gene, an immediate early gene of HHV-6 and HCMV MIE promoter region as commercially available expression vectors were used.

HHV-6 promoter region was used after proliferating by PCR and having inserted into pGL3-Basic.

(1) 20u [one with HHV-6MIE promoter region (139381←140624:1243 bp) inserted thereinto] (SEQ ID NO: 5)

(2) 9u [one with HHV-6MIE promoter region (139381←140427:1046 bp) inserted thereinto] (SEQ ID NO: 6)

(3) MIE [one with HHV-6MIE promoter region (139457←140211:754 bp) inserted thereinto] (SEQ ID NO: 7)

(4) U95 [one with HHV-6 U95 gene promoter region (141823→142578:756 bp) inserted thereinto] (SEQ ID NO: 8)

(5) CMV [one with HCMV MIE promoter excised from commercially available expression vector (pcDNA3.1) inserted thereinto: 750 bp] (SEQ ID NO: 9)

(6) MIE/3K [one with HHV-6MIE promoter region (139443←142578:3136 bp) inserted thereinto] (SEQ ID NO: 10)

(7) U95/3K [one with HHV-6MIE promoter region (139443→142578:3136 bp) inserted thereinto] (SEQ ID NO: 11), as a control, intact pGL3-Basic with no base sequence inserted was used.

Figure 5:
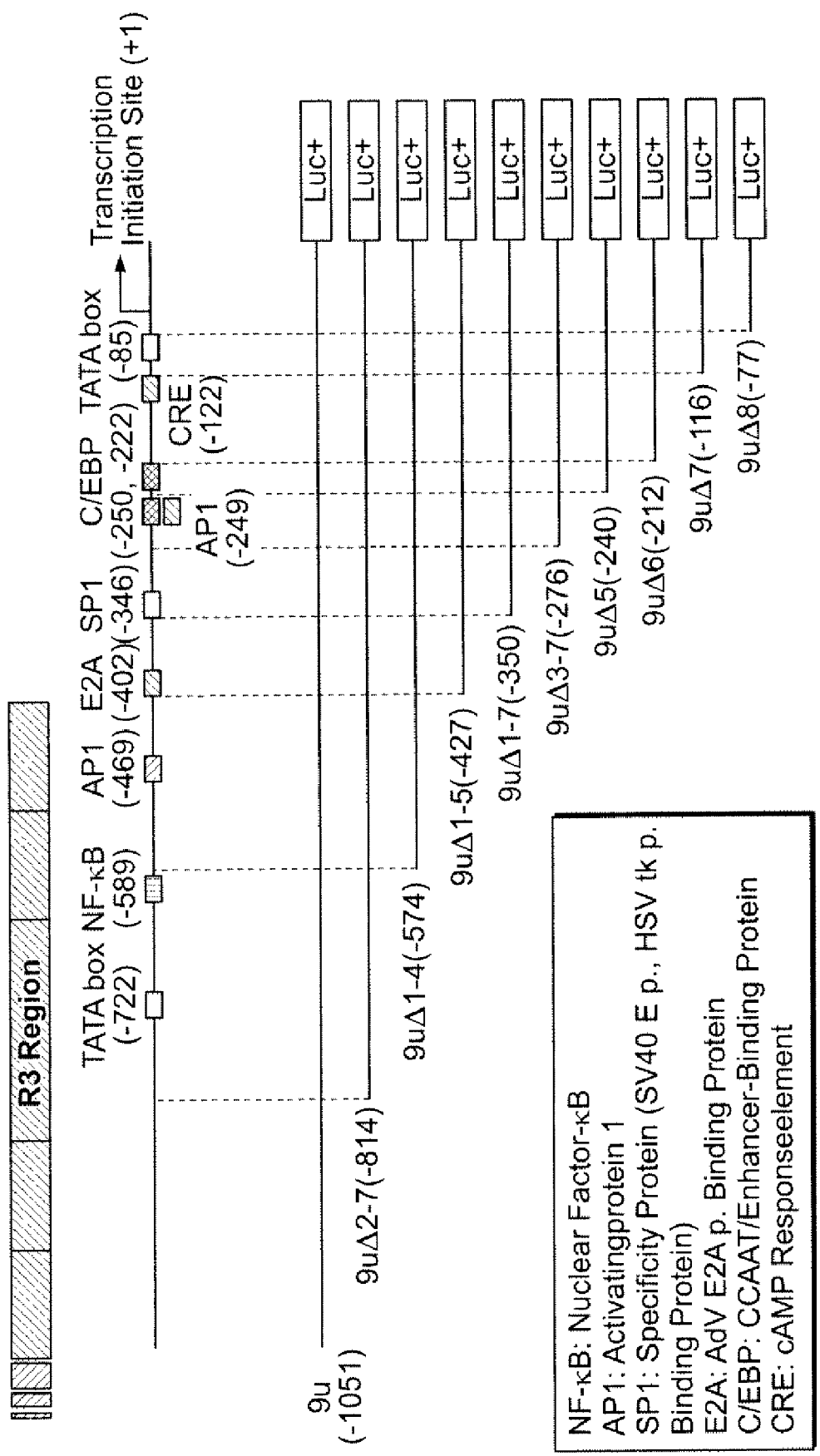
FIG. 5 depicts illustrations of a variety of deletion variants in a promoter region of the HHV6B. The upper panel shows the promoter region, and a variety of motifs in the promoter regions.
Figure 6:
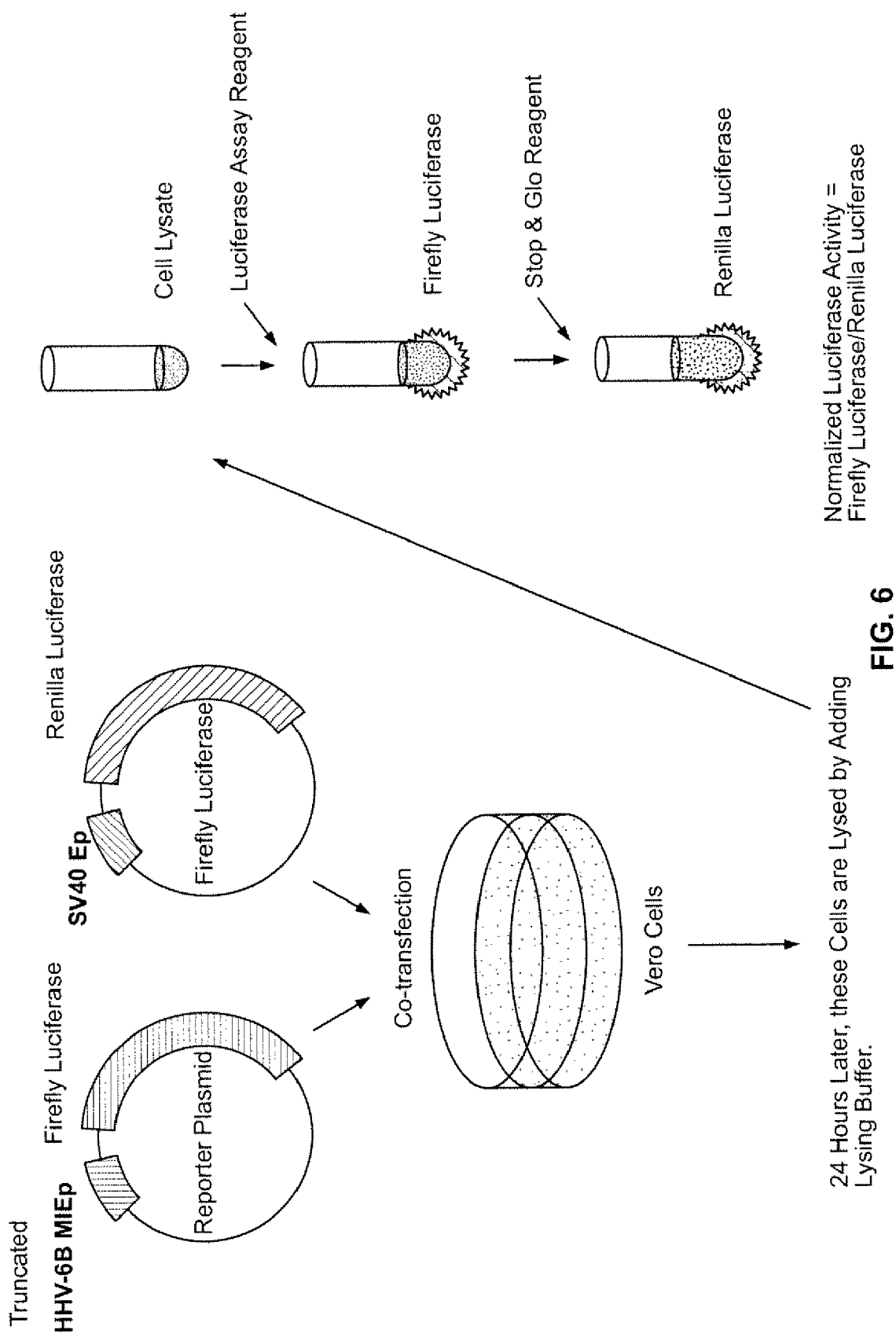
FIG. 6 depicts a measurement system for promoter activity.

Furthermore, a variety of deletion variants were produced. These schematic figures are shown in FIG. 5. As variants, the following products were prepared as shown in FIG. 5.
  (1) 9u: −1051 to +1 (SEQ ID NO: 5)
  (2) 9u-d2-7: −814 to +1 (SEQ ID NO: 17)
  (3) 9u-d1-4: −574 to +1 (SEQ ID NO: 18)
  (4) 9u-d1-5: −427 to +1 (SEQ ID NO: 19)
  (5) 9u-d1-7: −350 to +1 (SEQ ID NO: 20)
  (6) 9u-d3-7: −276 to +1 (SEQ ID NO: 21)
  (7) 9u-d5: −240 to +1 (SEQ ID NO: 22)
  (8) 9u-d6: −212 to +1 (SEQ ID NO: 23)
  (9) 9u-d7: −116 to +1 (SEQ ID NO: 24)
  (10) 9u-d8: −77 to +1 (SEQ ID NO: 25)

4) Transfection of a Cell with a Plasmid Transfection was conducted with Lipofection method using SuperFect (QIAGEN).

In order to correct transfection efficiency, expression plasmids of β-galactosidase (pCH110, Pharmacia) were simultaneously introduced to a cell, and β-galactosidase activity was measured. pCH110 expresses β-galactosidase under control of the early promoter of SV40.

pGL3 construct (8 μl) and pCH110 (0.2 μl) were mixed together and Superfect reagent (8 μl) was added thereto to conduct transfection.

5) Measurement of Luciferase Activity

Luciferase activity was measured using Luciferase Assay System (Promega).

pGL3 construct and pCH110 were cotransfected, and 48 hours later, the cells were recovered. After twice washing with PBS, it was dissolved into 150 μL of cell lysis solution. One hundred μL of luciferase substrate solution was added to the cell lysis solution supernatant (20 μL), and thirty seconds later, luminescence was measured with a luminometer.

6) Measurement of β-galactosidase Activity

B-galactosidase activity was measured using β-gal reporter system (Clontech). To twenty μL of cell lysis solution prepared in a similar manner as in the luciferase activity measurement was added 100 μL of luminescent substrate solution, and luminescence was measured after one hour using a luminometer.

7) Measurement of Promoter Activity Under Conditions where Cells were Activated with TPA The plasmids were transfected with Vero cells and L929 cells, and 24 hours later, the cultures were conducted in the presence and absence of TPA (25 ng/ml) for an additional 24 hours. Thereafter, the cells were collected, and measured for the activity of luciferase and β-galactosidase.

(Results)

1) Promoter activity of the HHV-6 MIE region:

Promoter activity of HHV-6 MIE region and promoter activity of HCMV MIE showed different behaviour in endothelial adhesive cells and lymphocyte cells.

(1) Comparison of Promoter Activities in Adhesive Cells (FIG. 1)

The promoter sequence of HHV-6MIE had weaker activity than HCMV in adhesive cells, with some promoter activity. The promoter of U95, a HHV-6 immediate early gene, showed little activity. On the other hand, HCMV MIE promoter showed about 10 to 50 fold more activity than that of HHV-6 MIE promoter in adhesive cells. In particular, in HEL cells and U373 cells, HCMV proliferation competent cells, it showed potent activity.

With respect to the promoter activity of the HHV-6 MIE region, those having the promoter region from 0.7 kb to 1.2 kb in length showed substantially the same activity, but reduction in the activity was recognized in the sequence of 3 kb.

Figure 2:
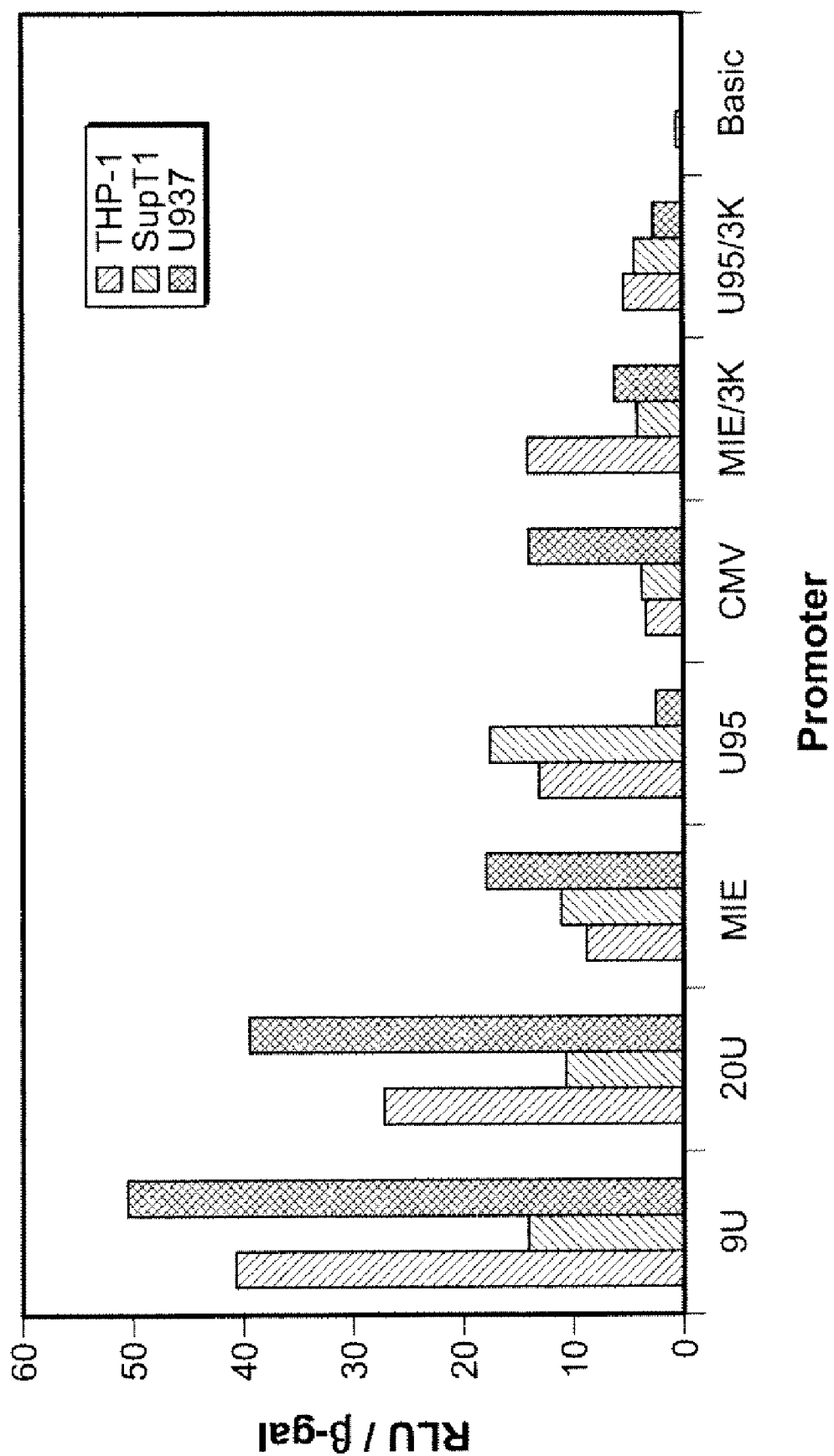
FIG. 2 depicts the comparison of promoter activities in lymphocytes. The x-axis aligns a variety of promoters, and the promoter activities of the THP-1 cell, the SupT1 cell and the U937 cell are shown using Log(RLU)/β-gal with logarithmic reference.

(2) Comparison of Promoter Activities in Lymphocyte Cells (FIG. 2)

In lymphocyte cells which are proliferation competent cells of HHV-6, the HHV-6 MIE region showed about ten times higher promoter activity than HCMV. In particular, it showed potent activity in THP-1 and U937 which are cell lines of monocytic macrophages. HCMV MIE promoter did not exhibit so strong activity in lymphocytes.

The promoter activity of the HHV-6 MIE region increased the activity thereof in accordance with the length from 0.7 kb to 1.2 kb in the promoter region, however, the length of 3 kb reduced its promoter activity.

Figure 3:
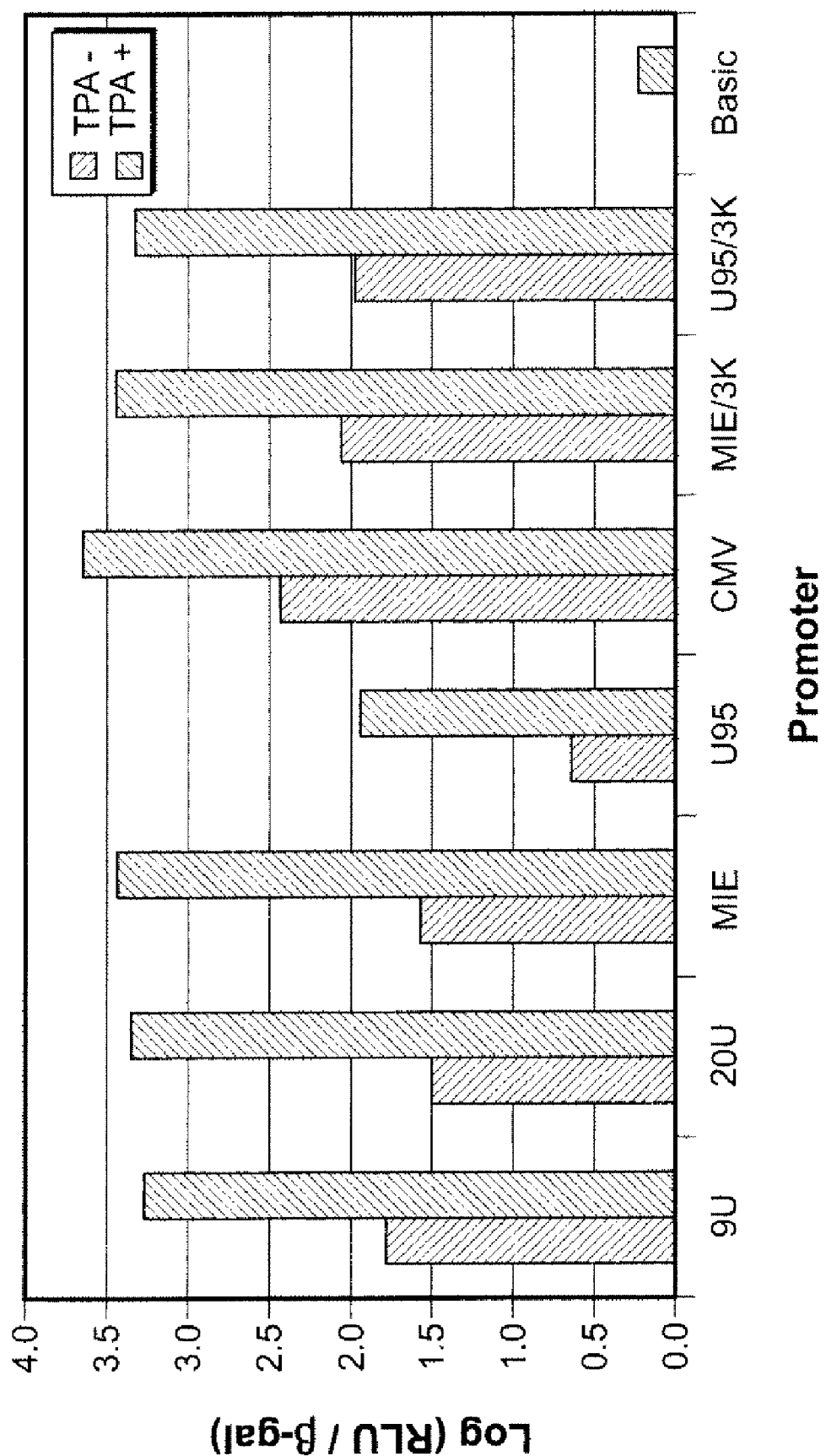
FIG. 3 depicts the promoter activity of the HHV-6 MIE region in the case of stimulating a cell with TPA (Vero cell). On the x-axis, a variety of promoters are aligned, and the activity of a promoter with and without TPA is shown using Log(RLU)/β-gal in a logarithmic manner.
Figure 4:
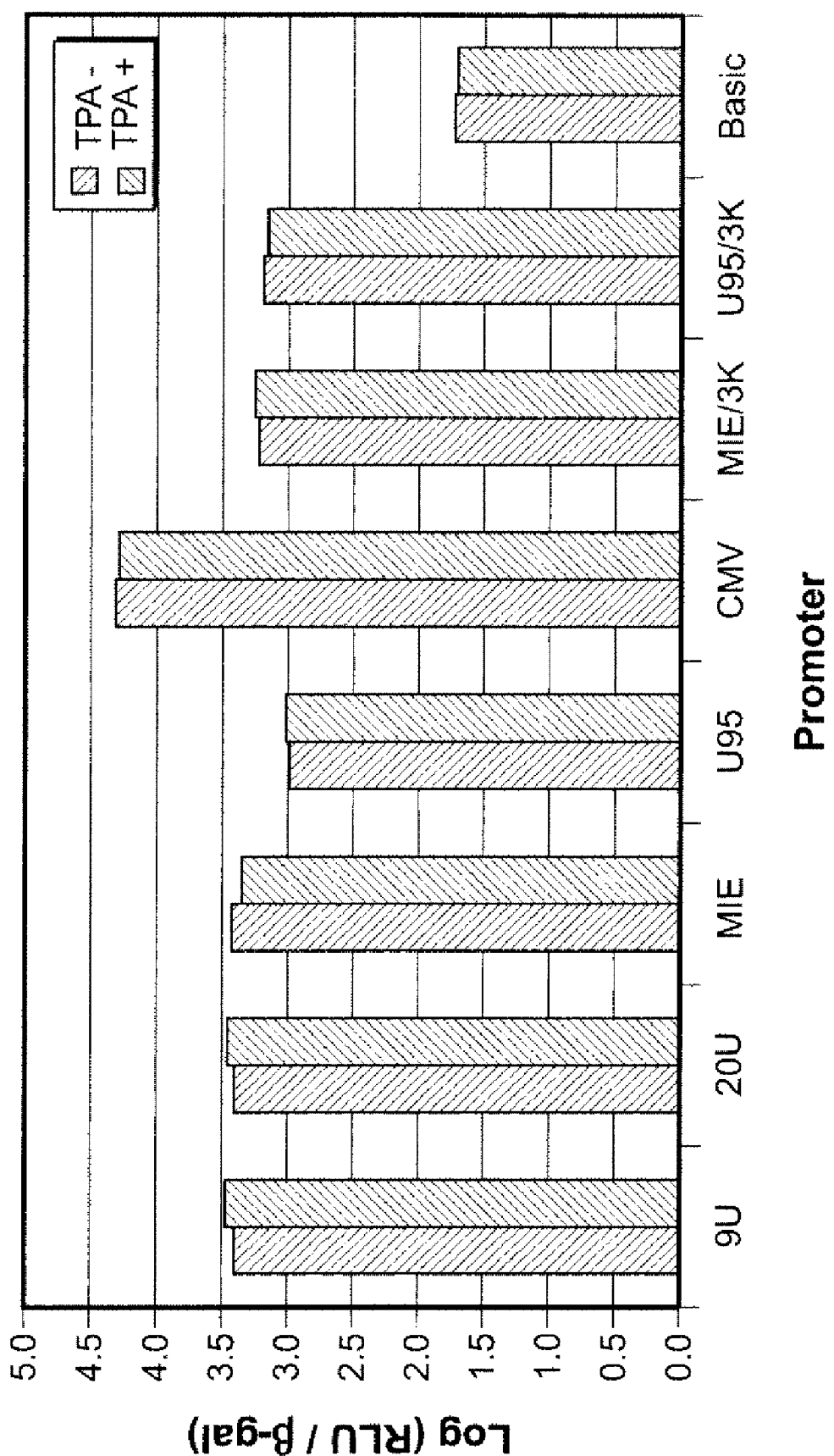
FIG. 4 depicts promoter activity of the HHV-6 MIE region (L929 cell) when the cell has been stimulated with TPO. On the x-axis, a variety of promoters are aligned, and the promoter activity in the presence or absence of TPA with respect to the respective promoters is depicted using Log(RLU)/β-gal in a logarithmic manner.

2) Promoter activity of the HHV-6 MIE region when stimulated by a cell with TPA (FIGS. 3 and 4)

Vero cells were stimulated with 12-O-tetradecanoyl phorbol 13-acetate (TPA) to measure the promoter activity of HHV-6 MIE, and all promoter activities were increased, and showed substantially the same level as that of HCMV MIE promoter (FIG. 3).

However, in L929 cells, no increase in promoter activity was observed upon cell activation with TPA stimulation (FIG. 4). This is believed to be due to the difference in reactivity of TPA on cell type.

In Vero cells, it is believed that TPA increased the HHV-6 MIE promoter activity by inducing a large amount of a variety of transcriptional activation factors. That is, the maximum activity of HHV-6 MIE promoter is as much as HCMV MIE promoter. Therefore, the promoter of the present invention has been demonstrated with respect to its specificity and selectivity.

As such, in the present invention, adhesive cells such as Vero cells, HEL cells, L929 cells, 293 cells, U373 cells, CMV promoters showed ten times more potent activity than that of HHV-6 (FIG. 1). However, in cells derived from human lymphocytes such as THP-1 cells, SupT1 cells, U938 cells, several times as much activity as that of CMV promoter was observed in HHV-6 promoter, and it was also observed that the more truncated, the more potent activity was found.

Promising promoters from HHV-6 have been confirmed, and from these results, it is understood that these promoters can be applied to DNA vaccines (mumps vaccines) and are extremely promising.

HCMV IE promoter was used as a control to compare and study the HHV-6B MIE promoter activity which has been cloned by the present inventors, in a luciferase expression system. As a result, in adhesive cells such as 293 cells, Vero cells and the like, HHV-6MIE promoter only showed about one tenth as much activity as that of HCMHE promoter. However, in lymphocyte cells such as SupT1, and U937 and the like, it was found that several times greater expression efficiency was obtained. Conducting an assay on the expression of the outer membrane glycoprotein of JEV by using p9u/JEVenv linked to JEV cDNA downstream of the subject promoter, no expression of the JEV protein was detected in any adhesive cells or flowing lymphocytes after 48 hours of transfection.

On the other hand, in pcDNA3.1/JEVenv using the IE promoter of HCMV, the expression of JEV protein was confirmed.

Moreover, in JEV infected Vero cells, which were used as a positive control, outer membrane glycoprotein was readily detected. In order to analyze the cause, transfection efficiency was confirmed using GFP protein expression plasmids. As a result, the introduction efficiency in SupT1 cell was as low as 0.1% or less, however, adhesive 293 cells and Vero cells had a higher introduction efficiency of 45% and 20%, respectively. HHV-6 MIE promoter cloned, showed a several times higher expression activity than HCMV MIE promoter in lymphocyte cells. However, expressed gene was not detected with its activity when it was converted to outer membrane glycoprotein of JEV.

It is of interest that the HHV-6 MIE promoter cloned herein showed several times higher expression activity than that of the HCMV-IE promoter in lymphocytes. However, it was unpredictable that when the gene to be expressed had been converted to outer membrane glycoprotein of JEV from the reporter gene, no activity was detected. Therefore, the cause thereof was analyzed as to whether expressed JEV protein acted in a feedback manner, and thus the promoter activity was inhibited in an adverse manner, or that alternatively the expressed antigen is unstable in these cells.

The present Example is summarized as follows:

1) HHV-6 MIE promoter showed about ten times higher activity than HCMV MIE promoter in lymphocyte cells, in particular, monocyte/macrophage cells.

2) In epithelial adhesive cells, HHV6 MIE promoter activity was about one tenth of that of HCMV MIE promoter.

3) HHV-6 MIE promoter is suggested to exhibit substantially the same activity as HCMV MIE promoter under conditions where a large amount of a variety of transcriptional factors was induced.

As described above, in the present Example, those which were inserted about 12 kbp (6MIEP) upstream of the major immediate early (MIE) gene of HHV-6B and about 700 bp upstream of U95 gene (6U95) upstream of the luciferase gene of pGL3Basic vector (Promega) were used. In comparison to the conventional promoters, in order to study the possibility of the application of these IE promoters to DNA vaccines, comparison with human cytomegalovirus '(HCMV) IE enhancer-promoter (CMVP) in activity were conducted using blood cell lineage cells. In the present Example, immediate early (IE) promoter encoded by human herpes virus 6B (HHV-6B) was demonstrated to have extremely high activity in blood cell lineage cells.

Figure 7:
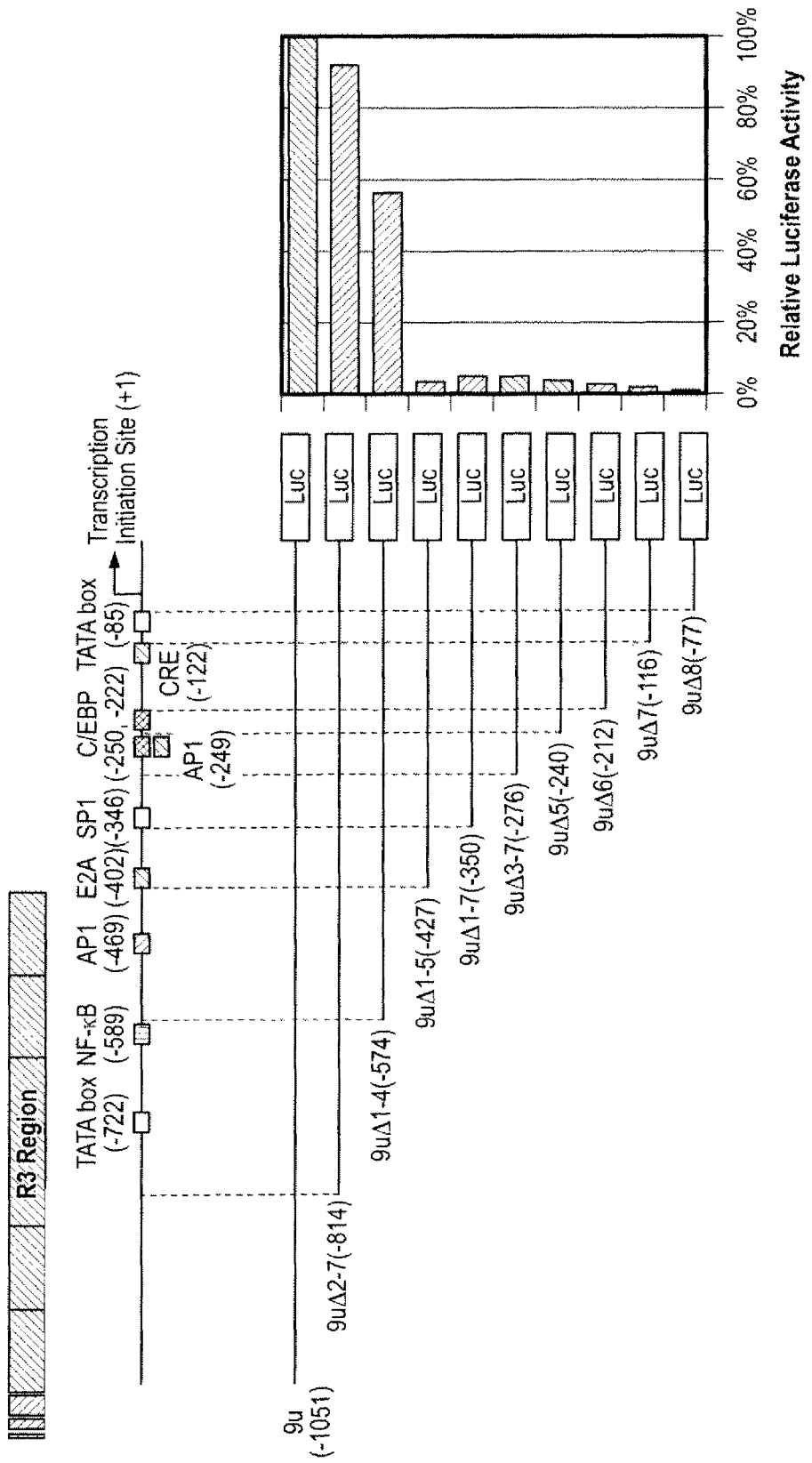
FIG. 7 depicts the promoter activity (relative luciferase activity) with illustrations of a variety of deletion variants in the promoter region in the HHV6B.

4) Furthermore, as depicted in FIG. 7, it was shown that activities in the respective fragments were investigated, and at least −572 to −427 and in particular −1051 to −427 upstream of the initiation point have promoter activity with preferable enhancer activity. The site of −417 to +1 appears to be necessary for promoter activity, and the enhancer activity appears to be necessary to secure specificity. The portions responsible for enhancer activity are elucidated to have NF-κB and AP-1 motifs. Therefore, it appears that it is important to have these motifs in order to have specificity in lymphocytes.

Example 2

MIE and U95 Promoters of HHV-7

Next, experiments relating to promoters from HHV-7 were conducted.

The activity of two immediate early promoters of HHV-7 (7MIEP, 7U95P) were compared with the activity of cytomegalovirus (CMV) promoter and HHV-6 IE promoter (9U and U95). Methods of comparison are as follows: the respective promoter regions were inserted upstream of the luciferase gene of pGL3-Basic Vector (Promega), which were transfected with the respective cells to compare the activity thereof using luciferase activity as reference. In order to study the effects of the R2 region present upstream of the respective promoters, a variety of deletion variants have been prepared to measure promoter activity.

(Outline)

As a reporter plasmid, about 500 bp from the respective MIE and u95 genes of HHV-7 (7MIEP and 7U95P) were inserted upstream of luciferase gene of pGL3Basic vector (Promega) and used in the present Example.

A reporter plasmid was introduced to T cell lines (Jurkat, Molt-3, SupT-1), and bone marrow cell line (SAS-413) with lipofection methods, and to peripheral blood monocytic cells (PBMC) with electroporation, and luciferase activity was measured. As a result, in comparison with HCMV MIE promoter, HHV-7 MIE promoter and HHV-7 U95 promoter showed several times higher activity than HCMV MIE promoter in T cell lines, and in SAS-413 cells, HCMV MIE promoter has more than ten times higher activity. In the experiment where introduction was made to three lots of PBMC, HHV-7 MIE promoter and HHV-7 U95 promoter showed low activity. In comparison with HHV-6 IE promoters (9U and U95), both promoters of HHV-7 showed lower activity in any cell species. Further, in the experiments with the deletion mutants of the respective HHV7 MIE promoter and HHV7 U95 promoter, it was shown that although there is some difference from cell type to cell type, R2 is responsible for major enhancer activity against both promoter's activity. In the present Example, it was demonstrated that immediate early (IE) promoter encoded by human herpes virus 7 (HHV-7) has extremely high activity in blood cell lineage cells.

Hereinafter, materials and methods are described in detail.

(Materials and Methods)

1) Cells—The following five types of cells were used for measuring promoter activity.

(1) Jurkat cell (derived from human T cell)
(2) Molt-3 cell (derived from human T cell)
(3) SupT1 cell (derived from human T cell)
(4) SAS-413 cell (derived from human bone marrow cell)
(5) peripheral blood monocytic cells (PBMC)

2) Plasmids for Measuring Promoter Activity pGL3 Basic (Promega) having Firefly luciferase gene was used for measuring promoter activity.

3) Promoter Sequences Inserted into pGL3 Basic

Figure 8:
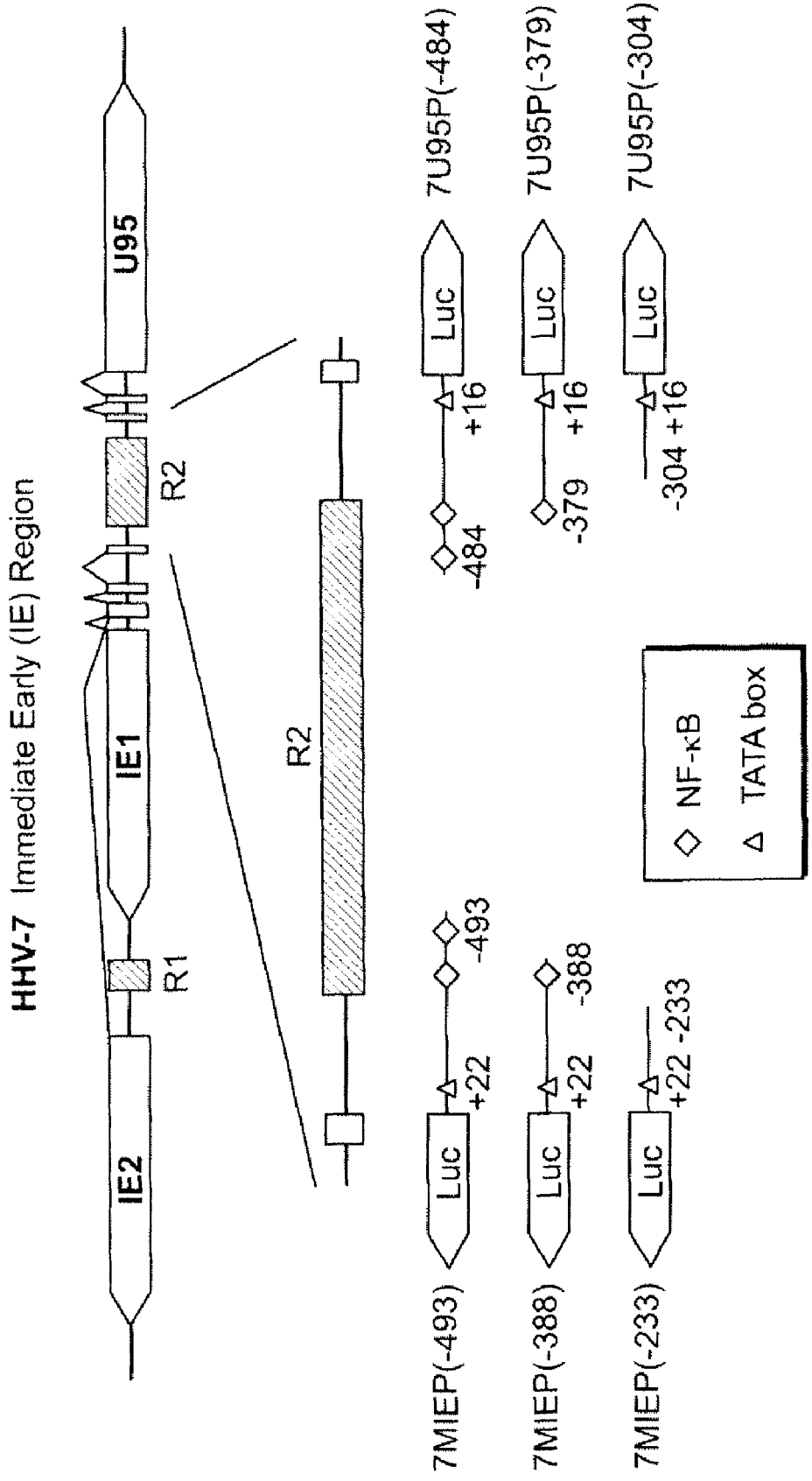
FIG. 8 depicts illustrations of the immediate early (IE) gene relating to the promoter region of the HHV7 and the promoter thereof. The left column shows, from the top, 7MIE promoter (−493), 7MIE promoter (−388), and 7MIE promoter (−233), and the right column shows, from the top, 7U95 promoter (−484), 7U95 promoter (−379), and 7U95 promoter (−304).

HHV-7 MIE gene promoter region (7MIEP) and HHV-7 U95 gene promoter region (U95P) were amplified to about 500 bp by PCR, and deletion mutants were prepared for each. These are schematically illustrated in FIG. 8.

(1) 7MIEP(−493) [one inserted with upstream 493 pb to downstream 22 bp from the transcription initiation point of HHV-7 MIE gene] (SEQ ID NO: 26)

(2) 7MIEP(−388) [one inserted with upstream 388 pb to downstream 22 bp from the transcription initiation point of HHV-7 MIE gene] (SEQ ID NO: 27)

(3) 7MIEP(−233) [one inserted with upstream 233 pb to downstream 22 bp from the transcription initiation point of HHV-7 MIE gene] (SEQ ID NO: 28)

(4) 7U95P(−484) [one inserted with upstream 484 pb to downstream 16 bp from the transcription initiation point of HHV-7 U95 gene] (SEQ ID NO: 29)

(5) 7U95P(−379) [one inserted with upstream 379 pb to downstream 16 bp from the transcription initiation point of HHV-7 U95 gene] (SEQ ID NO: 30)

(6) 7U95P(−304) [one inserted with upstream 304 pb to downstream 16 bp from the transcription initiation point of HHV-7 U95 gene] (SEQ ID NO: 31)

pGL3 Basic without promoter sequence has been used as a control.

4) Transfection of Cell with Plasmids

Transfection was conducted regarding Jurkat cell, Molt-3 cell, SupT1 cell, and SAS-413 cell with lipofection using Lipofectamine 2000 (Invitrogen), and regarding PBMC, using electroporation with Nucleofector (amaxa).

In order to correct transfection efficiency, expression plasmids of *Renilla* luciferase (pRL-TK, Promega) were simultaneously introduced to a cell, and *Renilla* luciferase activity was measured. pRL-TK expresses *Renilla* luciferase under control of herpes simplex virus thymidine kinase (TK) promoter.

pGL3 reporter (1.2 μg) and pRL-TK (50 ng) were mixed together and 2 μl of Lipofectamine 2000 were added thereto to conduct transfection.

5) Measurement of Luciferase

For the measurement of luciferase activity, Dual-Luciferase Reporter Assay System (Promega) was used.

The cells were collected 16 hours after the transfection, and were lysed in cell lysis solution (100 μl) To Five μl of supernatant of cell lysis solution, firefly luciferase substrate solution (25 μl) was added, and immediately thereafter, luminescence was measured using a luminometer. Next, to the sample after the measurement, *Renilla* luciferase substrate solution (25 μl) was added and immediately thereafter, luminescence was measured using a luminometer.

(Results)

1) Activity of Promoter Region of HHV-7 MIE

Figure 9:
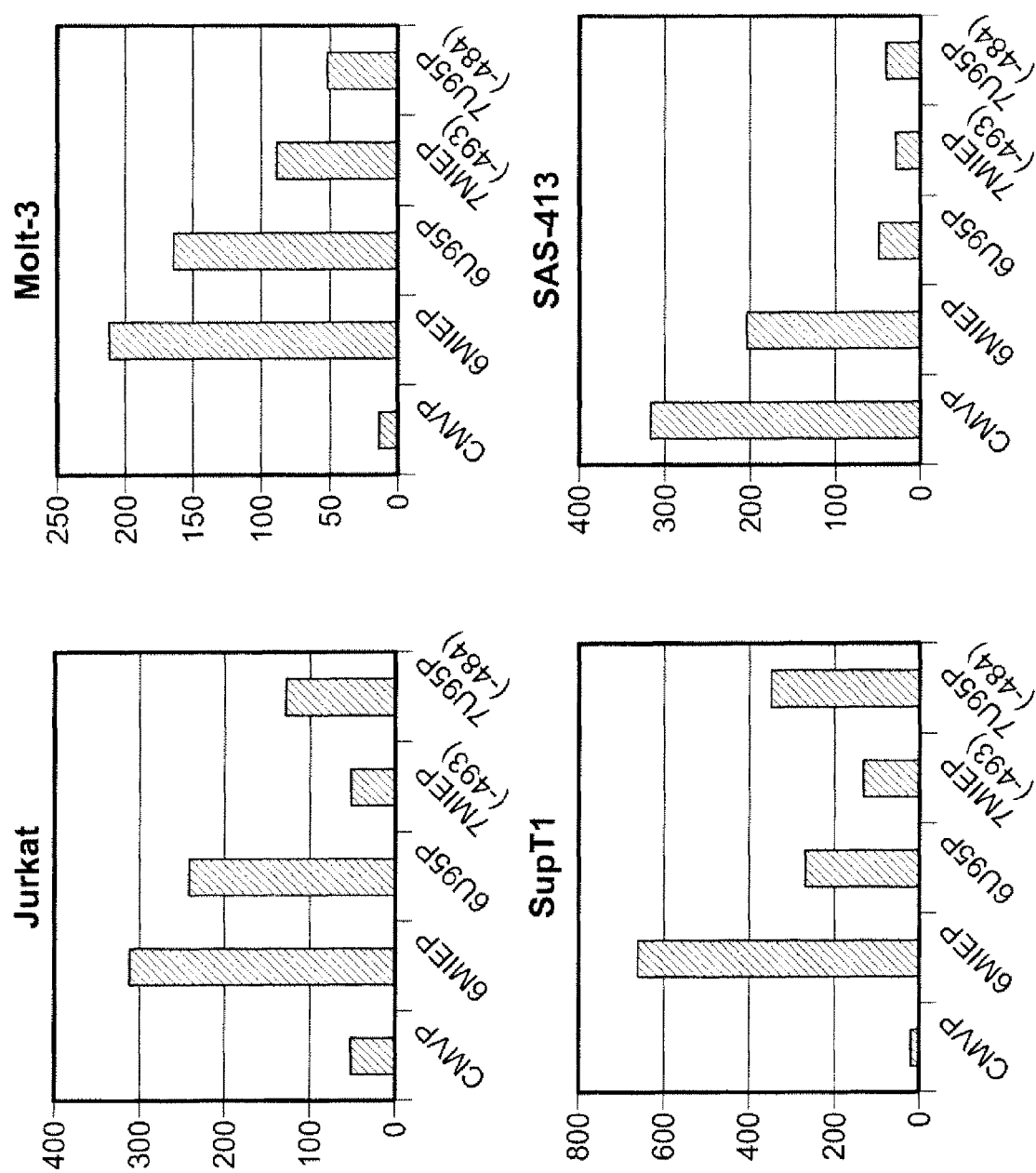
FIG. 9 depicts the activity of the IE promoter of the HHV7 in a lymphocytic cell line. The upper left graph shows Jurkat cells, the upper right graph shows Molt-3 cells, the lower left graph shows SupT1 cells, and the lower right graph shows SAS-413 cells. Each graph shows, from the left, CMVP, 6MIEP, 6U95P, 7MIE(−493), 7U95 and P(−484), respectively.

As a result of experiments using four types of cell lines, when compared with the activity of CMV promoter, 7MIEP (−493) showed about 6-7 times higher activity in Molt-3 cell and SuptT1 cell, similar activity in Jurkat cells, and about 1/11 activity in SAS-413 cells. Moreover, when comparing with HHV-6 IE promoters (9U and U95), in all cell types, 7MIEP (−493) showed lower activity (FIG. 9).

Figure 10:
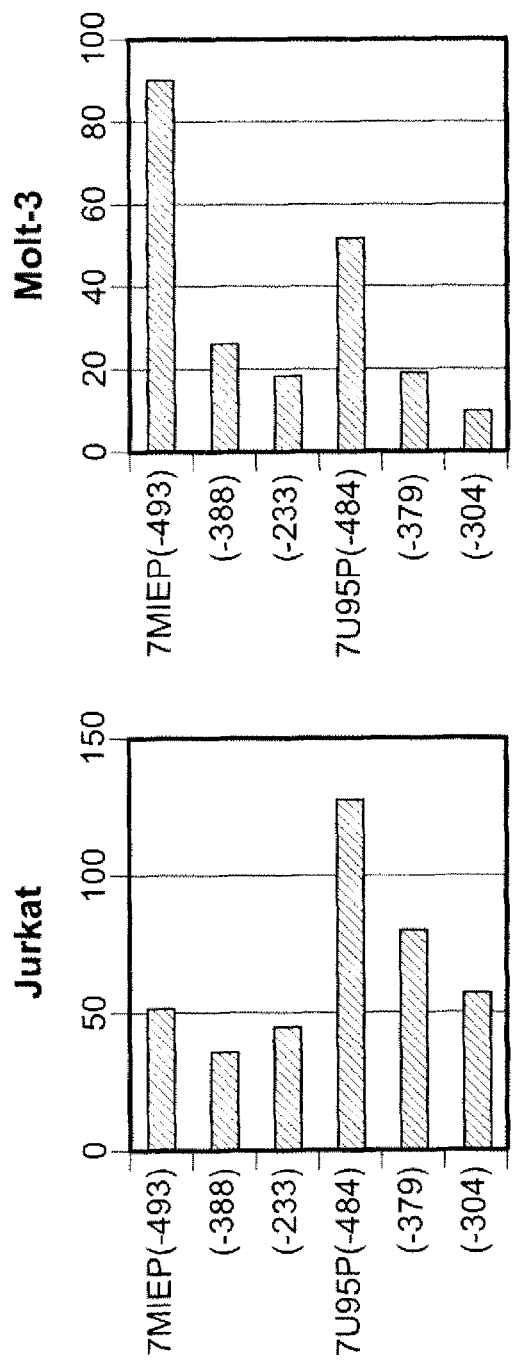
FIG. 10 depicts the effects of R2 deletion on promoter activity. The upper left graph shows Jurkat cells, the upper right graph shows Molt-3 cells, the lower left graph shows SupT1 cells, and the lower right graph shows SAS-413 cells. The graphs show from the left, 7MIE promoter (−493), 7MIE promoter (−388), 7MIE promoter (−233), 7U95 promoter (−484), 7U95 promoter (−379) and 7U95 promoter (−304).
Figure 10:
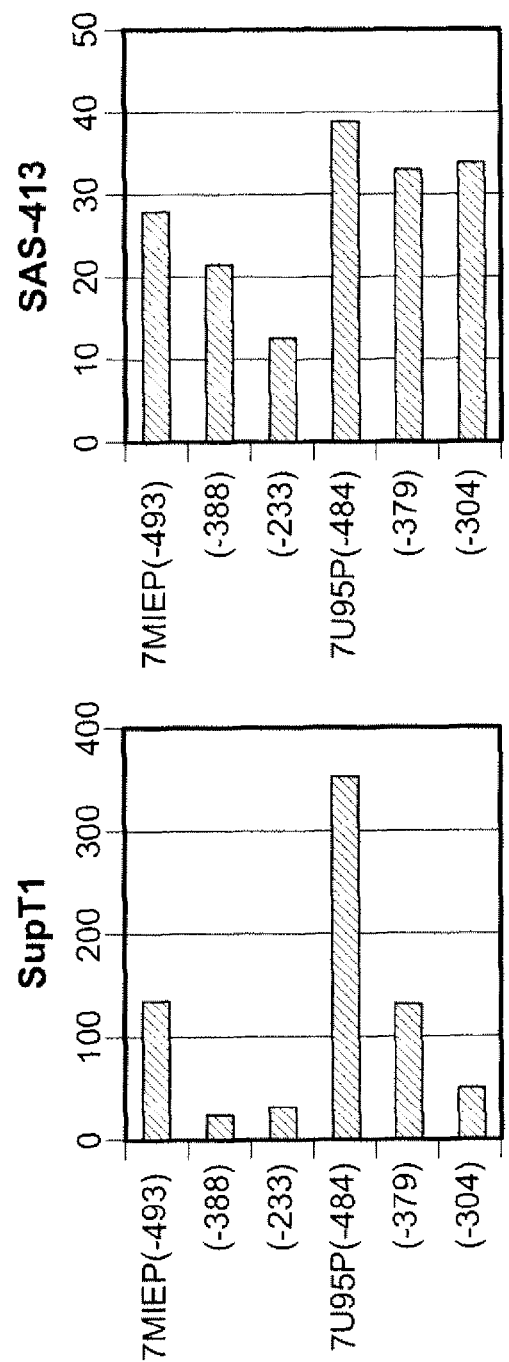

As a result of experiments using three lots of PBMC, the activity of 7MIEP (−493) was similar or slightly lower than CMV promoter and 9U, and similar or slightly higher than HHV-6 U95 (FIG. 10).

2) Activity of HHV-7 U95 Promoter Region

As a result of experiments using four types of cell lines, when compared with the activity of CMV promoter, 7U95P (−484) showed about 2.5 times higher activity in Jurkat cells, four time in Molt-3 cells, twenty times in SupT cells, however, about 1/8 activity in SAS-413 cells. Moreover, when comparing with HHV-6 IE promoters (9U and U95), U95P(−484) showed slightly higher activity in SupT1 than U95, however, was about 1/2 of that of 9U, and showed lower activity in other cells (FIG. 9).

In an experiment where three lots of PBMC were used, 7U95P(−494) showed only about 1/2 to 1/4 as much promoter activity as that of the others. (FIG. 10).

3) Effects of the R2 Region on Promoter Activity

Figure 11:
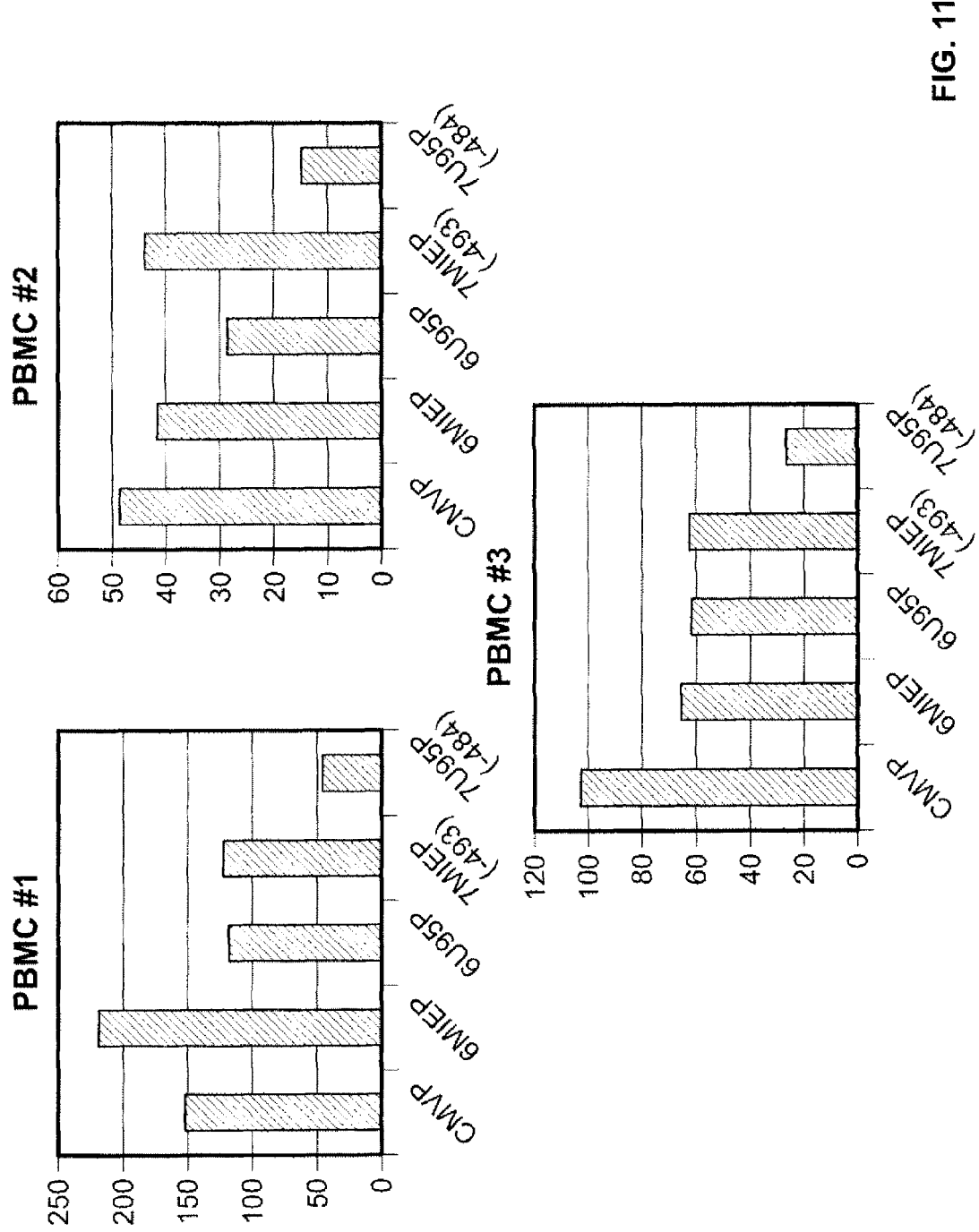
FIG. 11 depicts the promoter activity in a peripheral blood monocytic cell (PBMC). It shows lineage 1, lineage 2 and lineage 3, in the upper left, upper right and lower panels, respectively.

It was elucidated as a result of an experiment where the respective deletion mutants of 7MIEP and 7U95P were introduced into four types of cell lines, that it depends on the type of cell whether the promoter activity is lowered by the deletion of R2. Specifically, 7MIEP showed no effects with the R2 deletion in Jurkat cells, but reduced its activity by about 1/5 to 1/2 in other cell lines. Moreover, 7U95P showed no effects by R2 deletion in SAS-413 cells, but reduced its activity by about 1/7 to 1/2 in other cell lines. (FIG. 11).

(Summary)

The present Examples are summarized as follows:

1) 7MIEP(−493) and 7U95P(−494) both generally showed more potent activity than CMV promoter in T cell lines, but showed lower activity in the SAS-413 cell, which is a bone marrow cell line. In PBMC, 7MIEPO(−493) showed substantially the same activity as CMV promoter, and 7U95P(−494) showed lower activity than CMV promoter.

2) In comparison with HHV-6 IE promoters, all cell types showed higher activity in two types of IE promoters of HHV-6 (9U and U95) than 7MIEP(−493) and 7U95(−494).

3) It was shown that the R2 region functions as an enhancer against 7MIEP and 7U95P in a number of cells. Transcriptional factors binding to the R2 region are unidentified, but in view of the fact that the R3 region of HHV-6 functions as an enhancer of the U95 promoter by binding NF-κB, it is highly likely that the NF-κB binding motifs present in a repetitive manner in the R2 region may be responsible for enhancer activity of the R2 region (FIG. 8).

Example 3

Construction of Specific Deletion System

Knocking out of gene expression in blood cell lineage cells is conducted using an IE promoter and the RNAi method. IE promoters are advantageous for analysis since they are expressed in blood cell lineage cells in a large amount.

1) Preparation of Cells (in the Case of Macrophages)

Healthy human peripheral blood is obtained and separated and purified by density gradient using Ficoll/Hypaque. The PBMCs are cultured in a AIM V serum medium (Life Technologies) supplemented with M-CSF (R&D systems, 100 U/ml). The medium is exchanged every three days, and macrophages at Day 6 or 7 are used for experiments.

2) Preparation of siRNA Expression Retrovirus Vector

In order to express hair-pin type RNA, a synthetic oligo-DNA comprising "a sense strand target sequence", "a loop sequence", "an antisense strand target sequence" and "a terminator sequence" is prepared. Such a sense strand target sequence, loop sequence, antisense target sequence, terminator sequence may be made using well known technology in the art. Those skilled in the art can readily understand that when actually using these, an appropriate sequence may be employed depending on the actual situation.

The above-mentioned DNA is incorporated into a plasmid vector in which the oligo-DNA is linked downstream of the IE sequence, and of gag, pol and env which are necessary for replication of a retrovirus, and which comprises $Neo^R$ gene making use of restriction enzyme sequences and the like. Plasmid vector produced (10 μl) is added to 100 μl of competent cells and transformation is conducted and cultured for 16 hours at 37 degrees Celsius after plating into LBAmp plate. Colonies obtained by the transformation are cultured on LBApm liquid medium at 37 degrees Celsius for 16 hours, and plasmids are extracted and purified using conventional methods from the culture solution.

Retrovirus packaging cells expressing gag, pol and env are plated on a disc with a 10 cm diameter, and transfection reagent is opened to transfect the plasmid (10 μg). 24-48 hours later, the cells are subjected to limitation dilution into G418 containing medium (500 μg/ml) and passaged.

Every three to four days, G418 medium is exchanged and cultured for about two weeks in total. Colonies are collected and at the time where growth is found at a confluent level on a six-well plate, the medium is changed to a G418 free medium and the supernatant is collected 24 hours later. The cells will be stocked.

Retrovirus vectors included in the supernatant are subjected to limitation dilution, and infected into NIH/3T3 cells, and colonies grown are counted to calculate the infection value.

3) Gene Introduction Experiments Using Retrovirus Vectors

Retrovirus vectors are infected with blood cell lineage cells such as macrophages prepared in 1). Immediately after washing, it was plated to form $0.5$-$2.5 \times 10^4$ cells/cm² on a plate. Twenty four hours after the infection, the medium is exchanged with G418 containing medium, and every three to four days, medium is exchanged. About two weeks later, gene introduced cells are obtained. The cells are used to confirm the expression level of the desired knocked out gene.

These experiments are conducted to actually confirm that after gene introduction, lymphocyte specific expression of a foreign gene can be knocked out with the promoter of the present invention.

Example 4

Specific Expression

Instead of the RNAi of Example 3, a nucleic acid molecule encoding a gene (for example, cytokines such as TGF β) desired for expression is introduced.

As a result, by conducting similar experiments as in Example 3, after gene introduction, it is confirmed that the promoter according to the present invention actually induces the lymphocyte specific foreign gene expression.

As described above, the present invention is illustrated by way of the preferred embodiments. However, it will be understood that the scope of the present invention should be interpreted only by the accompanying claims. It will also be understood that the patents, patent applications and literature cited herein should be incorporated by reference as if set forth fully herein. Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

INDUSTRIAL APPLICABILITY

The present invention provides promoters which selectively induce the expression of protein in an immune responsible cells such as T lymphocytes. The promoters of the present invention are useful in method and medicaments for effectively preventing or treating immune diseases such as acquired immunodeficiency syndromes and the like. The present invention is also useful in the technologies for efficiently conducting gene therapy.

What is claimed is:

1. An isolated nucleic acid comprising a U95 promoter of HHV7, comprising the sequence set forth in SEQ ID NO: 12, wherein the nucleic acid has promoter activity.

2. A nucleic acid construct comprising the isolated nucleic acid according to claim 1.

3. The nucleic acid construct according to claim 2, which comprises a sequence encoding a gene foreign to a host into which the nucleic acid construct is introduced and not originally related to the promoter, operatively linked to the sequence of the promoter.

4. The nucleic acid construct according to claim 3, wherein the gene foreign to the host encodes an RNAi molecule, a drug, a recessive gene to be deleted, or a selective marker.

5. The nucleic acid construct according to claim 4, wherein the selective marker allows selection in a medium of a host in which the nucleic acid construct is introduced.

6. The nucleic acid construct according to claim 4, wherein the selective marker allows visual selection in a host in which the nucleic acid construct is introduced.

7. The nucleic acid construct according to claim 4, wherein the selective marker comprises hypoxanthine guanine phosphoribosyl transferase (hprt) or a fluorescent marker selected from the group consisting of green fluorescent protein (GFP), cyan fluorescent protein (CFP), yellow fluorescent protein (YFP) and red fluorescent protein (dsRed).

8. The nucleic acid construct according to claim 4, wherein the selective marker does not exhibit toxicity against the host in which the nucleic acid construct is introduced.

9. The nucleic acid construct according to claim 4, wherein the recessive gene to be deleted is selected from the group consisting of ADA gene, PNP gene, γ c chain gene, TAP gene, MHC II gene, X-linked WASP, CD40 ligand, PI3K-like gene and DNA helicase.

10. The nucleic acid construct according to claim 4, wherein the drug is selected from the group consisting of a cytokine, a chemokine, a growth factor, a protein hormone, and a peptide hormone.

11. The nucleic acid construct according to claim 3, wherein the promoter induces specific expression of the foreign gene in a hemocyto-lineage cell.

12. An expression vector comprising the nucleic acid construct according to claim 2.

13. An isolated cell comprising the nucleic acid construct according to claim 2.

14. An isolated tissue comprising the nucleic acid construct according to claim 2.

15. An isolated organ comprising the nucleic acid construct according to claim 2.

16. A method for expressing a protein in a lymphocyte specific manner, comprising the steps of:
  A) preparing a nucleic acid construct in which the isolated nucleic acid according to claim 1 is operatively linked to a nucleic acid sequence encoding the protein; and
  B) placing the nucleic acid construct under a condition in which the promoter induces the expression of the nucleic acid sequence encoding the protein.

17. A kit for expressing a protein in a lymphocyte specific manner, comprising:
  A) a nucleic acid construct in which the isolated nucleic acid according to claim 1 is operatively linked to a nucleic acid sequence encoding the protein; and
  B) means for placing the nucleic acid construct under a condition in which the promoter induces the expression of the nucleic acid sequence encoding the protein.

18. A kit for expressing a protein in a lymphocyte specific manner, comprising:
  A) the isolated nucleic acid according to claim 1; and
  B) means for producing a nucleic acid construct in which the promoter is linked to a nucleic acid sequence encoding the protein.

* * * * *